(12) United States Patent
Danitz et al.

(10) Patent No.: US 6,685,715 B2
(45) Date of Patent: Feb. 3, 2004

(54) CLAMP HAVING BENDABLE SHAFT

(75) Inventors: David J. Danitz, Cupertino, CA (US); Adam C. Gold, San Francisco, CA (US)

(73) Assignee: Novare Surgical Systems, Cupertino, CA (US)

( * ) Notice: Subject to any disclaimer, the term of this patent is extended or adjusted under 35 U.S.C. 154(b) by 0 days.

(21) Appl. No.: 10/364,131

(22) Filed: Feb. 11, 2003

(65) Prior Publication Data

US 2003/0120290 A1 Jun. 26, 2003

Related U.S. Application Data

(63) Continuation-in-part of application No. 10/136,983, filed on May 1, 2002, which is a continuation-in-part of application No. 10/013,207, filed on Dec. 7, 2001, which is a continuation-in-part of application No. 09/847,135, filed on May 2, 2001, now Pat. No. 6,544,274.

(51) Int. Cl.⁷ ................................................. A61B 17/08
(52) U.S. Cl. ........................ 606/157; 606/158; 606/205
(58) Field of Search ................................. 606/151, 157, 606/158, 205; 600/123, 124, 125, 139, 141, 142, 40; 604/523, 524, 525, 535

(56) References Cited

U.S. PATENT DOCUMENTS

| | | | | |
|---|---|---|---|---|
| 3,266,059 A | * | 8/1966 | Stelle | 138/120 |
| 4,054,128 A | * | 10/1977 | Seufert et al. | 285/9.1 |
| 4,790,298 A | * | 12/1988 | Trick | 600/40 |
| 5,318,528 A | | 6/1994 | Heaven | 604/95 |
| 5,395,367 A | | 3/1995 | Wilk | 606/1 |
| 5,411,514 A | | 5/1995 | Fucci et al. | 606/180 |
| 5,450,842 A | | 9/1995 | Tovey | 600/206 |
| 5,467,763 A | | 11/1995 | McMahon et al. | 600/201 |
| 5,511,564 A | | 4/1996 | Wilk | 128/898 |
| 5,514,076 A | | 5/1996 | Ley | 600/206 |
| 5,514,115 A | | 5/1996 | Frantzen | 604/281 |
| 5,520,222 A | * | 5/1996 | Chikama | 138/103 |
| 5,558,665 A | | 9/1996 | Kieturakis | 606/1 |
| 5,593,416 A | | 1/1997 | Donahue | 606/170 |
| 5,626,607 A | * | 5/1997 | Malecki et al. | 606/205 |
| 5,632,746 A | | 5/1997 | Middleman | 606/78 |
| 5,680,982 A | | 10/1997 | Schulze et al. | 600/139 |
| 5,752,969 A | | 5/1998 | Cunci et al. | 606/167 |
| 5,772,578 A | | 6/1998 | Heimberger et al. | 600/139 |
| 5,851,208 A | | 12/1998 | Trott | 606/80 |
| 5,876,330 A | | 3/1999 | Grabover et al. | 600/129 |
| 5,916,147 A | * | 6/1999 | Boury | 600/139 |
| 6,019,722 A | | 2/2000 | Spence et al. | 600/210 |
| 6,036,706 A | | 3/2000 | Morejohn et al. | 606/158 |
| 6,139,563 A | | 10/2000 | Cosgrove, III et al. | 606/205 |
| 6,146,394 A | * | 11/2000 | Morejohn et al. | 606/158 |
| 6,156,047 A | | 12/2000 | Spauling | 606/159 |
| 6,238,414 B1 | | 5/2001 | Griffiths | 606/205 |
| 6,323,459 B1 | * | 11/2001 | Maynard | 219/209 |
| 6,461,363 B1 | | 10/2002 | Gadberry et al. | 606/139 |
| 2001/0049540 A1 | | 12/2001 | Santilli | 606/158 |

FOREIGN PATENT DOCUMENTS

| | | |
|---|---|---|
| JP | 404135554 | 11/1992 |
| WO | WO 95/00197 | 1/1995 |
| WO | WO 98/24371 | 6/1998 |
| WO | WO 98/40020 | 9/1998 |
| WO | WO 99/42036 | 8/1999 |

* cited by examiner

Primary Examiner—Cary E. O'Connor
(74) Attorney, Agent, or Firm—Raymond Sun

(57) ABSTRACT

A clamp has a handle assembly and a gripping assembly having a pair of jaws that can be opened and closed to grip an element, the pair of jaws being parallel to each other when they are opened and when they are closed. The clamp also has a flexible shaft having a proximal end that is operatively coupled to the handle assembly and a distal end that is operatively coupled to the gripping assembly.

10 Claims, 45 Drawing Sheets

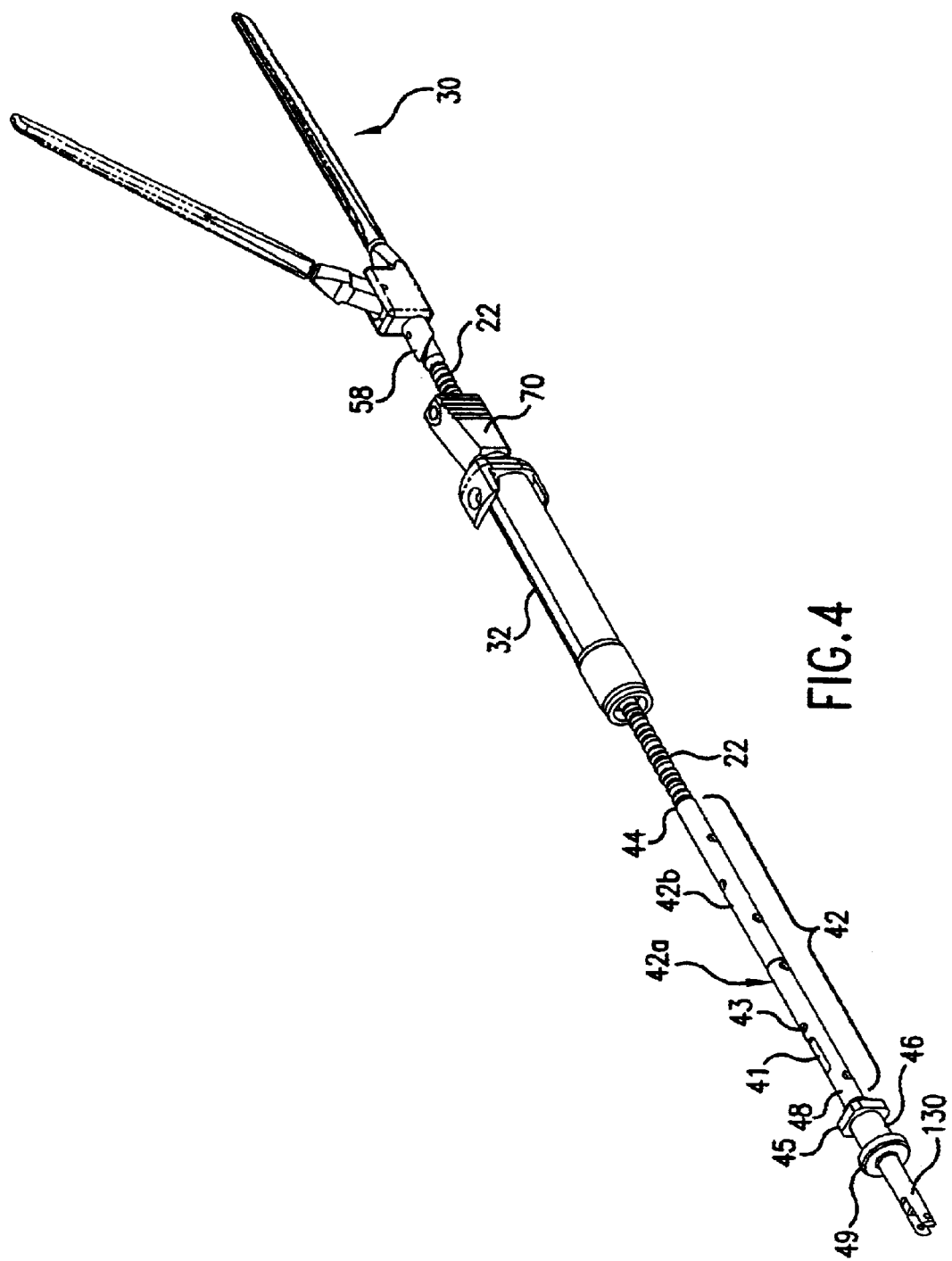

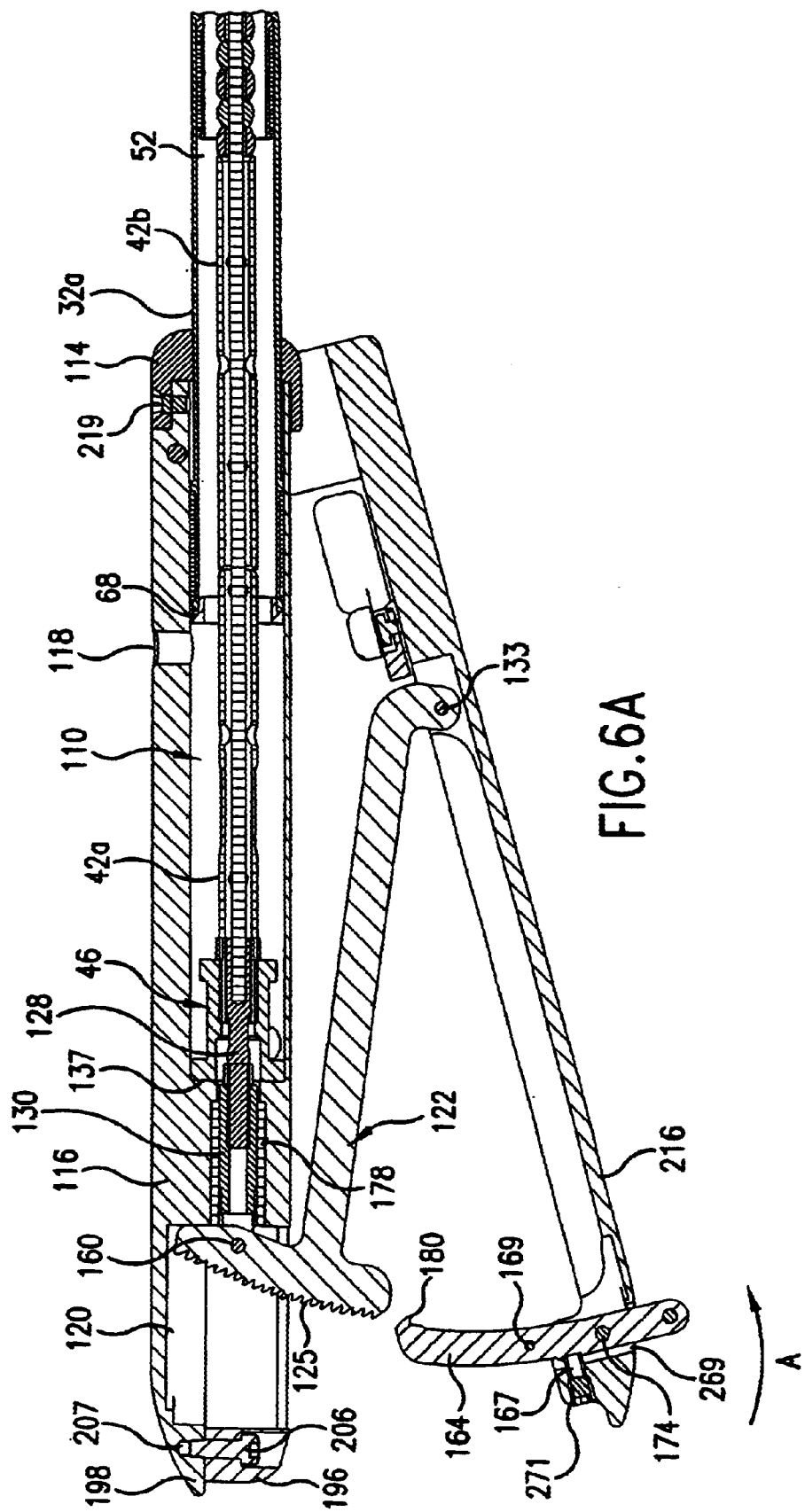

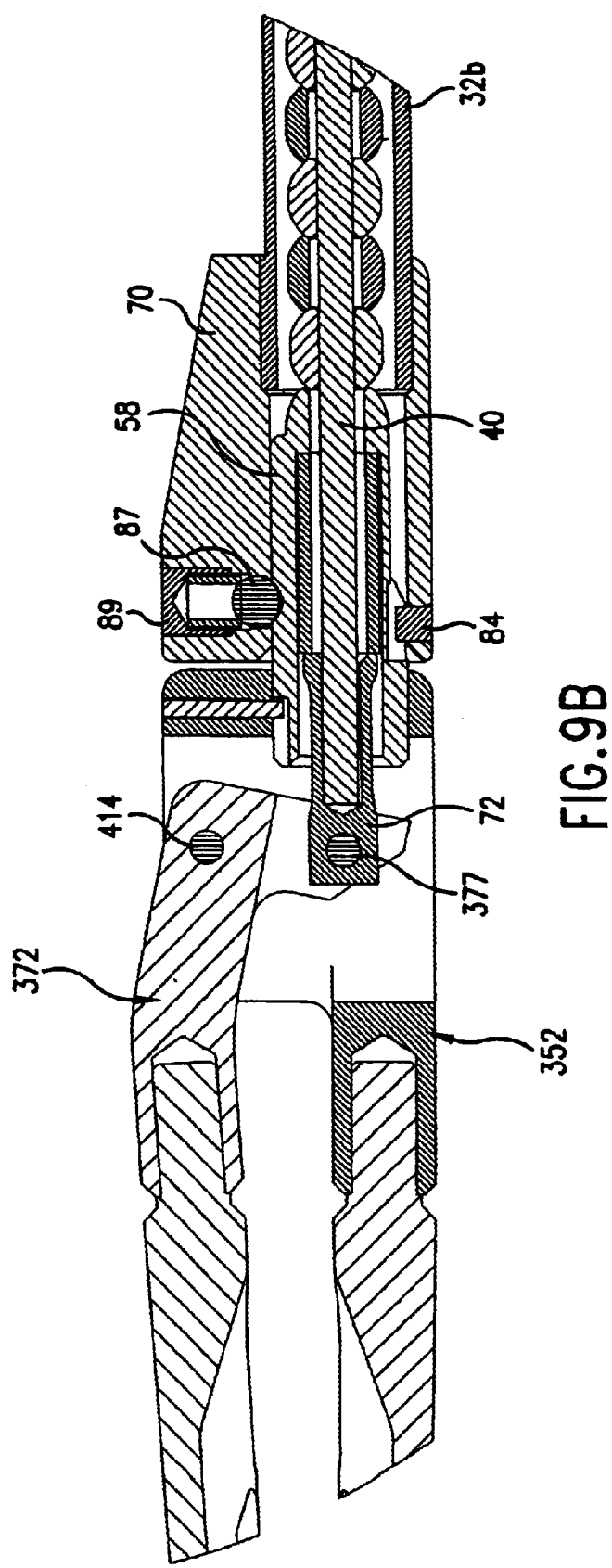

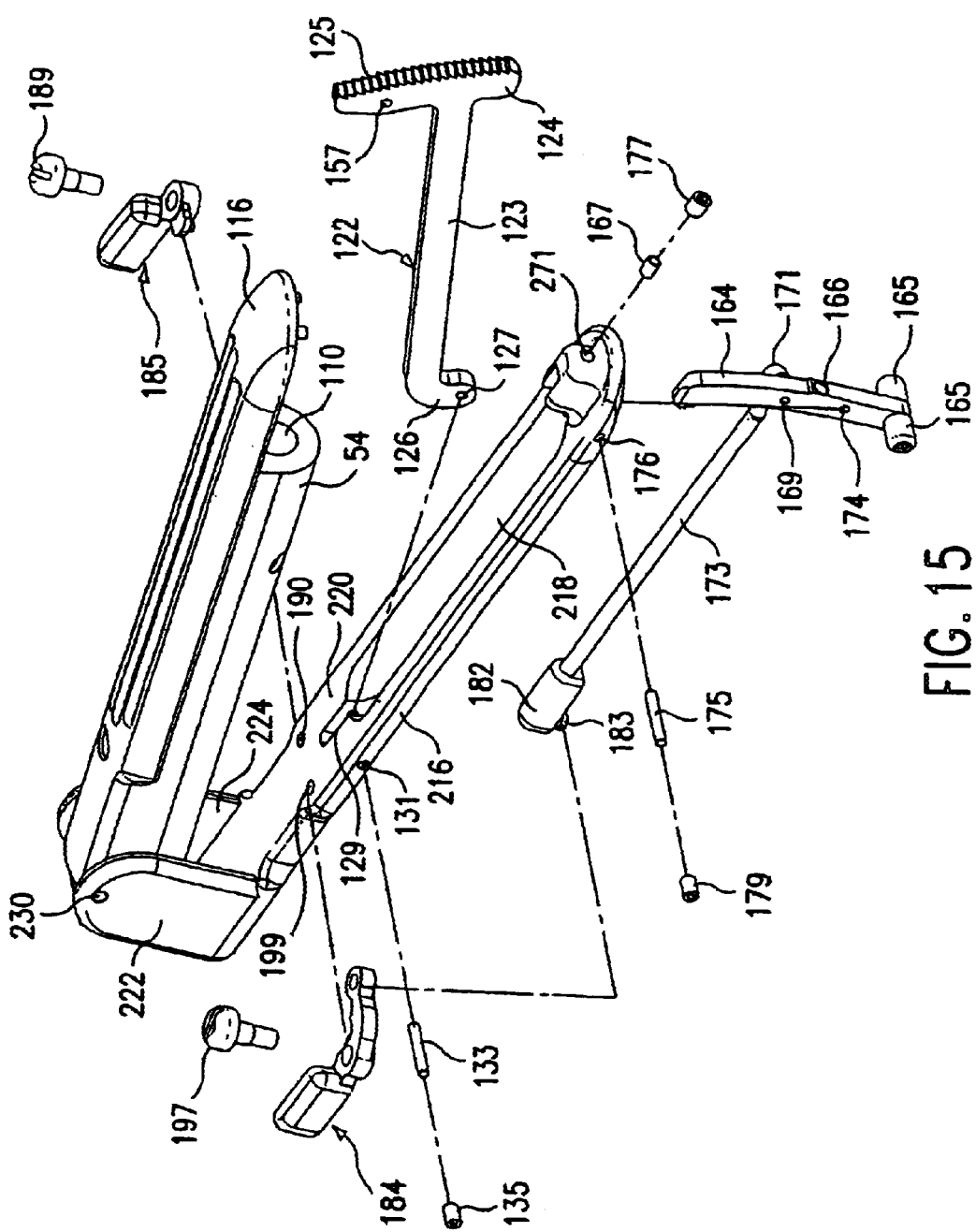

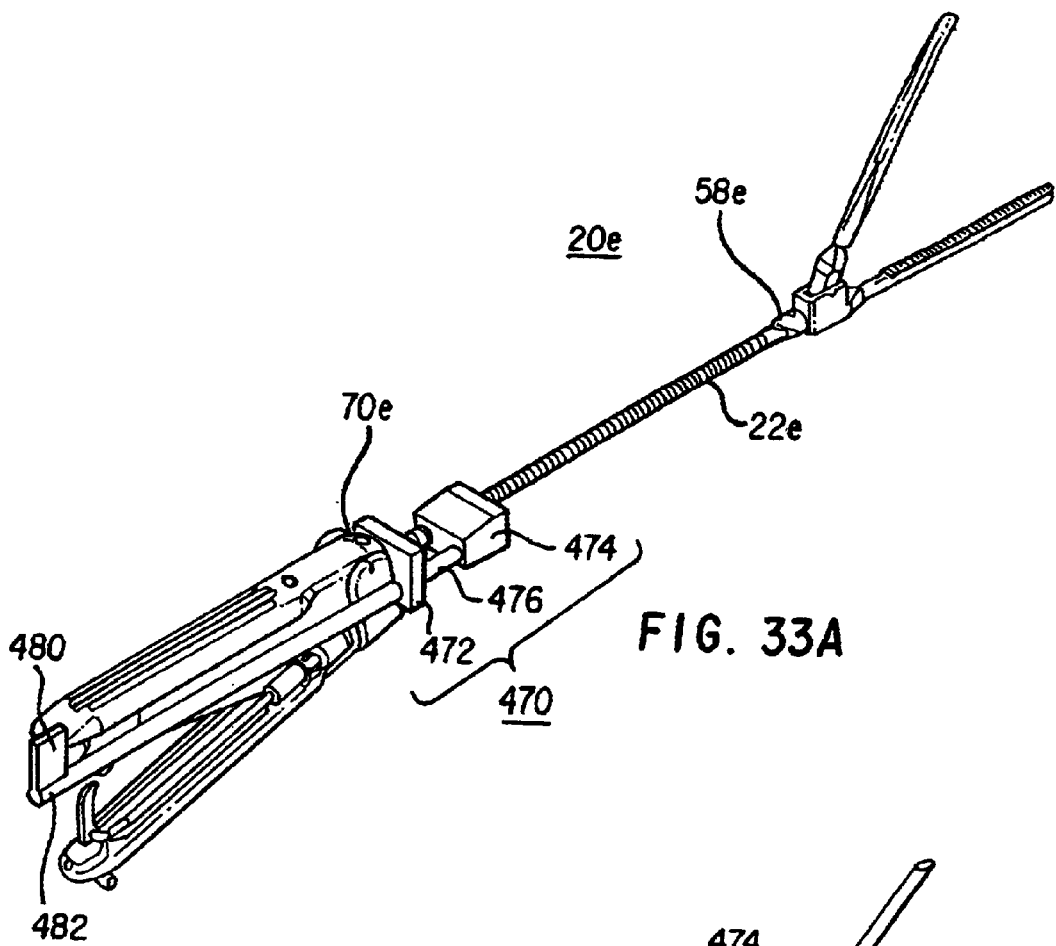
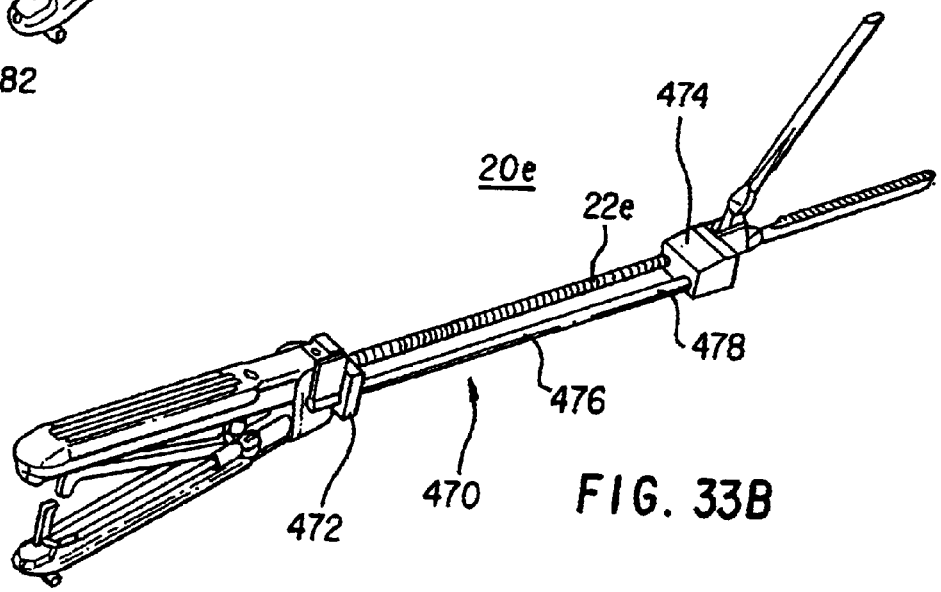

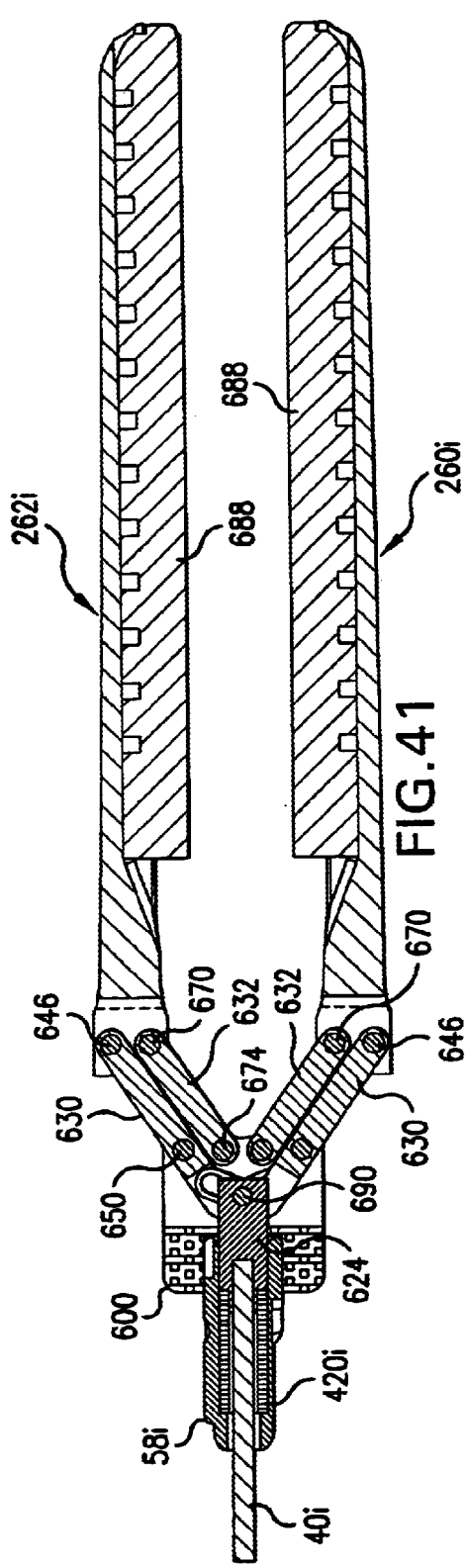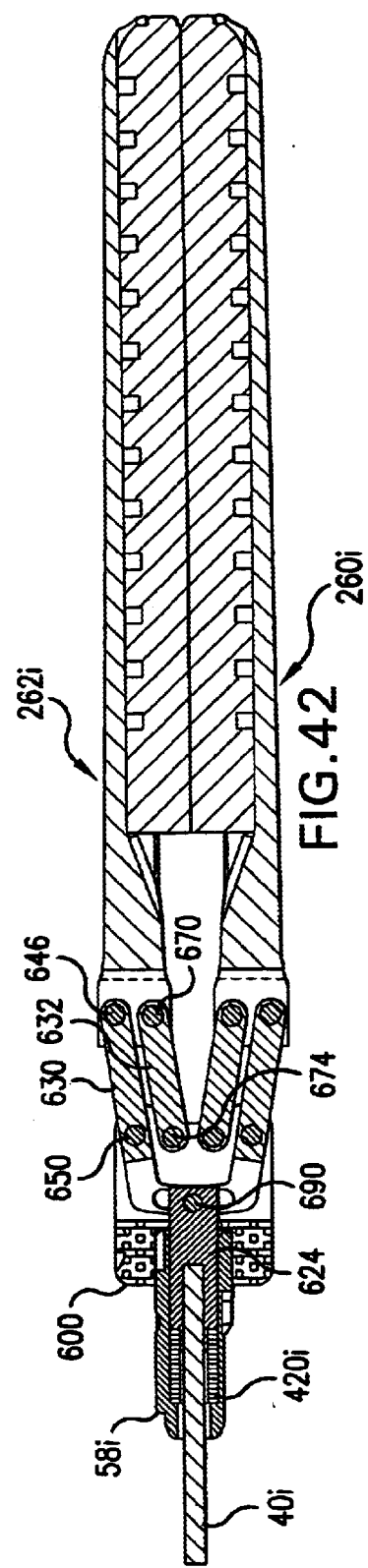

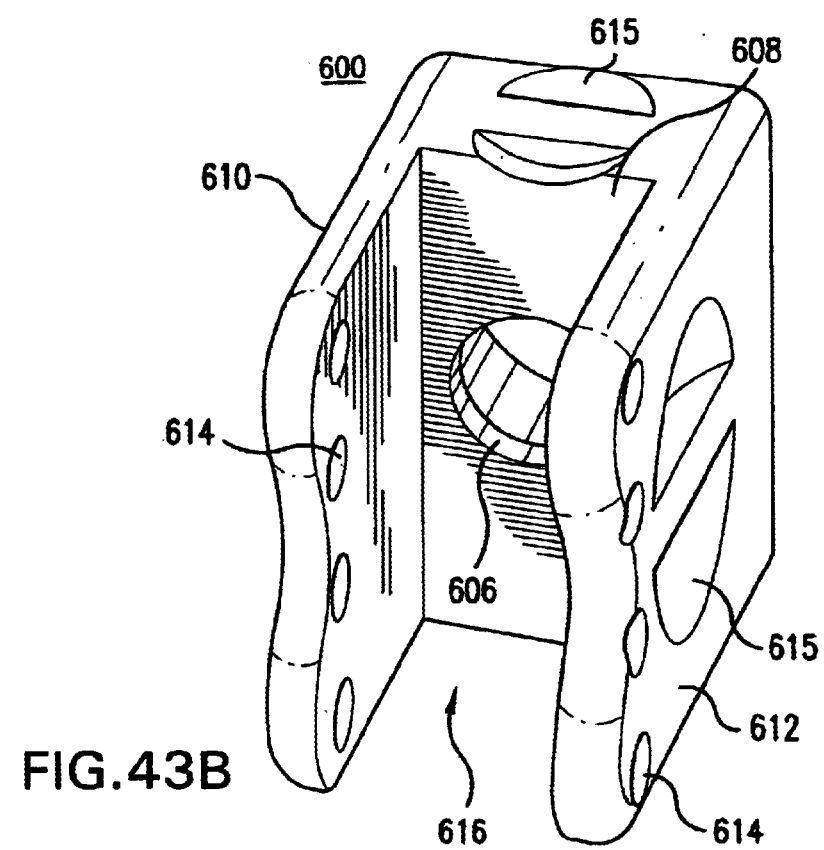
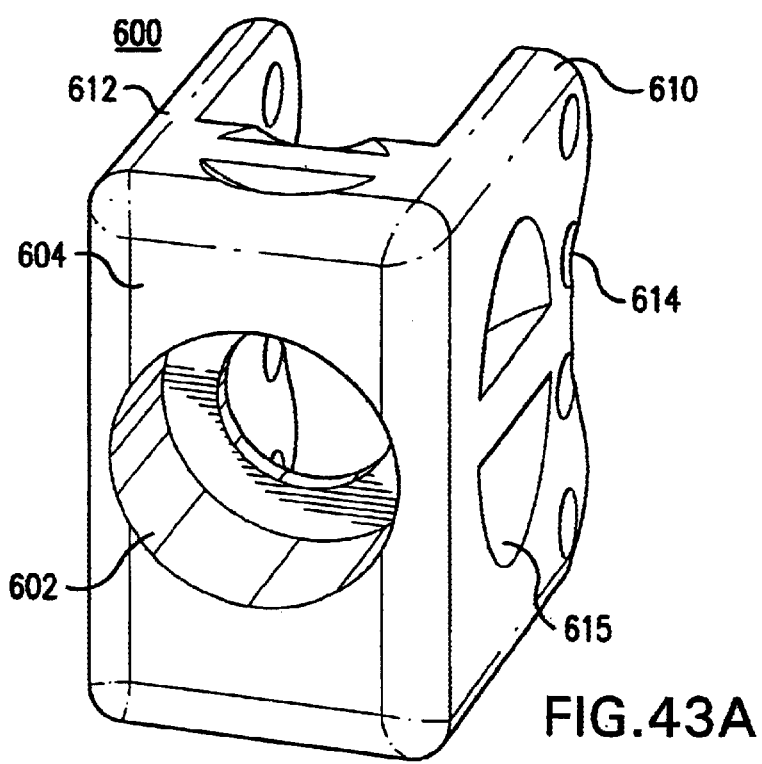
FIG.43B
FIG.43A

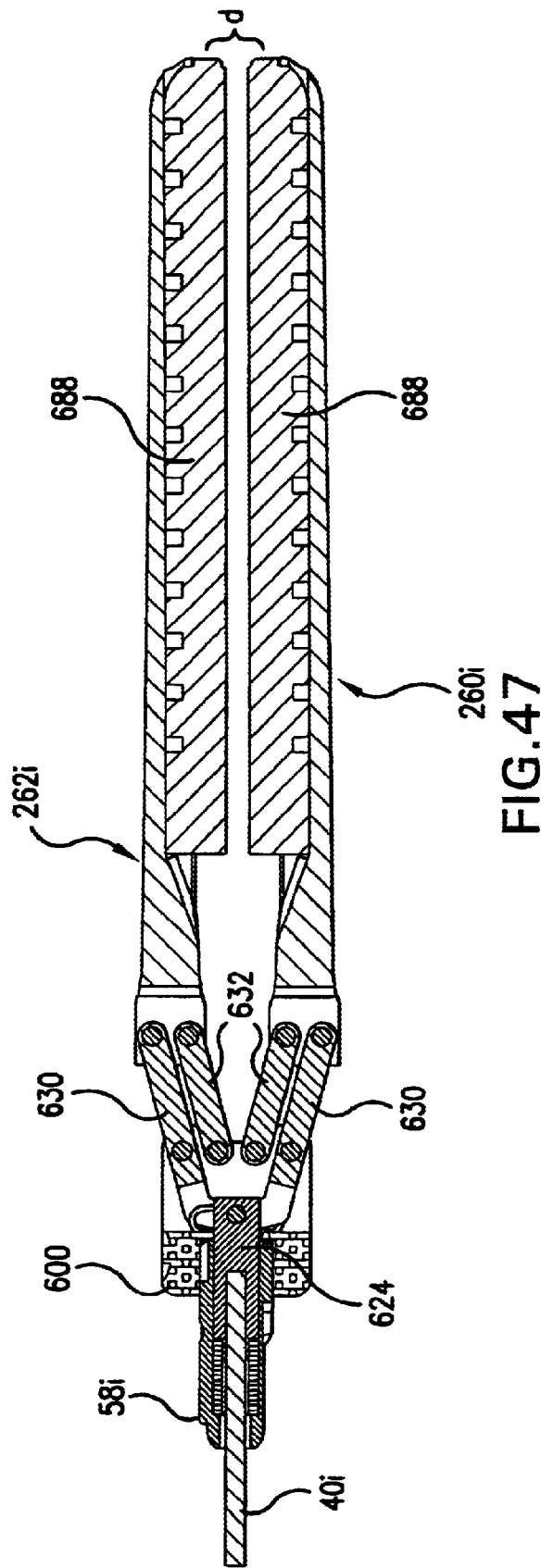

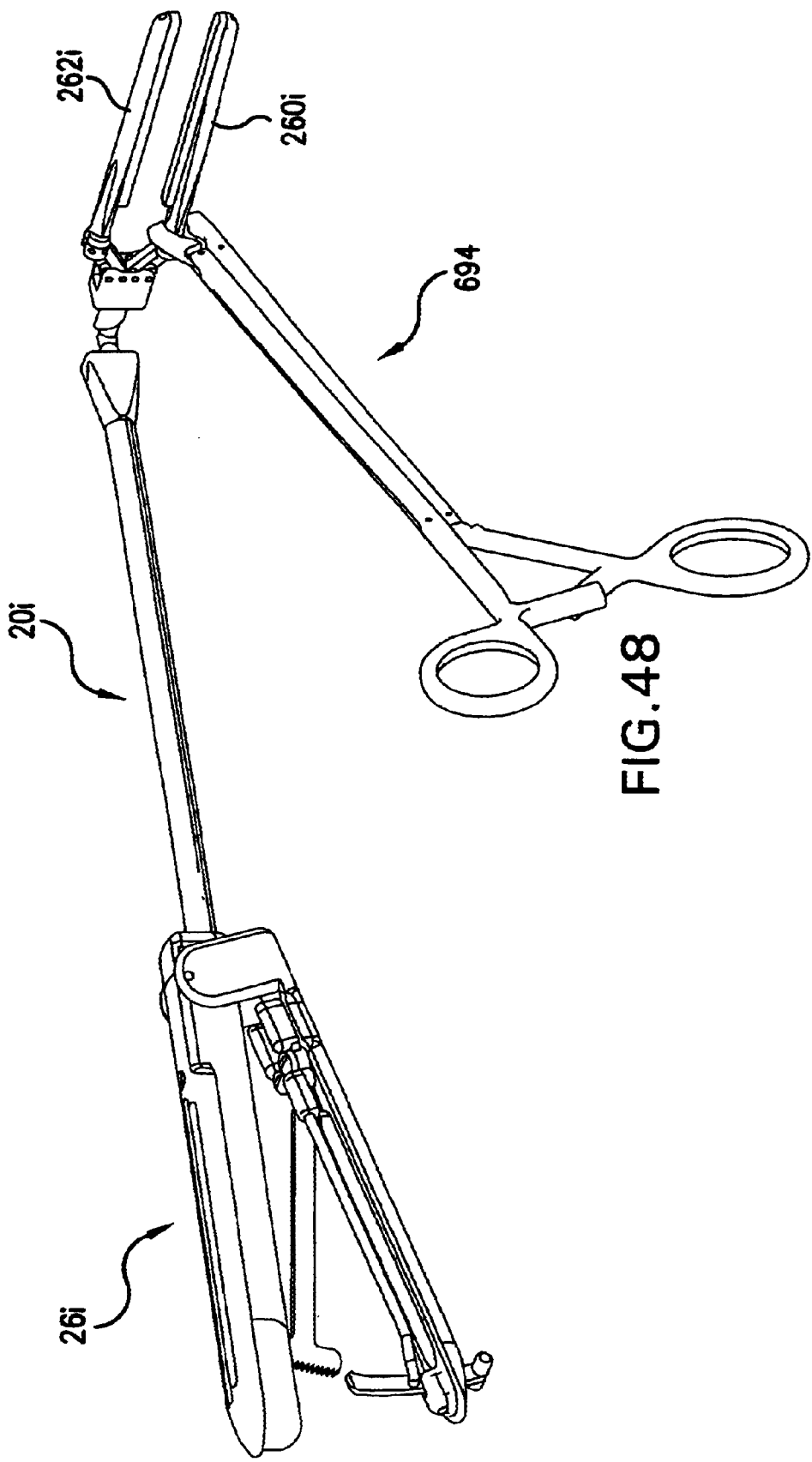

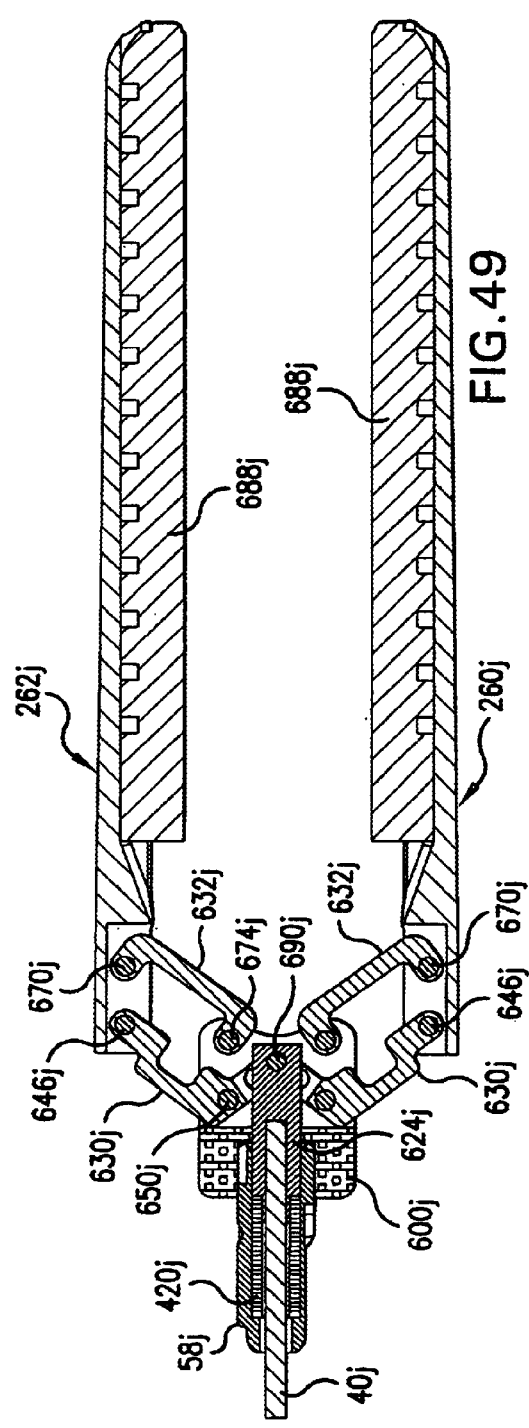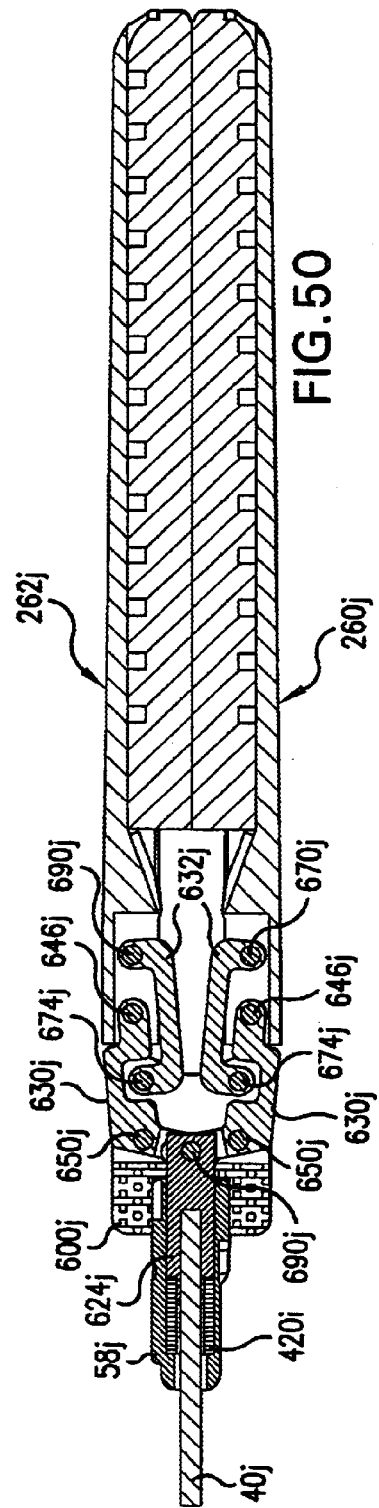

CLAMP HAVING BENDABLE SHAFT

RELATED CASES

This is a continuation-in-part of application Ser. No. 10/136,983, filed May 1, 2002, pending which is in turn a continuation-in-part of application Ser. No. 10/013,207, pending filed Dec. 7, 2001, which is in turn a continuation-in-part of application Ser. No. 09/847,135, filed May 2, 2001, U.S. Pat. No. 6,544,274, whose disclosures are incorporated by this reference as though set forth fully herein.

BACKGROUND OF THE INVENTION

1. Field of the Invention

The present invention relates to medical devices, and in particular, to a clamping device that has a bendable shaft.

2. Description of the Prior Art

Clamping devices are typically used to occlude blood vessels during a surgical procedure. Conventional clamping devices are also known as clamps, and have a shaft that connects a pair of jaws with a handle at opposite ends thereof. The pair of jaws open and close about a pivot point in a motion that resembles that of a scissors. These conventional clamps are typically made from stainless steel and the shaft is therefore completely rigid. As a result, such conventional clamps are bulky and can interfere with the surgeon's access to the surgical site. To address this problem, elastic bands were sometimes used to hold the handles of the clamp away from the location of the surgical site.

With the increasing popularity of minimally invasive surgical procedures, access to the surgical site is reduced, thereby creating a need for smaller clamping devices, or clamping devices that can be moved away from the surgical site after the blood vessel has been clamped by the clamping device. As a result, the conventional clamps pose significant access problems to the surgeon when used during minimally invasive surgical procedures.

Thus, there remains a need for an improved clamping device that can be used to effectively clamp a blood vessel at a surgical site, while not interfering with the surgeon's access to the surgical site.

SUMMARY OF THE DISCLOSURE

It is an object of the present invention to provide a clamp that does not interfere with a surgeon's access to the surgical site during use.

It is another object of the present invention to provide a clamp that can effectively clamp a blood vessel at a surgical site.

It is yet another object of the present invention to provide a clamp whose handle can be moved away from the surgical site after the clamp has clamped the blood vessel.

It is yet another object of the present invention to provide a clamp that has a shaft which can be both completely rigid and completely flexible, with the rigid shaft being capable of withstanding axial loads, side loads, and moments applied to the jaws of the clamp.

It is yet another object of the present invention to provide a clamp that can be used in open and endoscopic surgeries.

It is yet another object of the present invention to provide a clamp that prevents rotation of the jaws when in use.

It is yet another object of the present invention to provide a clamp having a pair of parallel closing jaws.

It is yet another object of the present invention to provide a clamp having a pair of parallel closing jaws.

The objectives of the present invention are accomplished by providing a clamp having a handle assembly and a gripping assembly having a pair of jaws that can be opened and closed to grip an element, the pair of jaws being parallel to each other when they are opened and when they are closed. The clamp also has a flexible shaft having a proximal end that is operatively coupled to the handle assembly and a distal end that is operatively coupled to the gripping assembly.

The present invention also provides a method of performing a medical procedure using a clamp that has a handle assembly, a gripping assembly having a pair of jaws that can be opened and closed, and a flexible shaft having a proximal end that is operatively coupled to the handle assembly and a distal end that is operatively coupled to the gripping assembly. According to the method, the jaws are inserted through an incision or port, and then a secondary instrument is inserted through either the same incision or port, or through a different incision or port, so that the secondary instrument can grip the jaws and articulate the jaws to a desired position. The jaws can then be closed to grip a blood vessel or tissue.

BRIEF DESCRIPTION OF THE DRAWINGS

FIG. 4 is a perspective sectional view of the shaft assembly of the clamp of FIG. 1.

FIG. 6A is a cross-sectional view of the handle assembly of the clamp of FIG. 1 with the telescoping tubes deployed over the shaft.

FIG. 9B is a cross-sectional view of the gripping assembly of the clamp of FIG. 1 with the jaws closed and the lock mechanism locked with the helix cylinder.

FIG. 15 is an exploded perspective view of the handle assembly of the clamp of FIG. 1.

FIG. 33A is a perspective view of a rigid support assembly according to another embodiment shown in use with the clamp of FIG. 2.

FIG. 33B is a perspective view of the clamp and rigid support assembly of FIG. 33A.

FIG. 41 is an enlarged cross-sectional view of the gripping assembly of FIG. 39 shown with the jaws opened.

FIG. 42 is an enlarged cross-sectional view of the gripping assembly of FIG. 39 shown with the jaws closed.

FIG. 43A is a proximal perspective view of the jaw housing of the gripping assembly of FIG. 39.

FIG. 43B is a distal perspective view of the jaw housing of the gripping assembly of FIG. 39.

FIG. 47 is an enlarged cross-sectional view of a modification made to the gripping assembly of FIG. 39 shown with the jaws closed.

FIG. 48 is a perspective view of the gripping assembly of FIG. 39 illustrating the use of a second instrument to articulate the jaws of the gripping assembly.

FIG. 49 is an enlarged cross-sectional view of an alternative gripping assembly for the clamp of FIG. 39 shown with the jaws opened.

FIG. 50 is an enlarged cross-sectional view of the gripping assembly of FIG. 49 shown with the jaws closed.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

The present invention provides a clamping device that has a flexible and bendable shaft that can be supported by a rigid element. When the clamping device is being held and controlled by the surgeon prior to clamping a blood vessel, tissue or other anatomical structure, the rigid element can be deployed to support the flexible shaft so that the entire clamping device is generally rigid. After the clamping device has been used to clamp a blood vessel, tissue or other anatomical structure, the rigid element can be withdrawn or otherwise removed so that the flexible shaft can be conveniently bent by the surgeon to a position or location so that the handle assembly does not interfere with access to the surgical site.

Figure 1:
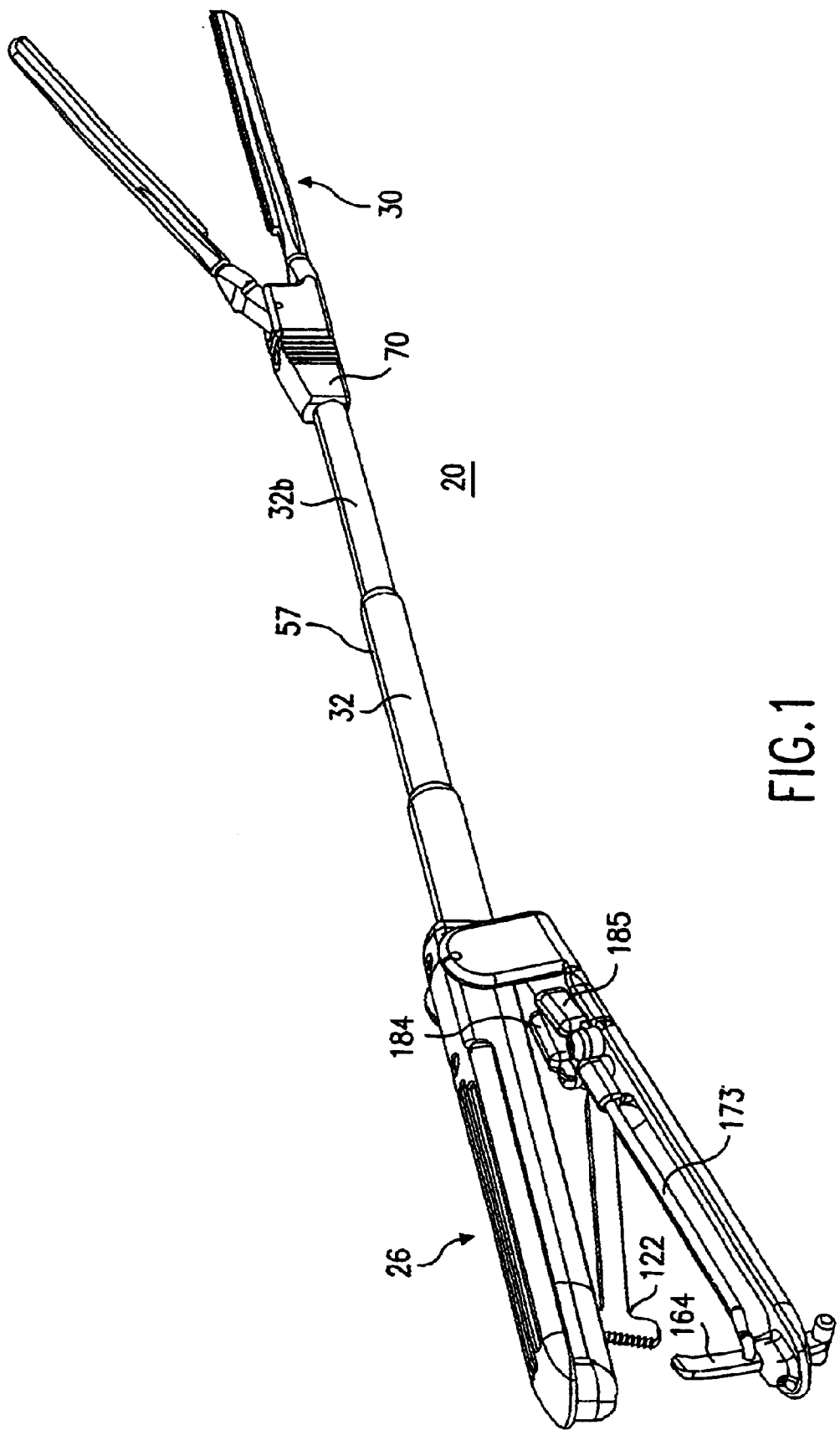
FIG. 1 is a perspective view of a clamp according to the present invention with the shaft completely covered by telescoping tubes.
Figure 2:
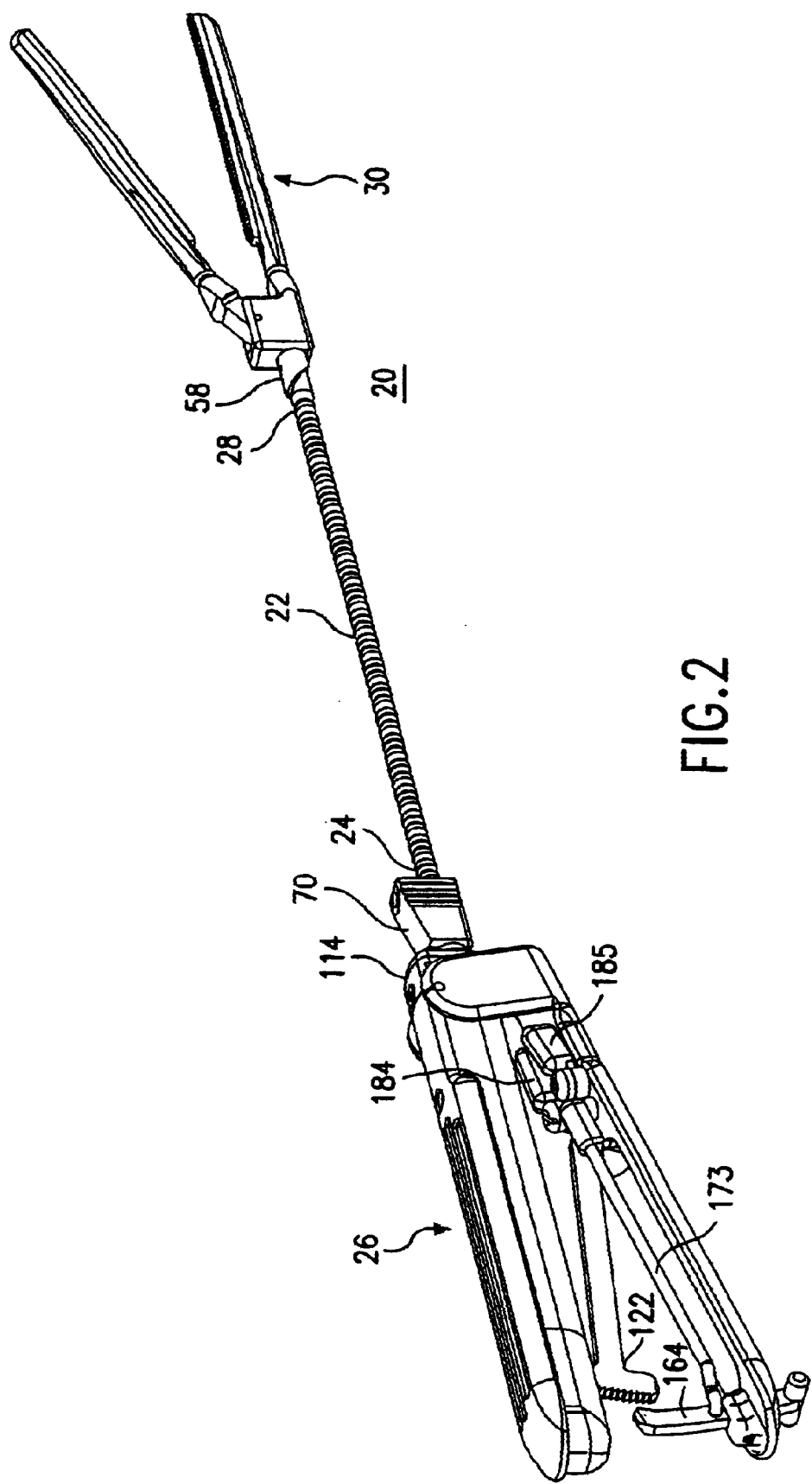
FIG. 2 is a perspective view of the clamp of FIG. 1 with the shaft not covered by telescoping tubes.

FIGS. 1 and 2 are perspective views illustrating the clamp 20 of the present invention. The clamp 20 has a shaft assembly having a flexible shaft 22 having a proximal end 24 that is operatively connected to a handle assembly 26, and a distal end 28 that is operatively connected to a gripping assembly 30. A plurality of telescoping tubes 32 can be withdrawn and stored in nested fashion inside the handle assembly 26 (see FIG. 2), or can be fully deployed to completely cover the shaft 22 (see FIG. 1).

Shaft Assembly and Telescoping Tubes

Referring now to FIGS. 2–5, the shaft 22 can be flexible to the point where it would be completely flexible (in other words, limp, flaccid, pliable, compliant and not stiff) when the shaft 22 is not supported by any other element, yet despite being completely flexible, is still capable of withstanding axial loads. In one embodiment that is best illustrated in FIGS. 3A and 3B, the shaft 22 can be made up of a plurality of two types of beads 36a and 36b that are alternated with respect to each other. Both types of beads 36a and 36b have a three-dimensional convex torus configuration, which is best shown in FIG. 3B. The first beads 36a have a smaller inner diameter than the second beads 36b. The first beads 36a have an outer diameter that is smaller than, equal to, or greater than, the outer diameter of the second beads 36b. Each second bead 36b rides (i.e., is supported) on the outer surface 37a of two adjacent first beads 36a, so that each second bead 36b is essentially in a raised position with respect to the first beads 36a. In particular, the convex circumferential portion 37b of each second bead 36b contacts or rides on the outer surface 37a of two adjacent first beads 36a. FIG. 3B illustrates four alternating beads 36a, 36b in a region X where all the beads 36a, 36b are shown connected to each other, and another three beads 36a, 36b in a region Y where the beads 36a, 36b are shown to be separated from each other solely for illustrative purposes. The beads 36a, 36b are preferably made of a material that is hard and stiff, with good wear properties. Non-limiting examples of such a material for the beads 36 include metal, plastics, composites and/or ceramics. Each bead 36a and 36b can have, in one embodiment, an inner diameter of about 0.03 to 0.20 and 0.05 to 0.22 inches, respectively, and an outer diameter of about 0.09 to 0.30 and 0.09 to 0.30 inches, respectively. Preferably, between a total of 10 to 100 beads 36a and 36b can be connected together to form the shaft 22.

Figure 3A:
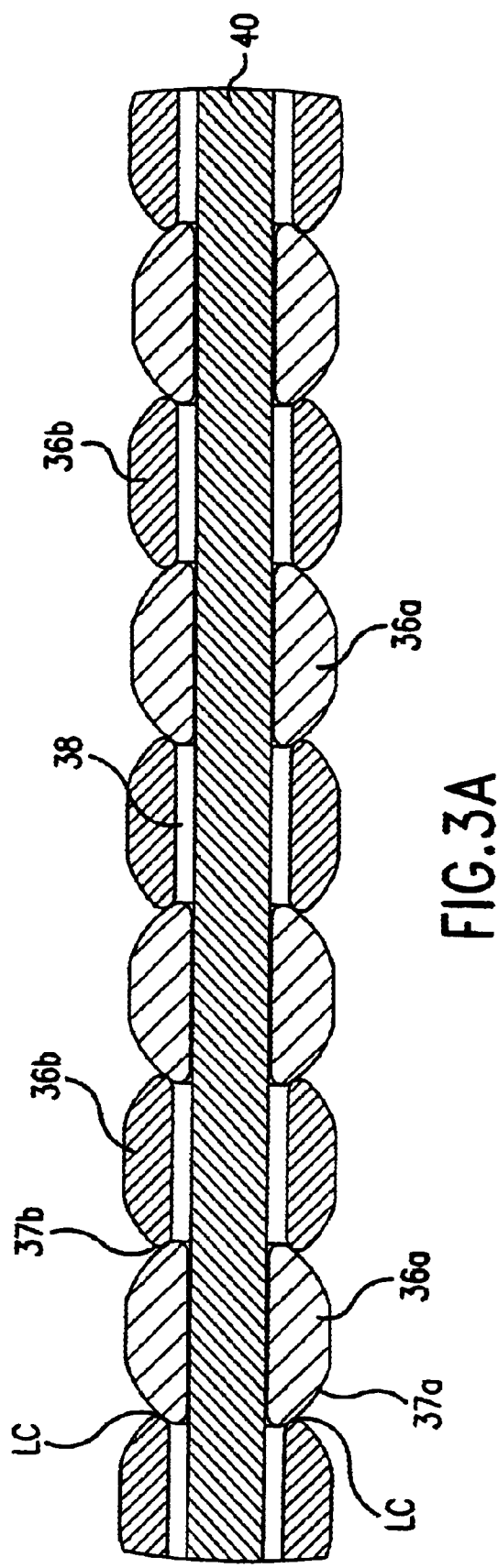
FIG. 3A is a cross-sectional view of a portion of the shaft of the clamp of FIG. 1.
Figure 3B:
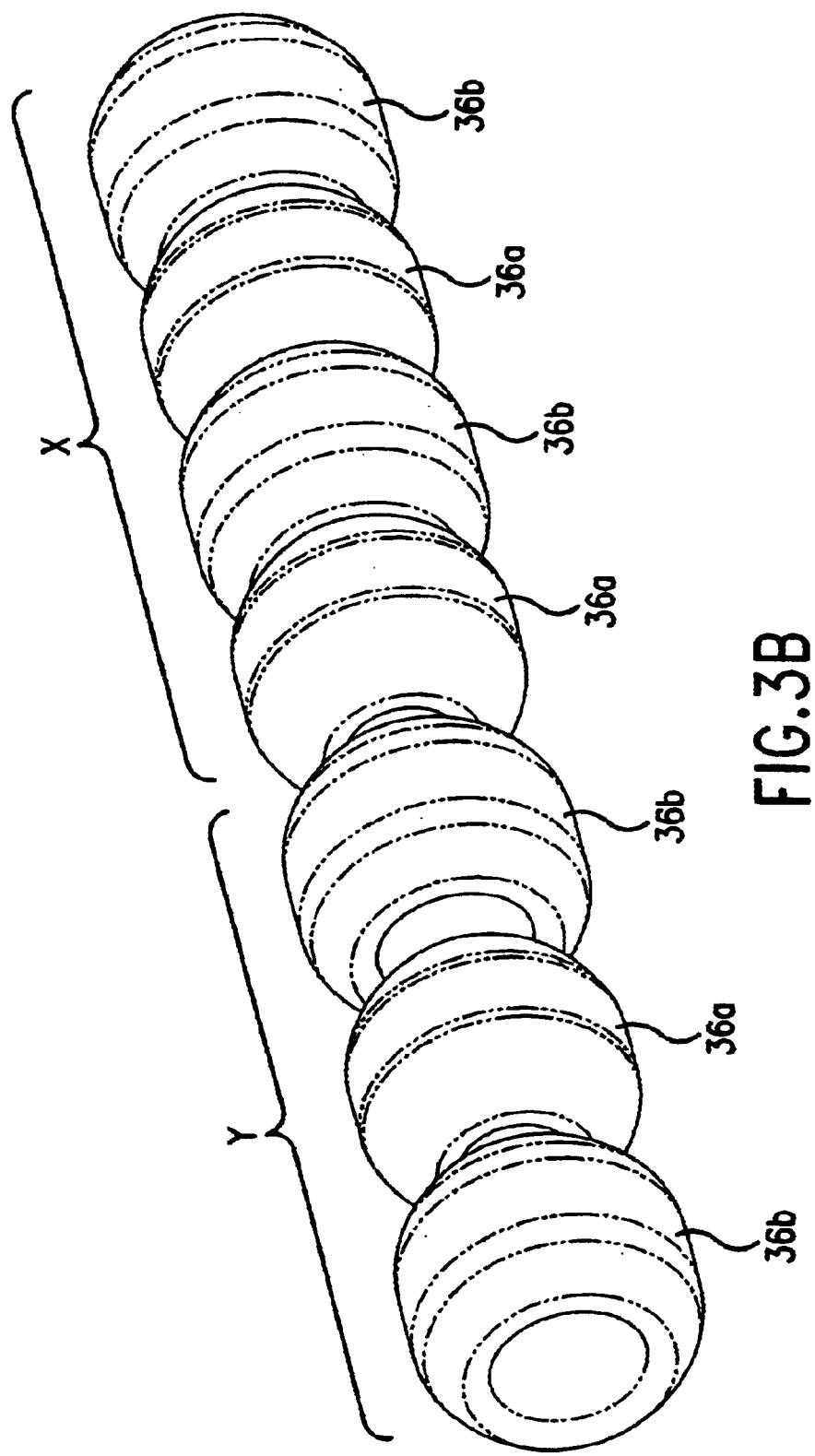
FIG. 3B is a perspective view of a portion of the shaft of FIG. 3A.

As shown in FIG. 3A, each bead 36a, 36b can be provided with a through-hole or bore 38 so as to form a longitudinal bore through the shaft 22, with an internal wire cable 40 retained inside the bores 38. The beads 36 are lined up side-by-side in abutting fashion to form the shaft 22. The construction of a shaft 22 having alternating first and second beads 36a, 36b has exhibited improved flexibility even when the jaws 260, 262 of the gripping assembly 30 are clamped together. The contact between the adjacent beads 36a, 36b can be characterized as a line contact (as contrasted with conventional ball-and-socket joints which have surface contacts), in which one bead 36a contacts an adjacent bead 36a, 36b along a ring of points (e.g., LC in FIG. 3A). The construction of the beads 36a, 36b enables the line contact between adjacent beads 36a, 36b to exist at all times, even when the shaft 22 is bent. This line contact between the adjacent beads 36a, 36b also minimizes the friction between adjacent beads 36a, 36b when the shaft 22 is bent. As a result, the shaft 22 illustrated in FIGS. 3A and 3B will be more flexible when the jaws 260, 262 of the gripping assembly 30 are closed, so that when the surgeon moves the handle assembly 26 away from the surgical site, less torque or force is transmitted to the blood vessel by the gripping assembly 30, and trauma to the blood vessel can be minimized.

The cable 40 is always in tension, and is utilized to control the opening and closing of the jaws 260, 262 of the gripping assembly 30, as will be described in greater detail below. The cable 40 can be embodied in the form of any conventional cable that is used in clamping devices, and can be made, for example, from stainless steel or tungsten, among other examples.

Figure 5:
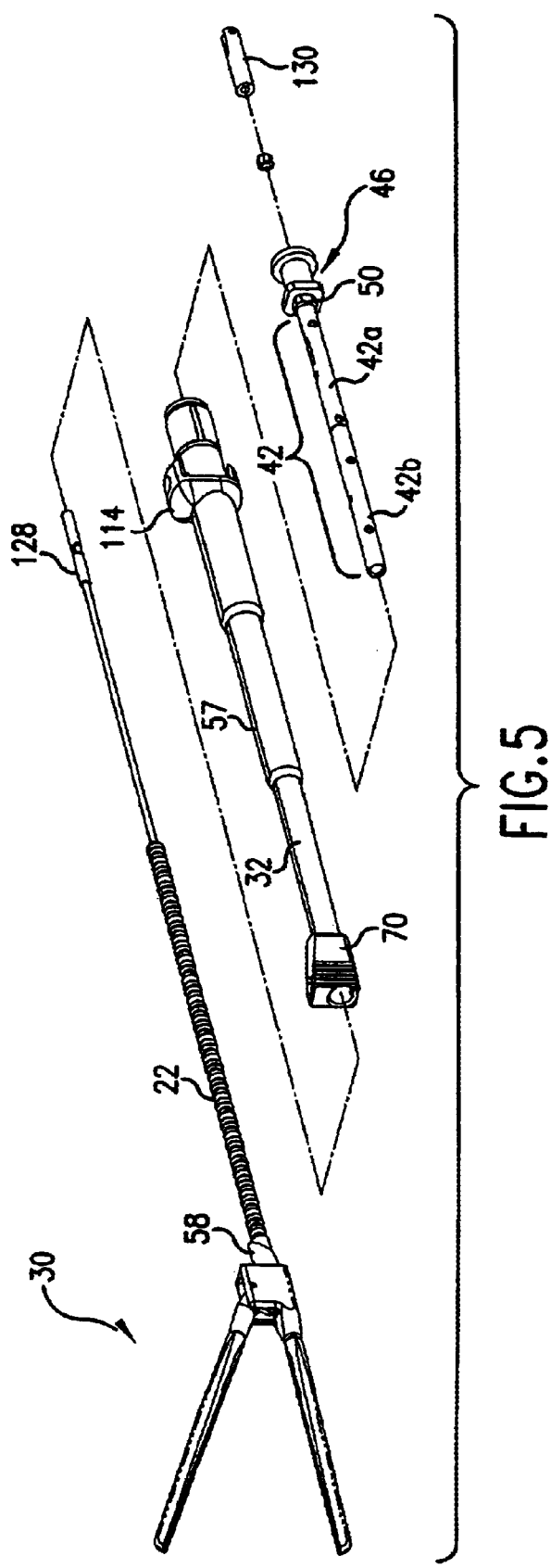
FIG. 5 is an exploded perspective view of the shaft assembly of the clamp of FIG. 1.

The proximal end 24 of the shaft 22 abuts a distal end 44 of a proximal tube 42 that is secured inside the handle assembly 26, as shown in FIGS. 4 and 6A. The proximal tube 42 can be provided in one piece, or in a plurality of pieces (e.g., two separate pieces 42a, 42b as shown in FIGS. 4 and 5) for easier manufacturing, and can include holes 43 that allow for flushing of the cable 40 during cleaning. When provided in two or more pieces, each separate piece (e.g., 42a and 42b in FIG. 4) can have chamfered ends (not shown) that are adapted to mate or couple with the adjacent piece. In addition, one or more of the separate pieces 42a, 42b can have a flat region 41 that facilitates convenient gripping (e.g., by a wrench) during assembly of the clamp 20.

Figure 6B:
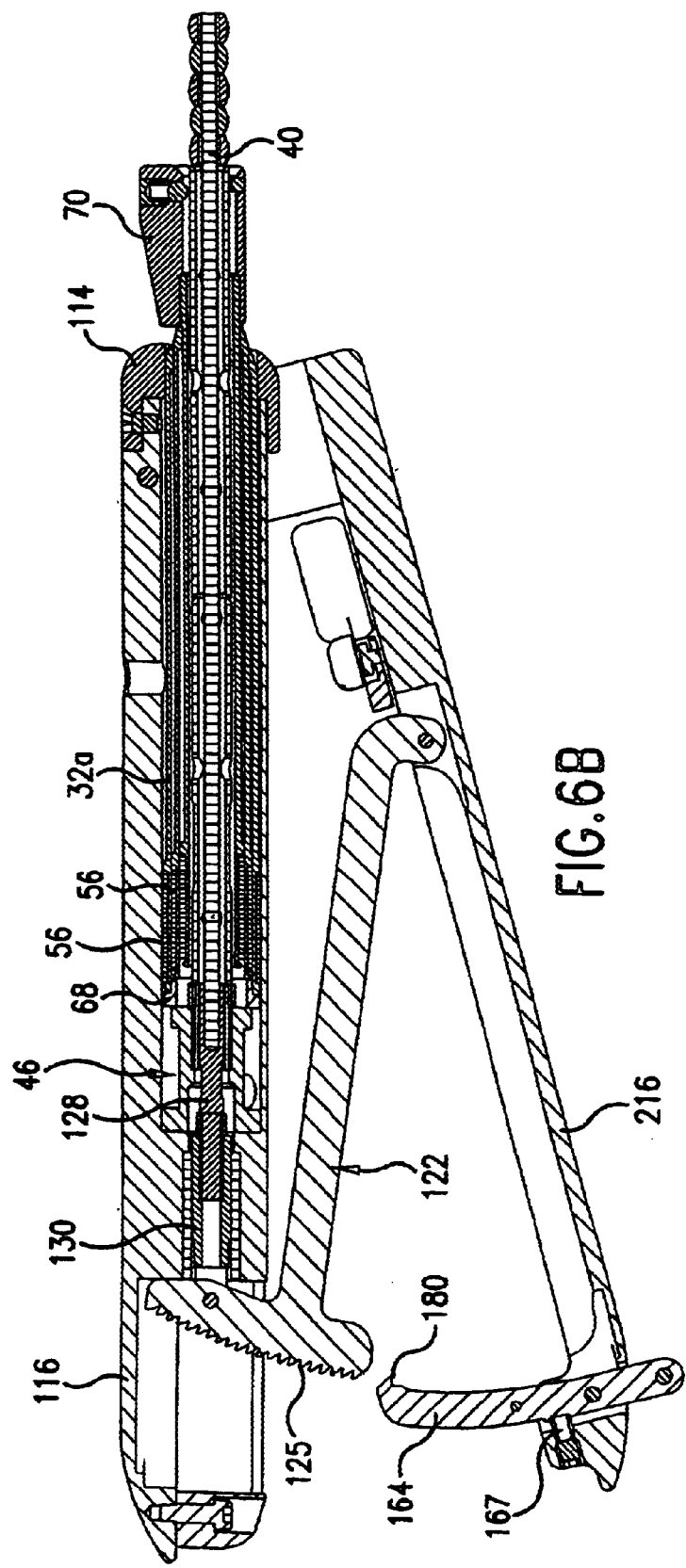
FIG. 6B is a cross-sectional view of the handle assembly of the clamp of FIG. 1 with the telescoping tubes retained inside the handle assembly.
Figure 7:
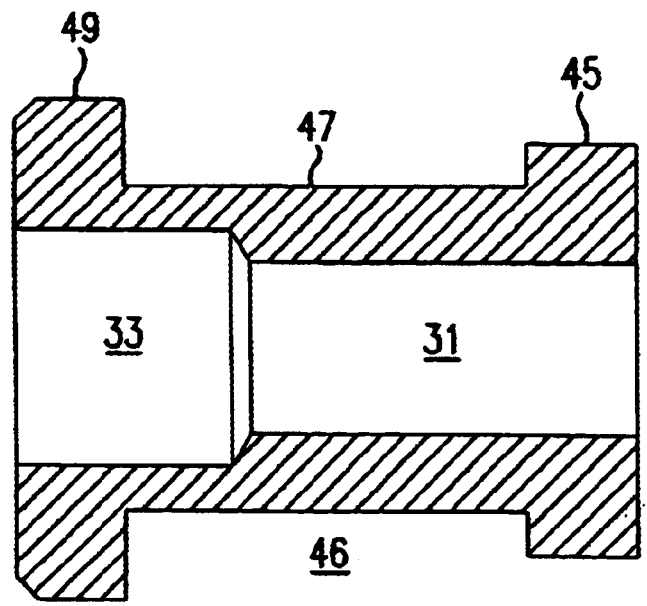
FIG. 7 is a cross-sectional view of the stop member of the clamp of FIG. 1.

The cable 40 extends through the interior of the proximal tube 42. A stop member 46 is threadably connected to the proximal end 48 of the tube 42. The stop member 46 acts as a stop member for the telescoping tubes 32, and in particular, the proximal-most telescoping tube 32a. Referring also to FIG. 7, the stop member 46 has a distal flange 45, a generally cylindrical shaft 47 and a proximal flange 49. A threaded bore 31 extends from an opening in the distal flange 45 to a central portion of the shaft 47, and a clearance hole 33 extends from an opening in the proximal flange 49 to the location where the threaded bore 31 terminates. The proximal-most end of the proximal tube 42 has external threads (not shown) which can be threadably engaged with the internal threads (not shown) inside the threaded bore 31 to couple the proximal tube 42 to the stop member 46. The proximal flange 49 acts as a stop member by abutting the proximal shoulder 137 of a bore 110 of the handle piece 116 (see FIG. 6A).

Referring to FIG. 5, a lock nut 50 can be threaded at the proximal-most end of the proximal tube 42 to secure the threaded connection between the proximal tube 42 and the stop member 46. The length of the threaded connection between the tube 42 and the stop member 46 can be adjusted by the manufacturer of the clamp 20 during the assembly of the handle assembly, simply by rotating one of the stop member 46 or the proximal tube 42 with respect to the other about the threaded connection. Adjusting the length of the threaded connection between the tube 42 and the stop member 46 allows the length of the shaft 22 to be adjusted, which in turn allows for (i) tensioning of the cable 40, and (ii) adjustment the maximum opening angle of the jaws 260, 262 of the gripping assembly 30. In this regard, the manufacturer can increase or decrease the length of the threaded connection between the tube 42 and the stop member 46 by turning stop member 46 or tube 42 with respect to each other, and then tightening the lock nut 50 to prevent the threaded connection from coming loose. When the length of the threaded connection (between the stop member 46 and the tube 42) is decreased, the stop member 46 and the tube 42 are moved away from each other, thereby increasing the length of the shaft 22. By increasing the length of the shaft 22, the length of the cable 40 that protrudes from each end of the shaft 22 is decreased. This effectively decreases the length of the cable 40 relative to the shaft 22, which increases the maximum tension in the cable 40 and decreases the maximum opening angle of the jaws of the gripping assembly 30. Similarly, by increasing the length of the threaded connection, the stop member 46 and the tube 42 are moved towards each other, thereby decreasing the length of the shaft 22. This effectively increases the length of the cable 40 relative to the shaft 22, which decreases the maximum tension in the cable 40 and increases the maximum opening angle of the jaws of the gripping assembly 30.

A plurality of telescoping tubes 32 can be used to provide rigidity to the beaded shaft 22. Each telescoping tube 32 has an inner bore 52. Any number of telescoping tubes 32 can be provided, and according to one embodiment of the present invention, one to five telescoping tubes 32 are provided. Each telescoping tube 32 can have any desired cross-section (e.g., circular, square, rectangular or elliptical, among others), and is preferably made from a substantially rigid material, such as plastic, aluminium, titanium and stainless steel, among others. The proximal-most telescoping tube 32a has the largest diameter and largest inner bore 52, while the diameters and sizes of the inner bores 52 of the intermediate telescoping tubes 32 become progressively smaller until the distal-most telescoping tube 32b, which has the smallest diameter and smallest inner bore 52. This configuration allows the plurality of telescoping tubes 32 to be nested within each other and stored inside the handle assembly 26.

Figure 8:
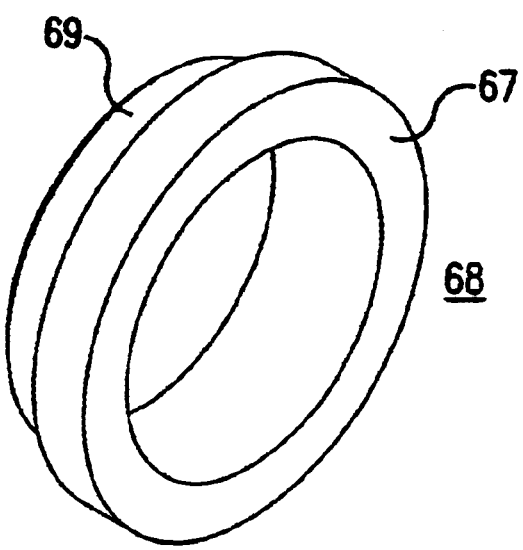
FIG. 8 is an isolated perspective view of the proximal tube bushing of the clamp of FIG. 1.
Figure 28:
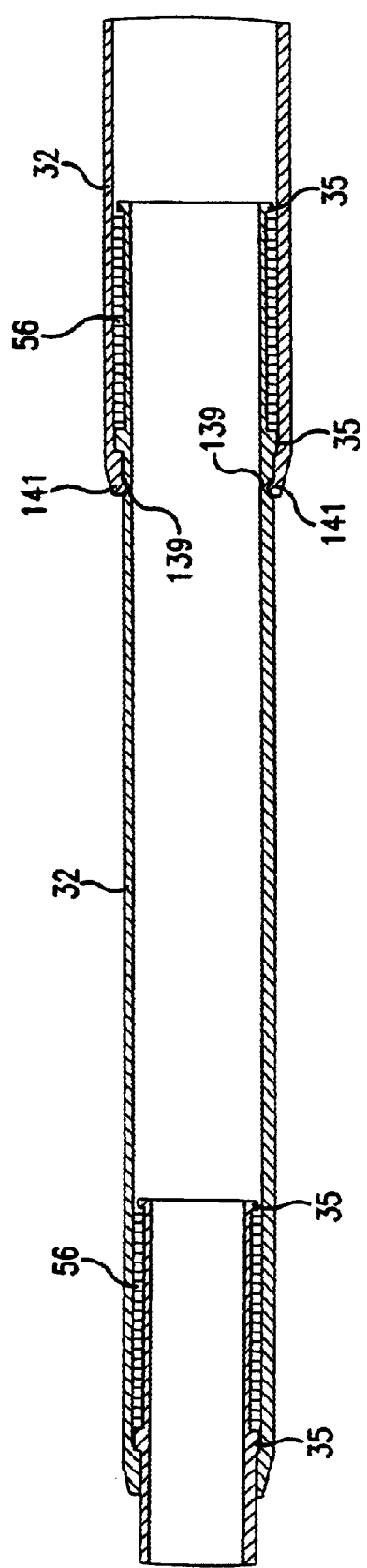
FIG. 28 is a cross-sectional view illustrating the nesting of adjacent telescoping tubes of the clamp of FIG. 1.

The telescoping tubes 32 can be locked or secured in their fully deployed configuration that is shown in FIG. 1. To accomplish this, the outer surface of each tube 32 can be provided with one or more dimples 139 that are positioned to engage corresponding locking tabs 141 that are provided at the distal end of each of the tubes 32. See FIG. 28. The distal-most tube 32b does not need to have a tab 141. Each tab 141 can be slid back and forth along the outer surface of the smaller adjacent tube 32 as the two adjacent tubes 32 reciprocate with respect to each other, and can be clicked into the corresponding dimple 139 during this sliding motion. The tab 141 can be compliant enough so that a sufficiently large axial force will disengage the tab 141 from the corresponding dimple 139 for further sliding motion. Each telescoping tube 32 also has an internal bushing 56 (see FIGS. 6B and 28) that is provided on the outer surface at the proximal end of each telescoping tube 32. Each bushing 56 is cylindrical in nature and is retained for sliding movement between the outer surface of the smaller tube 32 and the inner surface of the adjacent larger tube 32. The proximal end of each telescoping tube 32 is provided with a pair of bosses 35 that capture (axially) the bushing 56 that couples an adjacent telescoping tube 32 when the telescoping tubes 32 are withdrawn. Referring to FIGS. 6A, 6B and 8, a proximal stop member 68 is attached (e.g., by glue, screws, brazing or welding) to the proximal-most telescoping tube 32a to act as a stop member for the adjacent (and smaller-diameter) telescoping tube 32. The proximal stop member 68 has a generally circular proximal surface 67 that abuts against the distal flange 45 of the stop member 46 when all the telescoping tubes 32 are withdrawn and retained inside the handle assembly 26. A narrow-diameter flange 69 extends from the distal side of the proximal stop member 68 and is adapted to be pressed into the inner diameter at the proximal end of the proximal-most telescoping tube 32a. The outer diameter of the proximal stop member 68 is sized to allow the proximal stop member 68 to slide inside a bore 110 of the handle piece 116 (see FIGS. 6A and 6B) that is described in greater detail hereinbelow.

The bushings 56 function to promote smooth sliding of the telescoping tubes 32 within each other, and to promote stiffness to the region of the shaft 22 when the shaft 22 is completely covered by the telescoping tubes 32. With respect to the promotion of the smooth sliding of the telescoping tubes 32 within each other, the bushings 56 can be made of a harder or softer stainless steel than the telescoping tubes 32, or can be made from plastic. The smooth sliding of the telescoping tubes 32 will be achieved by the smooth surface finish of the bushings 56 and the telescoping tubes 32. If the bushings 56 are made of plastic, the smooth sliding will also be achieved by the low coefficient of friction between the telescoping tubes 32 and the bushings 56. With respect to the promotion of stiffness, the overlap between the ends of adjacent telescoping tubes 32 functions to counter any side-load or moment applied to the jaws 260, 262 of the gripping assembly 30.

Figure 27:
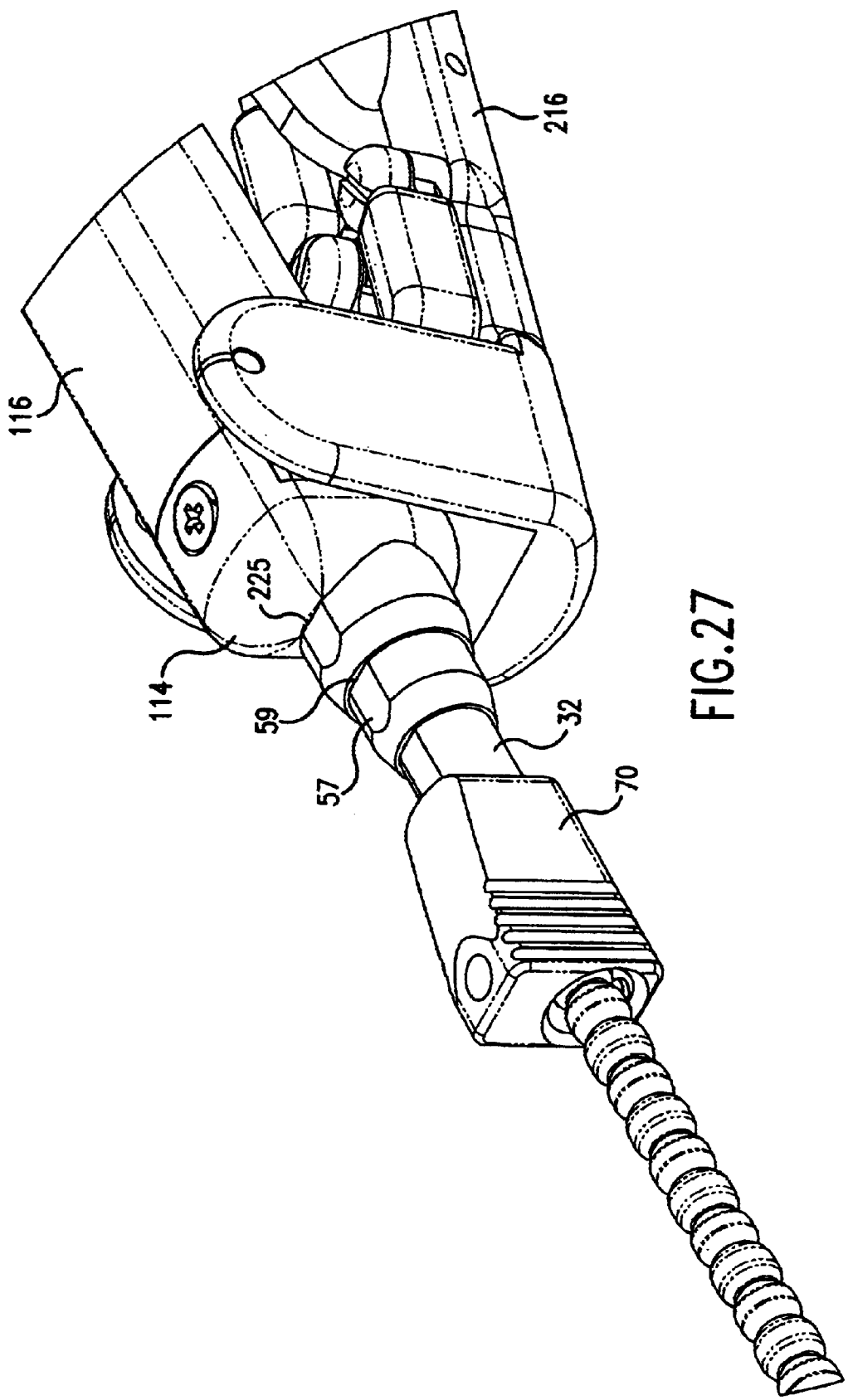
FIG. 27 is an enlarged sectional perspective view of the proximal part of the shaft of the clamp of FIG. 1.

If the cross-section of the telescoping tubes 32 is round, then a flat or curved (e.g., concave) surface (e.g., see 57 in FIGS. 1, 5 and 27) can be machined or otherwise provided on the outer surface of each telescoping tube 32, and another corresponding flat or curved surface 59 may be machined in the inner surface of the bore 52 of each telescoping tube 32 to guide the corresponding surface 57 of the adjacent telescoping tube 32. This mating correspondence between the surfaces 57 and 59 will prevent the telescoping tubes 32 from rotating with respect to each other when the shaft 22 is torqued during use of the clamp 20. The surfaces 57 and 59 function like keyways so that the surface 59 on the inner surface of the bore 52 can ride along the surface 57 on the outer surface of the adjacent and smaller telescoping tube 32.

The Handle Assembly

The handle assembly 26 is best illustrated in FIGS. 1, 2, 4, 5, 6A, 6B and 15. The handle assembly 26 has a pivoting elongated handle piece 216, and a stationary handle piece 116 that includes a cylindrical tube 54 having a bore 110 extending therethrough. A ratchet assembly is provided between the handle pieces 116, 216 for locking the jaws 260, 262 of the gripping assembly 30 at varying degress of clamping force.

Figure 16:
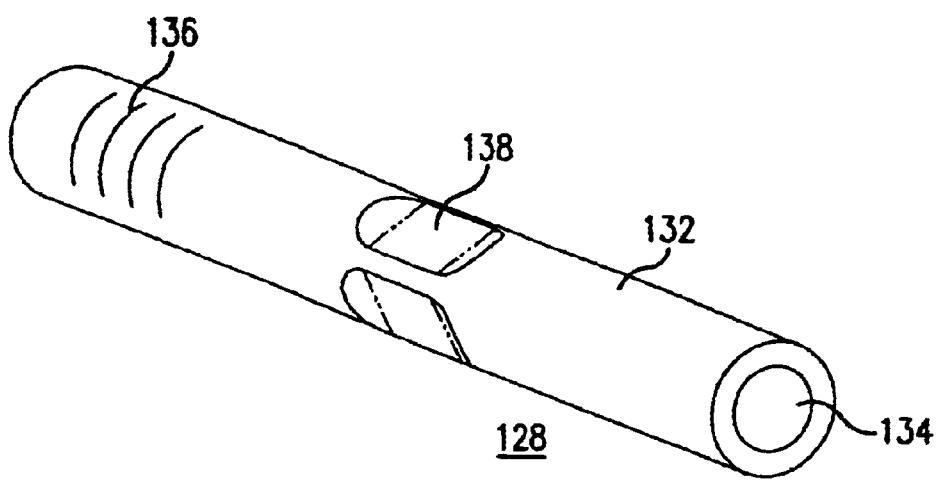
FIG. 16 is a perspective view of the cable holder of the handle assembly of the clamp of FIG. 1.

The handle assembly 26 houses a cable terminator assembly that comprises a cable holder 128 and an adjuster piece 130. FIG. 16 provides an isolated view of the cable holder 128, which has a generally cylindrical body 132 having a bore 134 that extends from its distal end to a location inside the body 132 between the distal and proximal ends of the body 132. The proximal-most end of the cable 40 is secured (e.g., by brazing or crimping) inside the bore 134. External threads 136 can be provided on the outer surface of the cable holder 128 adjacent its closed proximal end. One or more flat regions 138 can be provided on the outer surface of the cable holder 128 to facilitate convenient gripping (e.g., by a wrench) when the cable holder 128 is being threadably connected to the adjuster piece 130.

Figure 17:
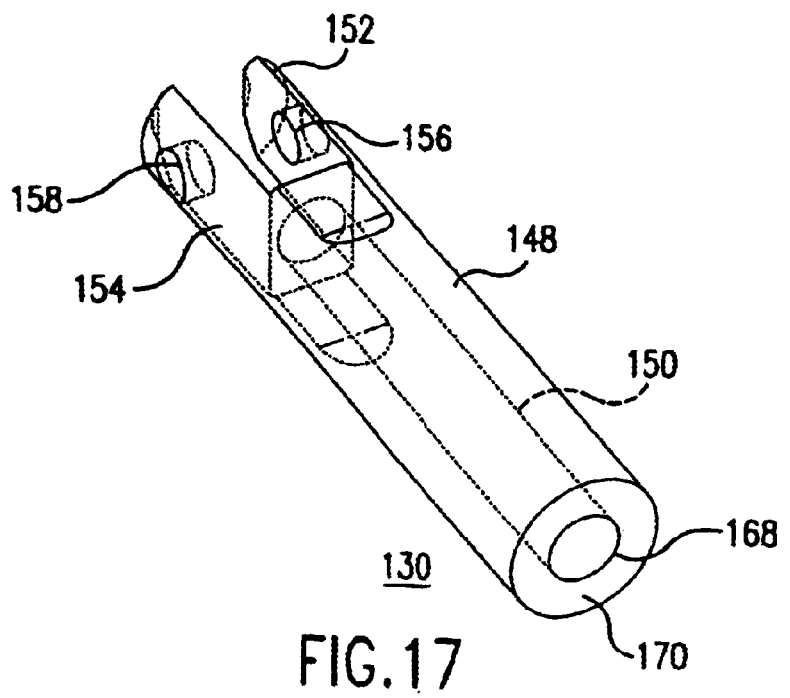
FIG. 17 is a perspective view of the adjuster piece of the handle assembly of the clamp of FIG. 1.

FIG. 17 provides an isolated view of the adjuster piece 130, which has a generally cylindrical body 148 having a threaded bore 150 extending therethrough. Two opposing walls 152 and 154 extend from the proximal end of the cylindrical body 148 to define an internal space therebetween. Each wall 152 and 154 has an opening 156 and 158, respectively, that are aligned with each other and through which a pin 160 can be extended (see FIG. 6A). The internal space between the walls 152, 154 is adapted to receive (in a pivoting connection) the transverse piece 124 of a ratchet rack 122, with the pin 160 inserted through the openings 156, 158, and an aligned opening 157 in the transverse piece 124 (see FIG. 15) to create a pivoting connection between the transverse piece 124 and the adjuster piece 130. The proximal end of the cable holder 128 is inserted into the bore 150 of the adjuster piece 130 via an opening 168 in the distal face 170 of the adjuster piece 130. The external threads 136 on the cable holder 128 threadably engage the internal threads in the bore 150 to secure the cable holder 128 to the adjuster piece 130.

In addition to adjusting or calibrating the maximum tension in the cable 40 and the maximum opening angle of the jaws 260, 262 of the gripping assembly 30 by adjusting the length of the shaft 22 (as described above), the maximum tension in the cable 40 and the maximum opening angle of the jaws 260, 262 of the gripping assembly 30 can also be adjusted or calibrated by changing the length of the cable 40 directly. The maximum tension of the cable 40 and the maximum opening angle of the jaws 260, 262 of the gripping assembly 30 can be adjusted or calibrated by turning the adjuster piece 130 when the pin 160 does not couple the adjuster piece 130 to the transverse piece 124. For example, when the pin 160 is removed from the openings 156, 158 and 157, the transverse piece 124 can be separated from the adjuster piece 130. This can only be done by the manufacturer. By rotating the adjuster piece 130, the threads 136 on the cable holder 128 translate in the threaded bore 150 to either increase or decrease the length of the cable 40 (depending on the direction of rotation). By decreasing the length of the cable 40, the jaws 260, 262 of the gripping assembly 30 close slightly, and the maximum force that the cable 40 can transmit to the jaws 260, 262 is increased. By increasing the length of the cable 40, the jaws 260, 262 open slightly, and the maximum force that the cable 40 can transmit to the jaws 260, 262 is decreased.

Referring to FIG. 6A, the handle assembly 26 further houses a plastic bushing 178 that is cylindrical in configuration and has a hollow bore through which the adjuster piece 130 can slide in a reciprocal manner. The plastic bushing 178 functions to allow the adjuster piece 130 to slide smoothly therethrough, and also prevents wear and tear between the adjuster piece 130 and the handle piece 116.

Figure 18:
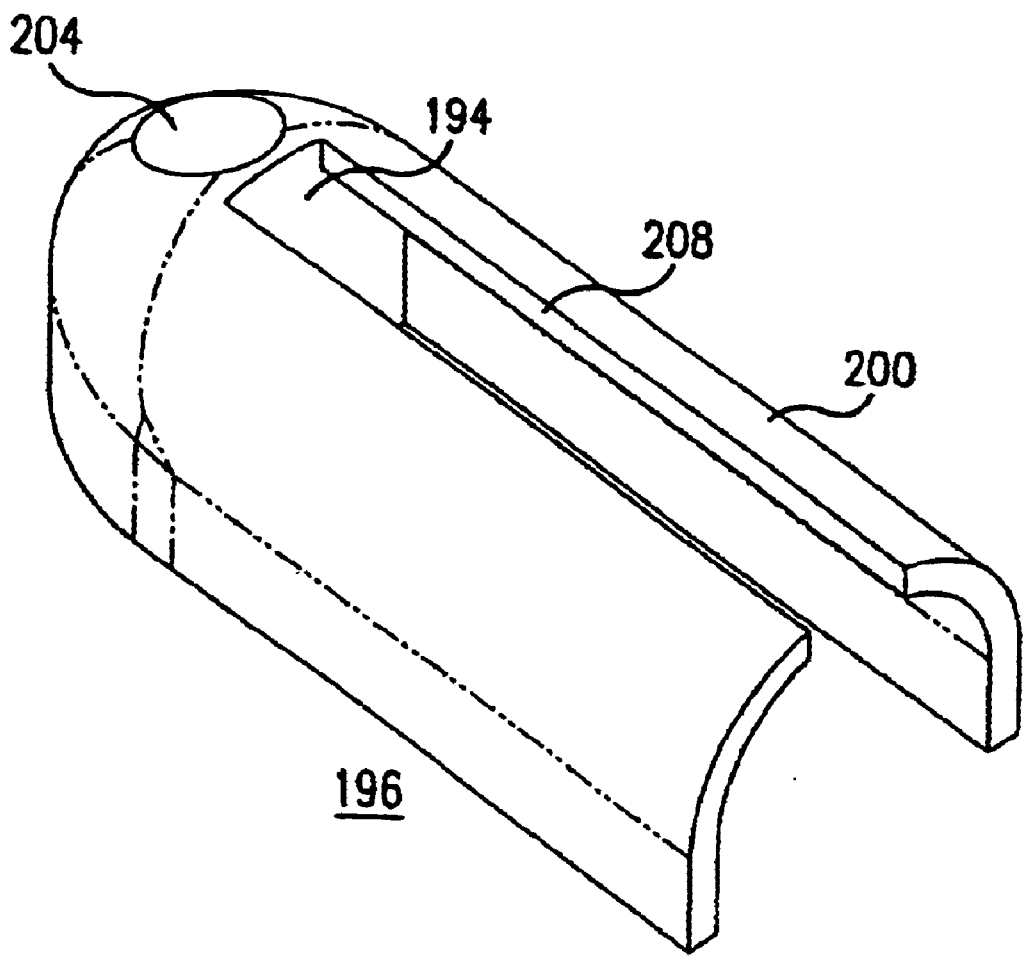
FIG. 18 is a perspective view of the end housing of the handle assembly of the clamp of FIG. 1.

As shown in FIG. 6A, an end housing 196 is attached to the proximal end 198 of the handle piece 116. FIG. 18 provides an isolated view of the end housing 196, which has a solid section 194 and a groove section 200. A longitudinal slit 208 is provided along the bottom of the groove section 200 to allow the transverse piece 124 to reciprocate therewithin. The solid section 194 of the end housing 196 has one through-hole 204 through which a threaded screw 206 can be inserted to connect the end housing 196 to a corresponding threaded opening 207 at the proximal end 198 of the handle piece 116.

Figure 19:
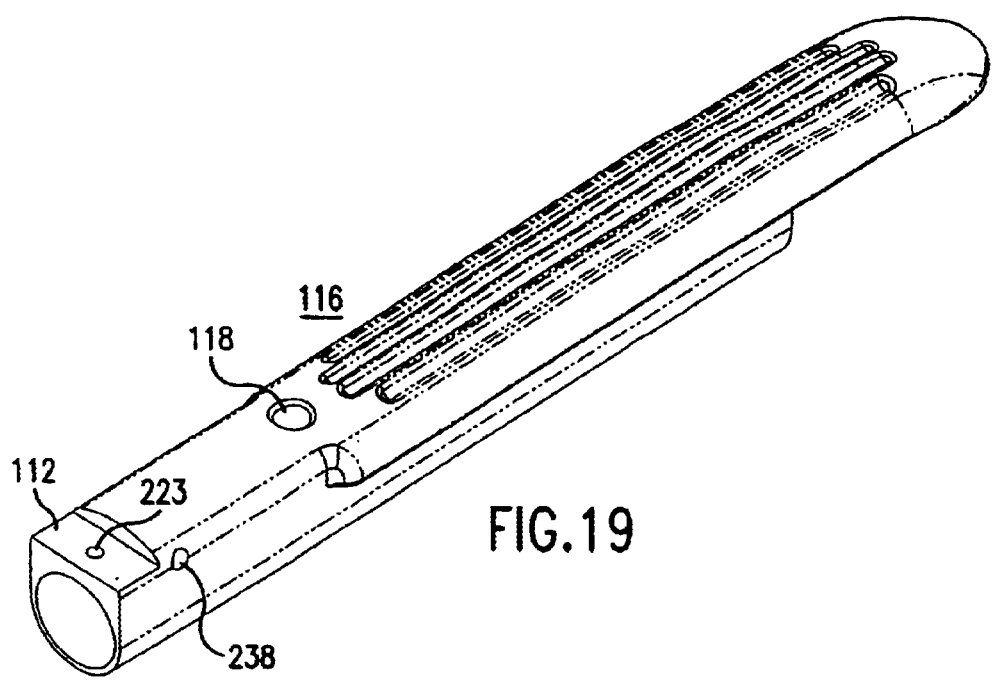
FIG. 19 is a perspective view of one handle piece of the handle assembly of the clamp of FIG. 1.

FIG. 19 provides an isolated top perspective view of the handle piece 116. Referring to FIGS. 6A and 19, the handle piece 116 has a cut-away section 112 at its distal end for receiving the upper boss 213 of a handle end piece 114. A flush port 118 is provided on the handle piece 116 to allow for cleaning of the components housed inside the handle piece 116 and its bore 110. A slot 120 is provided on the underside of the handle piece 116 adjacent its proximal end to provide clearance for the transverse piece 124 of the ratchet rack 122.

Figure 20:
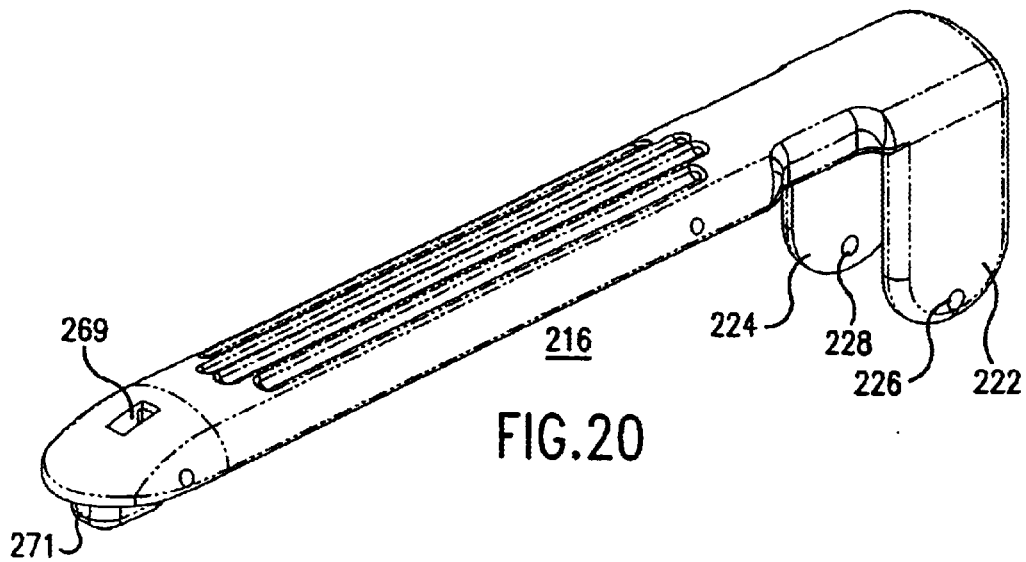
FIG. 20 is a perspective view of another handle piece of the handle assembly of the clamp of FIG. 1.

FIG. 20 provides an isolated bottom perspective view of the handle piece 216. Referring to FIGS. 6A, 15 and 20, the handle piece 216 has a longitudinal channel 218 provided on its inner surface 220. Two opposing walls 222 and 224 extend from the distal end of the handle piece 216 to define an internal space therebetween. Each wall 222 and 224 has a first opening 226 and 228, respectively, that are aligned with each other and through which a first pin 230 can be extended. The internal space between the walls 222, 224 is adapted to receive the body of the handle piece 116, with the first pin 230 inserted through the first openings 226, 228, and an aligned opening 238 (see FIG. 19) in the handle piece 116 to create a pivoting connection between the handle pieces 116 and 216. The longitudinal channel 218 is adapted to receive the ratchet rack 122 when the handle pieces 116 and 216 are gripped together (i.e., closed).

Referring to FIGS. 6A and 15, the ratchet assembly includes a ratchet 164 and a ratchet rack 122 that are removably engageable to allow the handle pieces 116, 216 to be closed, or to be locked at a desired angle with respect to each other. The ratchet rack 122 has a transmission link 123 and a transverse piece 124 at the proximal end of the link 123. The transverse piece 124 has a plurality of teeth 125 provided on its proximal-facing surface. A hooked end 126 extends from the distal end of the link 123, and has a hole 127. The hooked end 126 is retained in a narrowed channel 129 that extends from the distal end of the longitudinal channel 218 in the handle piece 216. An opening 131 extends through the side wall of the handle piece 216 from the exterior into the narrowed channel 129, and a pin 133 extends through the opening 131 and the hole 127 in the ratchet rack 122 to provide a pivoting connection between the ratchet rack 122 and the handle piece 216. A set screw 135 can be provided to secure the pin 133 in the openings 127 and 131.

The ratchet 164 essentially comprises a vertical piece that has two small and rounded handles 165 provided on either side at its bottom. The handles 165 can be used by the surgeon to disengage the ratchet 164 from the ratchet rack 122. The ratchet 164 has a first counterbore 166 in its proximal face which is adapted to receive a spring 167. The ratchet 164 also has a second counterbore 169 extending through its side wall for receiving a hooked proximal end 171 of a transmission rod 173. The ratchet 164 also has an opening 174 extending through its side wall for receiving a dowel pin 175 that also extends through an opening 176 in the side wall of the handle piece 216. Set screws 177 and 179 can be provided for securing the spring 167 and the dowel pin 175, respectively. In addition, a ratchet tooth 180 is provided at the upper end of the ratchet 164 in the distal-facing direction, and is adapted to engage one of the teeth 125 on the ratchet rack 122. The ratchet 164 extends vertically through a hole 269 in the handle piece 216, and the spring 167 extends into another hole 271 in the handle piece 216 that is transverse to the hole 269. In other words, the paths of the holes 269 and 271 are perpendicular to each other. The spring 167 naturally biases the upper end of the ratchet 164 towards the ratchet rack 122 about the pivot point defined by the dowel pin 175, so that the tooth 180 can be made to engage a selected tooth 125.

The transmission rod 173 has a hooked proximal end 171 that is pivotably coupled to the ratchet 164 at the opening 169. The distal end of the rod 173 is coupled, such as by a threaded connection, to a threaded bore (not shown) in a gimble 182. By threading the rod 173 further in or out of the threaded bore in the gimble 182, the angle of the ratchet 164 with respect to the handle piece 216 can be fine-tuned for optimal engagement between the teeth 180 and 125. The gimble 182 has a boss 183 that extends from the bottom surface of the gimble 182.

Referring to FIGS. 15 and 24–26, the ratchet assembly further includes a first ratchet release button 184 and a second ratchet release button 185 that operate in conjunction with the gimble 182 and the transmission rod 173 to release the engagement of the ratchet 164 with the ratchet rack 122.

Figure 21:
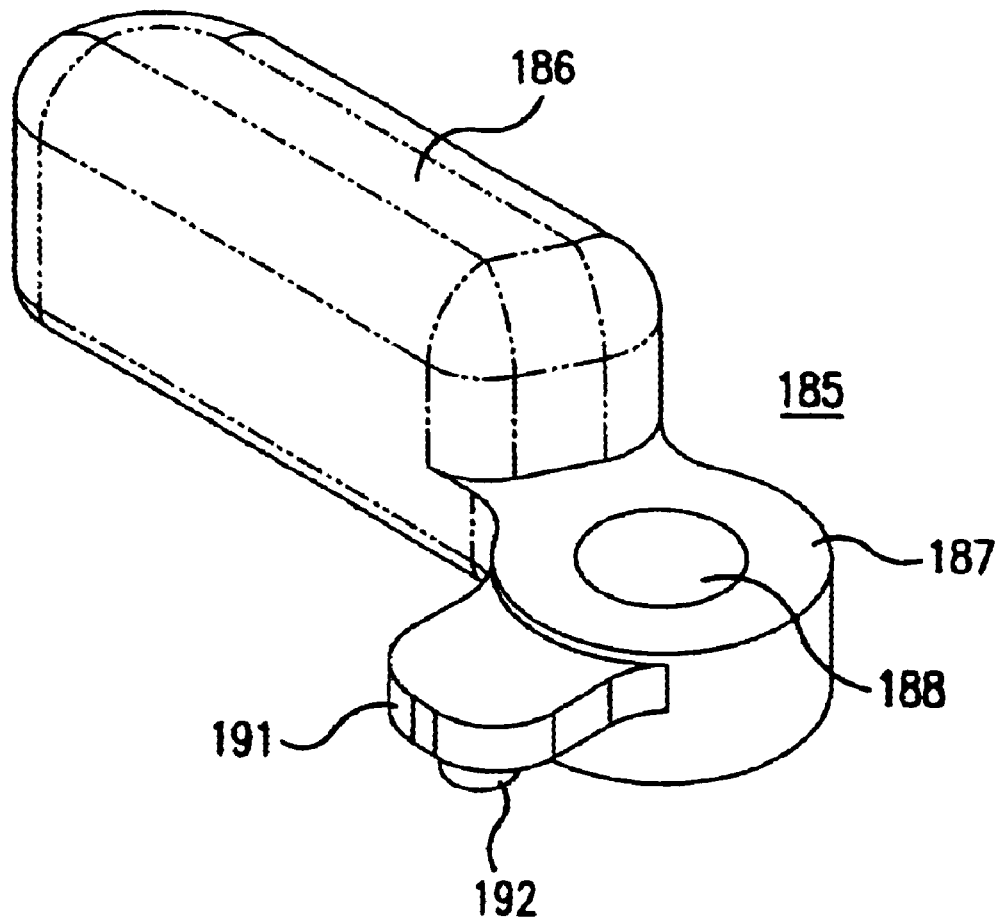
FIG. 21 is a perspective view of a ratchet release button of the handle assembly of the clamp of FIG. 1.

FIG. 21 provides an isolated perspective view of the second ratchet release button 185, which has a handle block 186 with a circular boss 187. A hole 188 is provided in the circular boss 187 through which a shoulder screw 189 can be inserted and threadably coupled to a threaded hole 190 on the inner surface 220 of the handle piece 216. An extension 191 extends at an angle from the boss 187, and carries a pin 192 at its bottom surface. The second ratchet release button 185 can be pivoted with respect to the handle piece 216 about a pivot point defined by the shoulder screw 189 and the hole 188.

Figure 22:
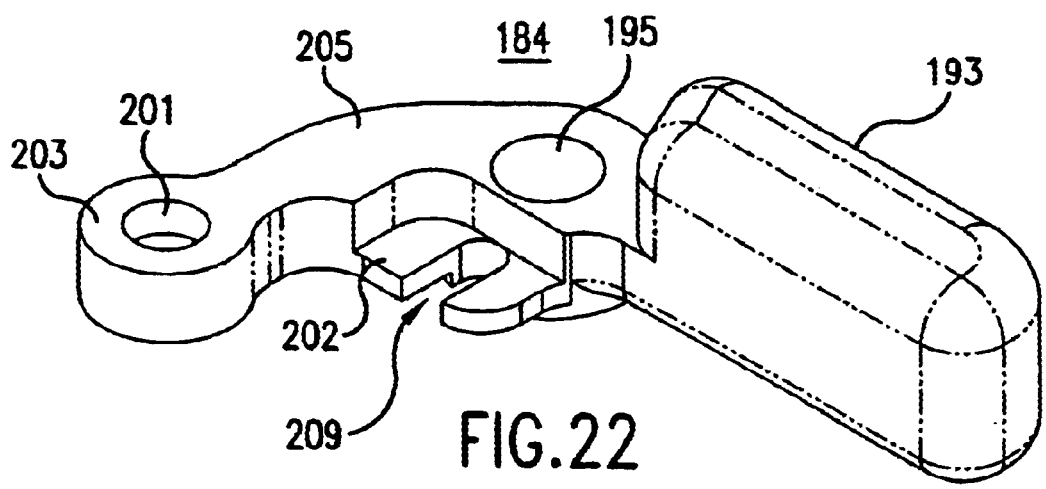
FIG. 22 is a perspective view of another ratchet release button of the handle assembly of the clamp of FIG. 1.

FIG. 22 provides an isolated perspective view of the first ratchet release button 184, which has a handle block 193 with a curved shoulder piece 205 extending at an angle from the handle block 193. A first hole 195 is provided in the shoulder piece 205 adjacent the handle block 193, and is adapted to receive a shoulder screw 197 which can be inserted therethrough and threadably coupled to a threaded hole 199 on the inner surface 220 of the handle piece 216. A circular boss 203 extends from the shoulder piece 205 at an angle from the handle block 193 and the first hole 195, and a second hole 201 is provided in the circular boss 203 through which the boss 183 from the gimble 182 can be inserted. An offset shelf 202 extends from the shoulder piece 205, and has a slot 209 that receives the pin 192 from the second ratchet release button 185. The first ratchet release button 184 can be pivoted with respect to the handle piece 216 about a pivot point defined by the shoulder screw 197 and the hole 195. In addition, the gimble 182 can be pivoted with respect to the first ratchet release button 184 about a pivot point defined by the boss 183 and the hole 201. A screw 211 (see FIG. 26) secures the boss 183 of the gimble 182 to the hole 201.

Figure 23:
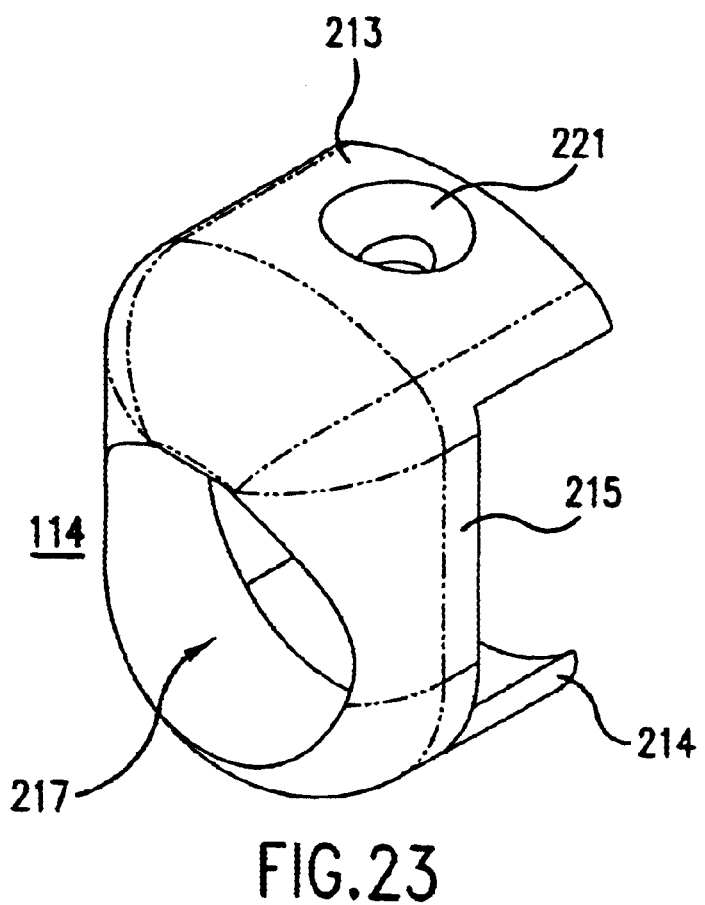
FIG. 23 is a perspective view of a handle end piece of the handle assembly of the clamp of FIG. 1.

FIG. 23 provides an isolated perspective view of a handle end piece 114, which has an upper boss 213 and a lower boss 214 that extend from a cylindrical section 215. The cylindrical section 215 has a bore 217 in which the proximal-most telescoping tube 32a can be retained. The upper boss 213 is attached to the cut-away section 112 of the handle piece 116 by threading a screw 219 (see FIG. 6A) through an opening 221 in the upper boss 213 and a threaded hole 223 in the cut-away section 112 (see FIG. 19). The lower boss 214 is seated over the bottom surface of the handle piece 116. The handle end piece 114 also has a surface 225 that prevents the tube 32a from rotating. This surface 225 can be flat or curved (e.g., concave), or can utilize known pin and slot configurations.

The operation of the ratchet assembly is best illustrated in connection with FIGS. 6A, 15 and 24–26. There are three possible configurations for the ratchet assembly. In all configurations, it should be noted that the spring 167 always biases the tooth 180 of the ratchet 164 in the distal direction towards the ratchet rack 124.

Figure 24:
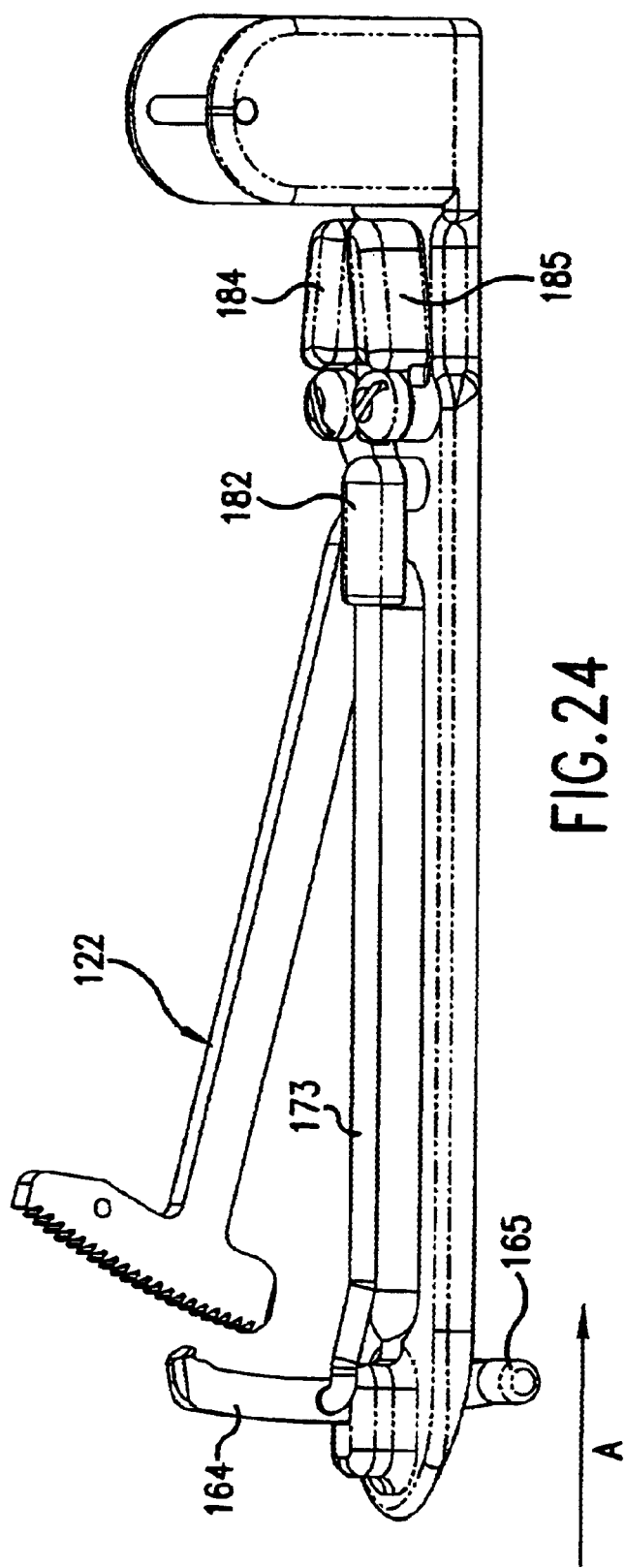
FIG. 24 is side perspective view of portions of the handle assembly of the clamp of FIG. 1 showing the ratchet disengaged from the ratchet rack.

In a first configuration, the teeth 125 and 180 of the ratchet rack 122 and the ratchet 164, respectively, do not engage each other. This is shown in FIG. 24. When in this opened position, the free ends of the handle blocks 193 and 186 of the first and second ratchet release buttons 184 and 185, respectively, are generally pointed at each other at an angle.

In a second configuration, the handle pieces 116, 216 are opened, thus the teeth 125 and 180 of the ratchet rack 122 and the ratchet 164, respectively, do not engage each other, and the tooth 180 on the ratchet 164 extends in a distal direction past the teeth 125 on the ratchet rack 122. This is shown in FIG. 6A. When in this position, the free ends of the handle blocks 193 and 186 of the first and second ratchet release buttons 184 and 185, respectively, exactly parallel to each other because the bias of the spring 167 causes the boss 203 of the first ratchet release button 184 to contact the boss 187 of the second ratchet release button 185.

Figure 25:
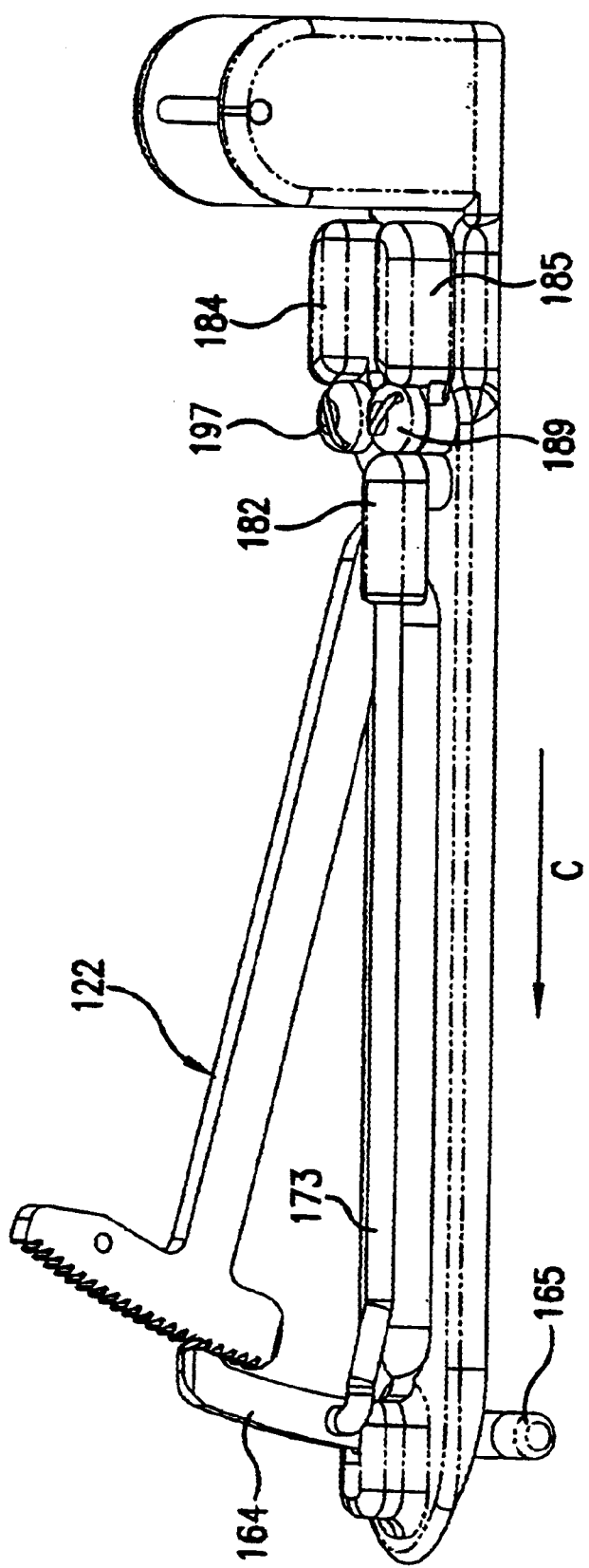
FIG. 25 is a side perspective view of portions of the handle assembly of the clamp of FIG. 1 showing the ratchet engaged to the ratchet rack.
Figure 26:
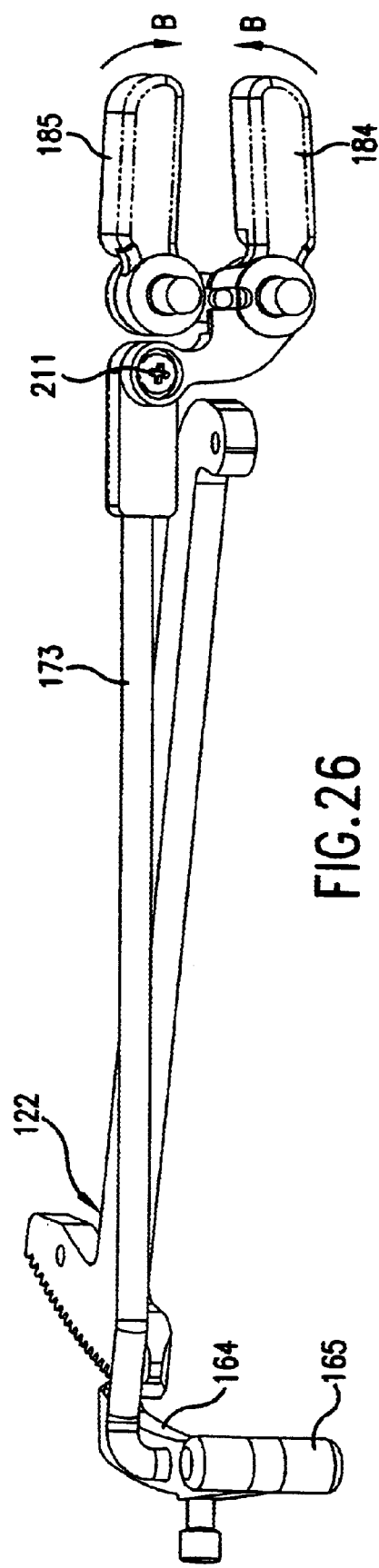
FIG. 26 is a bottom perspective view of portions of the handle assembly of the clamp of FIG. 1 showing the ratchet engaged to the ratchet rack.

In a third configuration, as the tooth 180 pivots in the distal direction (about the pivot point defined by dowel pin 175), the rod 173 and the gimble 182 are pushed in the distal direction to pivot the first ratchet release button 184 about the pivot point defined by the boss 183. The tooth 180 engages a selected tooth 125 on the ratchet rack 122. This is shown in FIGS. 25 and 26. When in this position, the free ends of the handle blocks 193 and 186 of the first and second ratchet release buttons 184 and 185, respectively, are almost, but not exactly, parallel to each other. The surgeon can lock the jaws 260, 262 at varying degrees of clamping force by selecting a different tooth 125 to be engaged with the tooth 180.

The engagement between the tooth 180 and a selected tooth 125 can be released in one or both of two ways. The surgeon can push the handles 165 in the distal direction indicated by the arrow A in FIGS. 6A and 24, thereby pivoting the ratchet 164 about the pivot point 175 so that the tooth 180 is pivoted in a direction opposite to the arrow A, which releases the engagement between the tooth 180 and a selected tooth 125. Thus, the handles 165 operate as levers to pivot the ratchet 164. Alternatively, the surgeon can press one or both of the first and second ratchet release buttons 184 and 185 towards each other in the direction of arrow B in FIG. 26. The inward pivoting motion of one or both of the ratchet release buttons 184, 185 will cause the circular boss 203 and the boss 183 to pivot in the proximal direction, thereby pushing the gimble 182 and the transmission rod 173 in a proximal direction (see arrow C in FIG. 25) to pivot the ratchet 164 about the pivot point 175 so that the tooth 180 is pivoted in a direction opposite to the arrow A, thereby releasing the engagement between the tooth 180 and a selected tooth 125.

The handle assembly 26 is normally biased to the open position that is shown in FIGS. 1 and 6A. As described above, when a user grips the two handle pieces 116 and 216 together, the pivoting at the pivot points defined by the pins 133 and 160 will push the transverse piece 124 in a proximal direction (see arrow C in FIG. 25), which in turn pulls the adjuster piece 130 and the cable housing 128 in the same proximal direction. As the cable housing 128 travels in the proximal direction, it will pull the cable 40 along with it, causing the cable 40 to be pulled in the proximal direction as well.

When the user's grip on the handle pieces 116, 216 is released, the spring 420 in the gripping assembly 30 (described in greater detail below) will bias the jaws 260 and 262 open, which will pull the cable 40 in a distal direction (i.e., opposite to arrow C), and in so doing, will also pull the handle pieces 116, 216 apart (i.e., open).

Locking Assembly for Locking Telescoping Tubes 32

FIGS. 9A–9C and 10 illustrate a locking assembly that is used to lock and secure the distal-most telescoping tube 32b to the gripping assembly 30. The locking assembly also includes an alignment mechanism that (1) guides and aligns the jaws of the gripping assembly 30 with the shaft 22 and the telescoping tubes 32, and (2) prevents the jaws 260, 262 of the gripping assembly 30 from rotating when the telescoping tubes 32 extend across the entire shaft 22 and are secured to the gripping assembly 30.

The locking assembly includes (1) a helix cylinder 58 that is secured to the gripping assembly 30, and (2) a lock housing 70 that is movable with respect to the helix cylinder 58 and which can be removably secured to the helix cylinder 58.

Figure 11A:
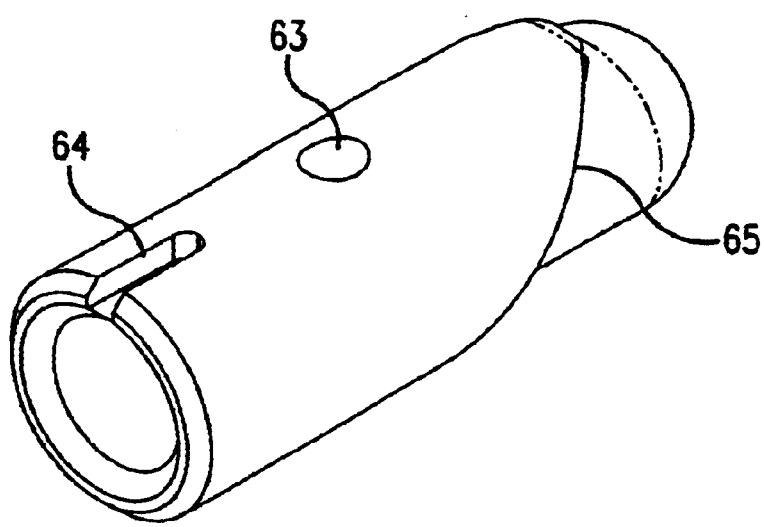
FIGS. 11A, 11B and 11C are top perspective, bottom perspective, and cross-sectional views, respectively, of the helix cylinder of the clamp of FIG. 1.
Figure 11B:
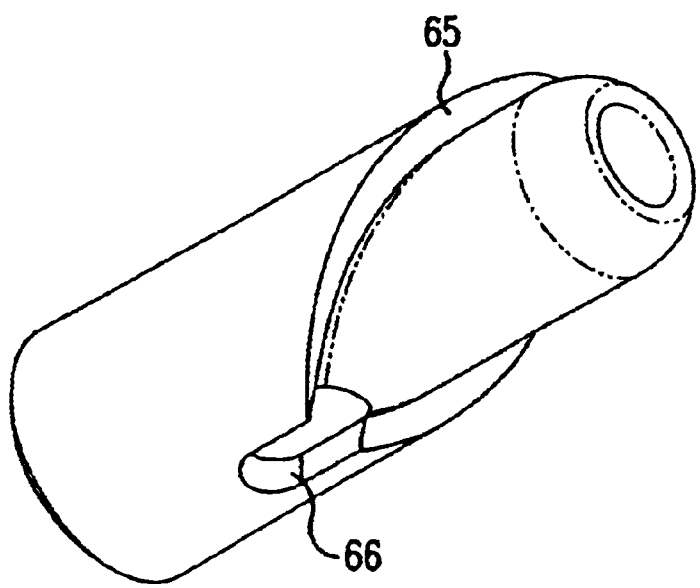
Figure 11C:
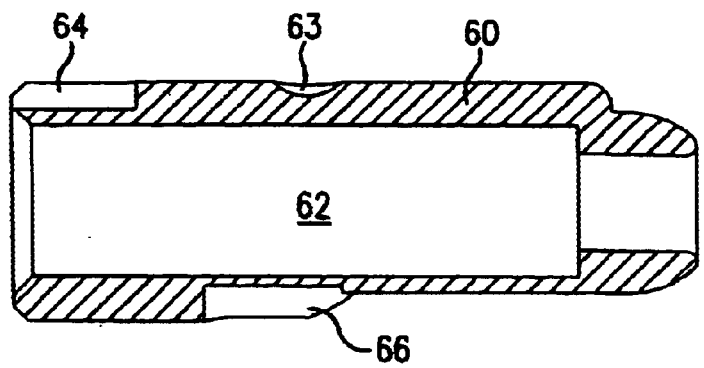

Referring to FIGS. 11A–11C, the helix cylinder 58 has a generally cylindrical body 60 having a bore 62 extending therethrough. A dimple 63 is provided on the outer surface of the body 60 for receiving the ball 87 of the lock housing 70 (as described below). A first longitudinal slot 64 extends from the distal end of the body 60 for a short distance along the body 60, and functions to align the helix cylinder 58 rotationally when the helix cylinder 58 is welded to the gripping assembly 30 (as described below). A helical shoulder 65 is provided along the outer surface of the body 60, extending helically from adjacent the proximal end of the body 60 until it terminates at a second short longitudinal slot 66 at the bottom of the body 60. A spring 420 is retained inside the bore 62 and overlies the cable 40 (which extends through the bore 62), as best shown in FIG. 9A.

Figure 9A:
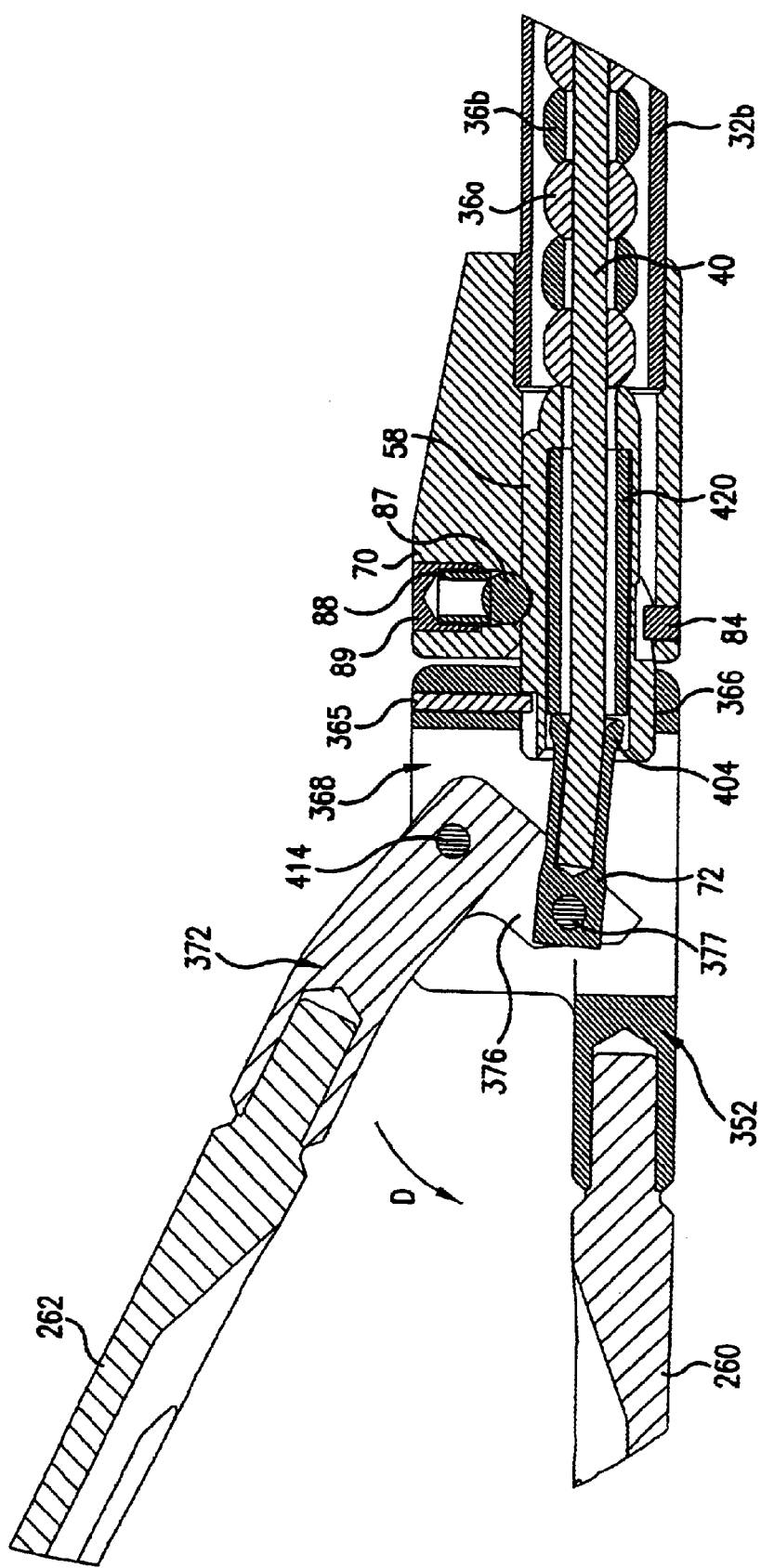
FIG. 9A is a cross-sectional view of the gripping assembly of the clamp of FIG. 1 with the jaws open and the lock mechanism locked with the helix cylinder.
Figure 9C:
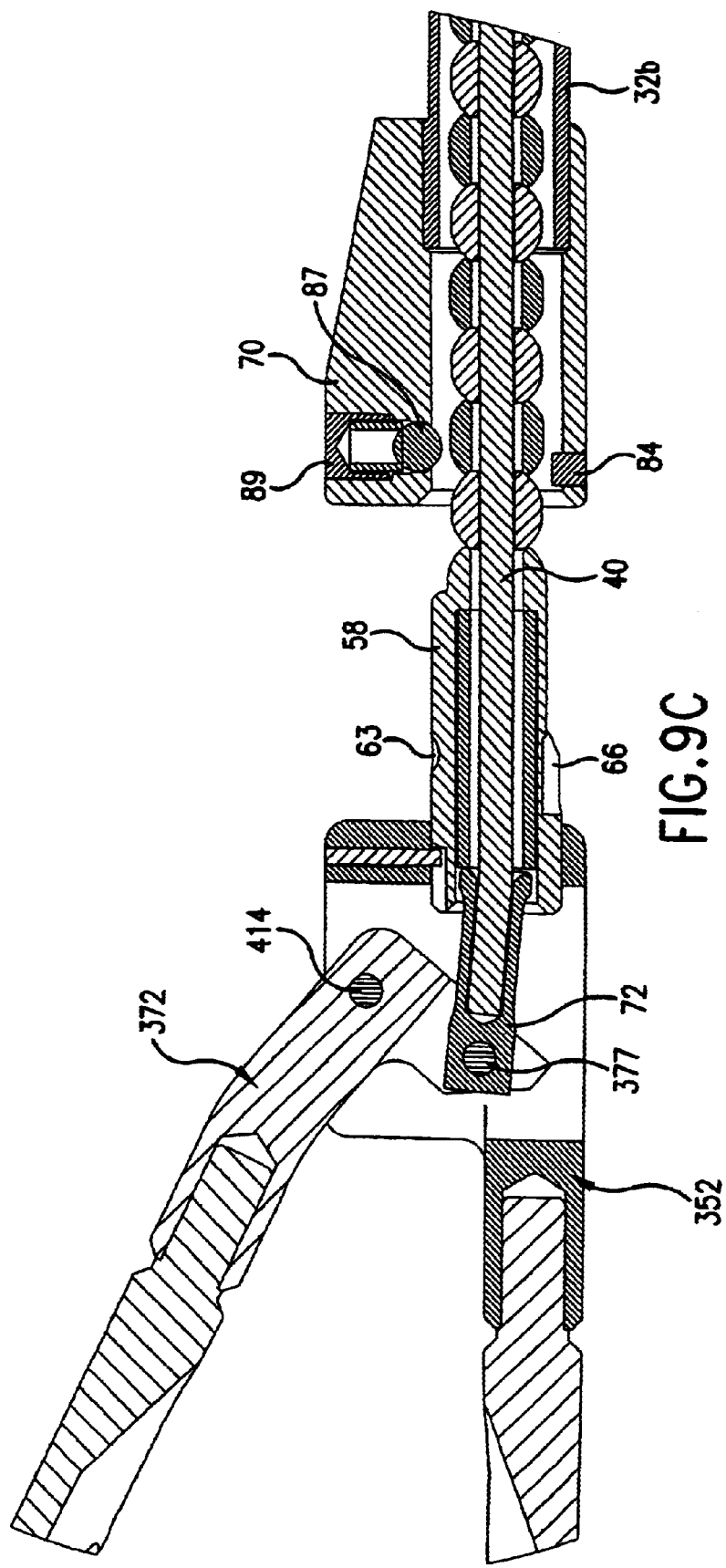
FIG. 9C is a cross-sectional view of the gripping assembly of the clamp of FIG. 1 with the jaws open and the lock mechanism disengaged from the helix cylinder.
Figure 10:
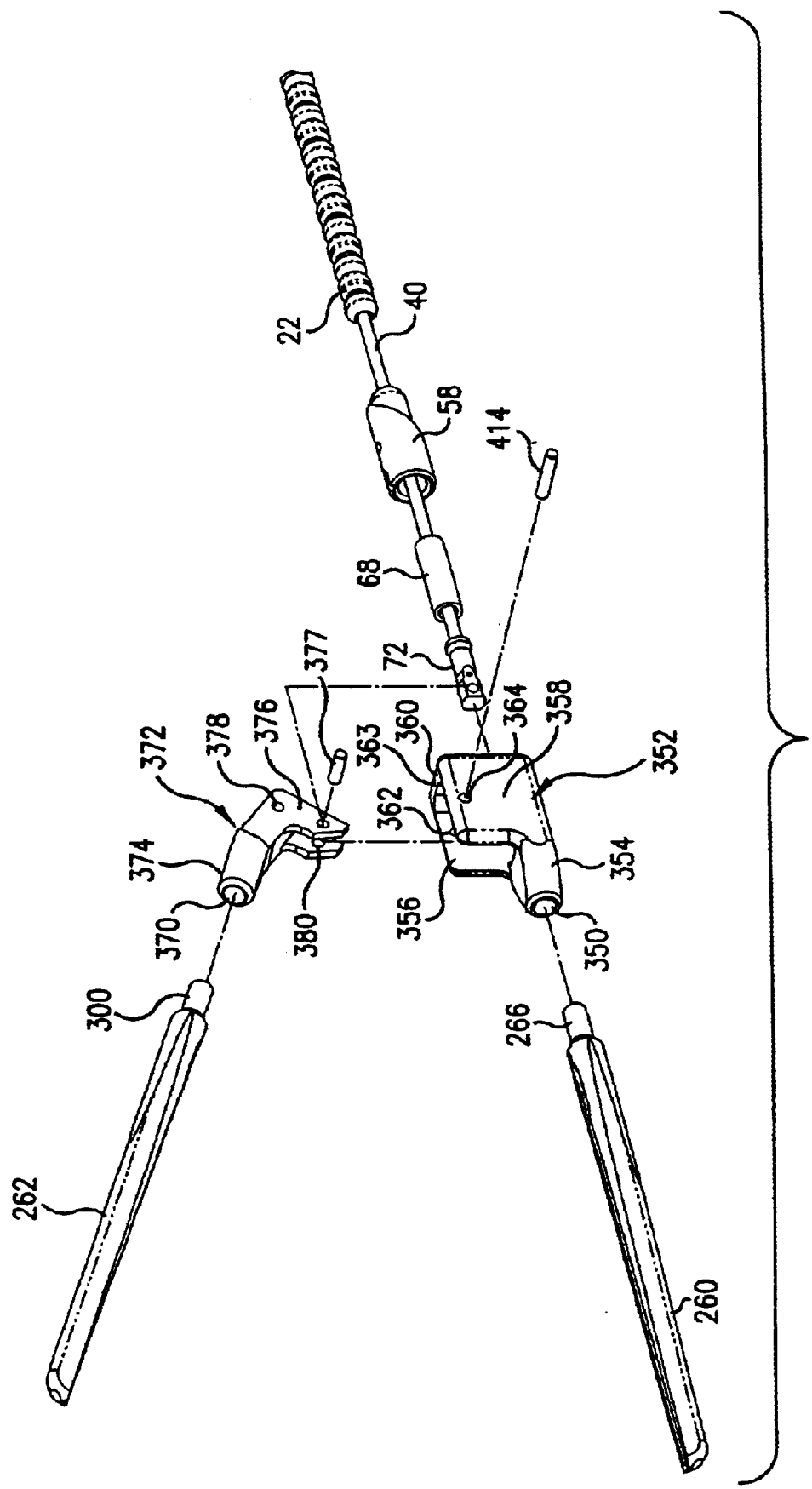
FIG. 10 is an exploded perspective view of the gripping assembly of the clamp of FIG. 1.
Figure 14A:
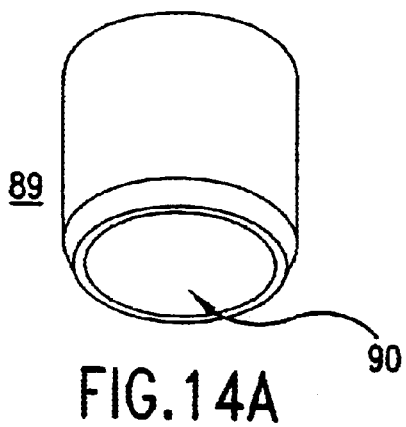
FIGS. 14A and 14B are perspective and cross-sectional views, respectively, of the dowel pin used with the lock mechanism of the clamp of FIG. 1.
Figure 14B:
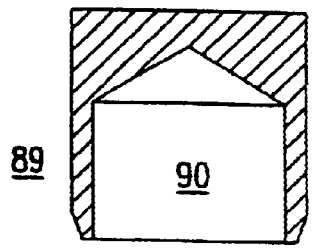

Referring now to FIGS. 2, 9A–9C and 13A–13C, the lock housing 70 is attached to the distal-most telescoping tube 32b. The lock housing 70 has a generally rectangular body 77 having a generally cylindrical throughbore that is divided into two sections, a distal section 78 and a proximal section 79 that has a larger diameter than the diameter of the distal section 78. A step 80 defines the transition from the distal section 78 to the proximal section 79. A portion of the distal-most telescoping tube 32b is adapted to be retained inside the proximal section 79, and the helix cylinder 58 is retained inside the distal section 78. The step 80 prevents the distal-most telescoping tube 32b from extending into the distal section 78. The top outer surface 81 of the lock housing 70 can be angled or slanted to provide a convenient push surface for the user's finger, and ridges 82 can be provided anywhere along the outer surface (e.g., along the outer side walls) of the lock housing 70 for gripping purposes. A bottom hole 83 extends from the outer surface of the body 77 into the distal section 78 of the throughbore, and a dowel pin 84 is received inside the hole 83. A transverse bore 85 extends from the outer surface of the body 77 into the distal section 78 of the throughbore. The transverse bore 85 has a shoulder 86 adjacent its opening into the distal section 78. As shown in FIGS. 9A–9C, a ball 87 is seated in the shoulder 86, and protrudes slightly into the distal section 78. The shoulder 86 prevents the ball 87 from falling into the distal section 78. A spring 88 is placed in the transverse bore 85 and is pressed against the ball 87 to maintain the ball 87 against the shoulder 86. Another dowel pin 89 is positioned over the spring 88 and the ball 87. Referring to FIGS. 14A and 14B, the dowel pin 89 has a interior bore 90 that retains the spring 88, with the spring 88 abutting at one end against the ball 87 and at the other end against the interior wall of the bore 90. The dowel pin 89 can be secured inside the bore 90 by screwing, pressing, brazing, gluing or welding the dowel pin 89 into the bore 90.

The parts of the ball 87 that protrude into the distal section 78 facilitate removable engagement with the dimple 63 of the helix cylinder 58 in the following manner (see FIGS. 9A–9C): when the helix cylinder 58 is inserted into the distal section 78, the body 60 of the helix cylinder 58 forces the ball 87 radially outwardly and compresses the spring 88. As the helix cylinder 58 is continued to be inserted into the distal section 78, the ball 87 will eventually become aligned with the dimple 63, at which time the natural bias of the spring 88 will force the protruding part of the ball 87 into the dimple 63 to lock the lock housing 70 at a defined position with respect to the helix cylinder 58. This combination of an outward radial force (from the body 60 of the helix cylinder 58) and an inward radial force (from the spring 88) locks the lock housing 70 to the helix cylinder 58.

Figure 12A:
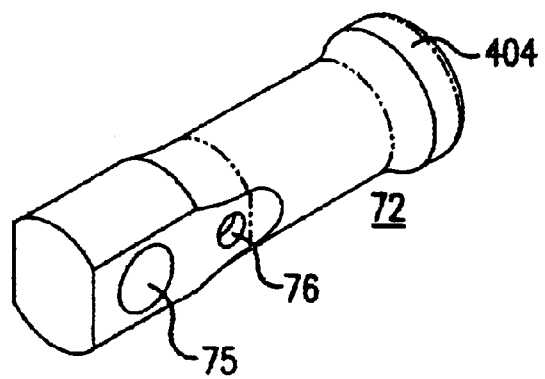
FIGS. 12A and 12B are perspective and cross-sectional views, respectively, of the cable holder in the gripping assembly of the clamp of FIG. 1.
Figure 12B:
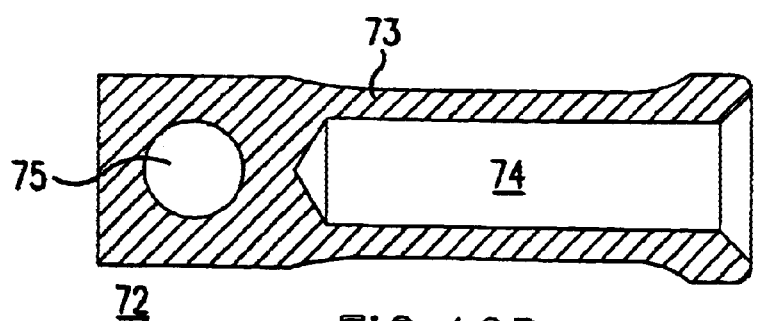
Figure 13A:
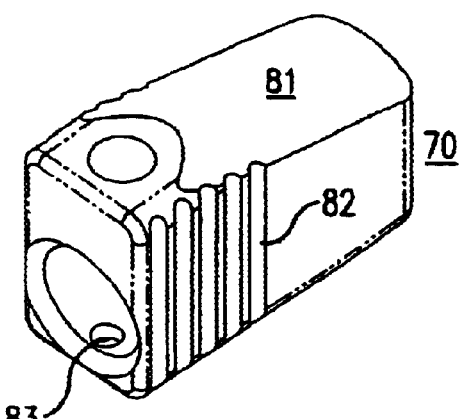
FIGS. 13A and 13B are perspective and cross-sectional views, respectively, of the lock mechanism of the clamp of FIG. 1.
Figure 13B:
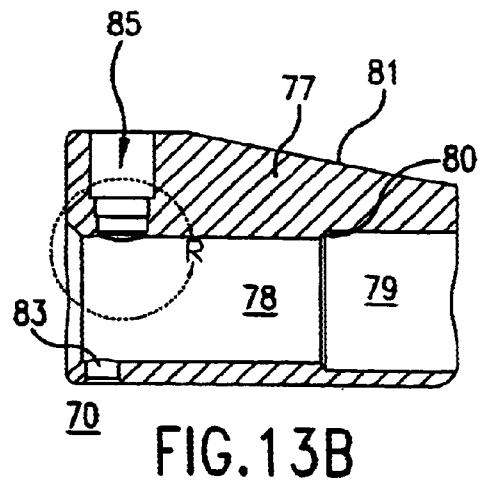
Figure 13C:
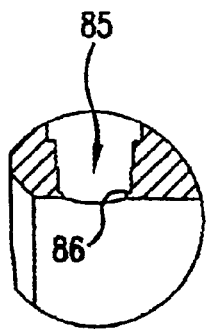
FIG. 13C is an enlarged sectional view of the region labeled R in FIG. 13B.

A portion of a cable holder 72 (that is part of the gripping assembly 30) is retained inside the bore 62 of the helix cylinder 58 and adapted for reciprocating movement in the bore 62. The cable holder 72 retains the distal-most end of the cable 40. Referring now to FIGS. 12A–12B, the cable holder 72 has a generally cylindrical body 73 having a bore 74 extending from its proximal end and terminating at about the center of the body 73. A through-hole 75 is provided adjacent the distal end of the body 73 and is adapted to receive the pin 377 of the gripping assembly 30 (as described below). A vent hole 76 can be provided in the body 73 for manufacturing purposes such as brazing, gluing or welding the cable 40.

As shown in FIGS. 9A–9C and 10, the cable 40 extends from the shaft 22 through the helix cylinder 58 (and the spring 420) and into the bore 74 of the cable holder 72. This distal-most end of the cable 40 is secured inside the bore 74 of the cable holder 72 by brazing, welding, crimping or gluing.

The lock housing 70 and the helix cylinder 58 can function to guide and align the jaws 260, 262 of the gripping assembly 30 with the shaft 22 and the telescoping tubes 32, and to prevent the jaws 260, 262 of the gripping assembly 30 from rotating when the telescoping tubes 32 extend across the entire shaft 22 and are secured to the gripping assembly 30. Referring first to FIGS. 2 and 9C, the lock housing 70 is shown as being disengaged from the helix cylinder 58, so that the lock housing 70 can be retracted together with the telescoping tube 32b that is attached to it. The lock housing 70 can be retracted proximally until it is adjacent the handle end piece 114. When it is desired to completely cover the shaft 22 with the telescoping tubes 32, the user can grip the lock housing 70 and then pull it towards the helix cylinder 58. As the lock housing 70 approaches and engages the helix cylinder 58, two events occur. First, the dowel pin 84 will contact the helical shoulder 65, and be guided by the helical shoulder 65 until the dowel pin 84 is seated inside the second slot 66, as shown in FIGS. 1 and 9A. Second, the helix cylinder 58 is inserted into the distal section 78 of the lock housing 70 until the ball 87 becomes aligned with the dimple 63, at which time the natural bias of the spring 88 will force the protruding part of the ball 87 into the dimple 63. Once both of these events have occurred, the lock housing 70 is locked at a defined position with respect to the helix cylinder 58 in a manner such that one cannot rotate with respect to the other. As a result, rotation of the jaws 260, 262 of the gripping assembly 30 can be prevented when the lock housing 70 is locked with the helix cylinder 58.

The Gripping Assembly 30

One embodiment of the gripping assembly 30 is illustrated in connection with FIGS. 9A–9C and 10. The gripping assembly 30 is used to grip tissue or other anatomical structures (such as but not limited to a blood vessel) during a surgical procedure. The gripping assembly 30 has a pair of gripping jaws 260 and 262 that can be pivoted to open and close with respect to each other. Each jaw 260 and 262 has an insert (not shown) provided thereon. These inserts can be embodied in the form of any of the known inserts that are currently commercially available. The techniques and mechanisms for securing the inserts to the jaws 260 and 262 are also well-known and will not be described herein.

The proximal end 266 of the first jaw 260 is secured inside a bore 350 of a stationary jaw base 352. The jaw base 352 has a distal tubular section 354 that defines the bore 350, a holder section that has a pair of opposing vertical walls 356 and 358, and a proximal wall section 360 that is attached to the helix cylinder 58. The opposing vertical walls 356 and 358 define a space 368 therebetween, and each vertical wall 356 and 358 has an aligned opening 362 and 364, respectively. The proximal wall section 360 has a bore 366 through which a portion of the helix cylinder 58 (and the cable 40 carried therein) can extend. A hole 363 extends from the top surface of the proximal wall section 360 into the bore 366, and a dowel pin 365 is inserted through the hole 363 and into the slot 64 of the helix cylinder 58 to secure a portion of the helix cylinder 58 in a non-rotatable and fixed position inside the proximal wall section 360. According to one embodiment, the helix cylinder 58 can be welded to the proximal wall section 360. Alternatively, the helix cylinder 58 can also be pressed, glazed, glued or screwed into the jaw base 352.

The proximal end 300 of the second jaw 262 is secured inside a bore 370 of a pivoting jaw base 372. The jaw base 372 has an L-shaped configuration, with a longitudinal portion 374 that defines the bore 370, and a transverse portion 376 that has a hole 378. The transverse portion 376 is comprised of two parallel walls that define a space therebetween, and with aligned second holes 380 provided in each parallel wall.

The cable holder 72 carries the distal end of the cable 40 and extends through the bore 366 of the jaw base 352 and into the space 368. The two parallel walls of the transverse portion 376 of the jaw base 372 also extend into the space 368. The through-hole 75 of the cable holder 72 is received in the space between the two parallel walls of the transverse portion 376, and is aligned with the openings 380 on each of these parallel walls. A pin 377 extends through the through-hole 75 and the openings 380 to create a pivoting connection between the cable holder 72 and the jaw base 372. In addition, the openings 362 and 364 in the jaw base 352 are aligned with the hole 378 of the jaw base 372, so a dowel pin 414 can extend through the openings 362, 364 and the hole 378 to create a pivoting connection between the two jaw bases 352 and 372.

As described above, the spring 420 is provided inside the helix cylinder 58, and functions to continuously bias the jaw base 372 with respect to the jaw base 352 by pushing or exerting a bias against the proximal end 404 of the cable holder 72. In particular, the bias that is exerted against the proximal end 404 of the cable holder 72 pushes the cable holder 72 in the distal direction against the pin 377 to pivot the jaw base 372 about the pin 414 in a clockwise direction opposite to the arrow D as viewed in FIG. 9A, thereby pivoting the jaw base 372 away from the jaw base 352 to open the jaws 260, 262. At the same time, movement by the cable holder 72 in the distal direction will pull the cable 40 in a distal direction, which will pull the cable holder 128, the adjuster piece 130, the pin 160, and the transverse piece 124 in the distal direction. By pulling the transverse piece 124 in the distal direction, the ratchet rack 122 pivots about the pin 133 to push the handle pieces 116 and 216 apart from each other.

To close the jaws 260, 262, the surgeon grips the handle pieces 116, 216 towards each other to overcome the bias of the spring 420. In particular, when the surgeon grips the handle pieces 116, 216, the ratchet rack 122 is pivoted about the pin 133, and the transverse piece 124 is pivoted about the pin 160, to pull the transverse piece 124 in the proximal direction. This will pull the cable holder 128 and the adjuster piece 130 in the proximal direction, so that the cable 40 carried in the cable holder 128 is also pulled in the proximal direction. When the cable 40 is pulled in the proximal direction, the distal end of the cable 40 that is secured to the cable holder 72 will also pull the cable holder 72 in the proximal direction. As the cable holder 72 moves in the proximal direction, the cable holder 72 will overcome the bias of the spring 420 (see FIG. 9B), and will rotate the transverse portion 376 of the jaw base 372 in the direction of arrow D shown in FIG. 9A about the axis defined by the pin 414. This causes the pivoting jaw base 372 to pivot towards the stationary jaw base 352 to close the jaws 260, 262 so as to grip a blood vessel, tissue or other anatomical structure.

When the jaws 260, 262 have been closed, the surgeon can retract the telescoping tubes 32 completely to nest and store all the telescoping tubes 32 inside the handle assembly 26, or the surgeon can retract some, but not all, of the telescoping tubes 32 so that only a portion (but not the entire length of) the shaft 22 is exposed. The exposed portions of the shaft 22 will then be bendable by the surgeon in any direction desired by the surgeon, so that the handle assembly 26 can be moved away from the surgical site and not impede the surgeon's access to the surgical site.

Figure 29:
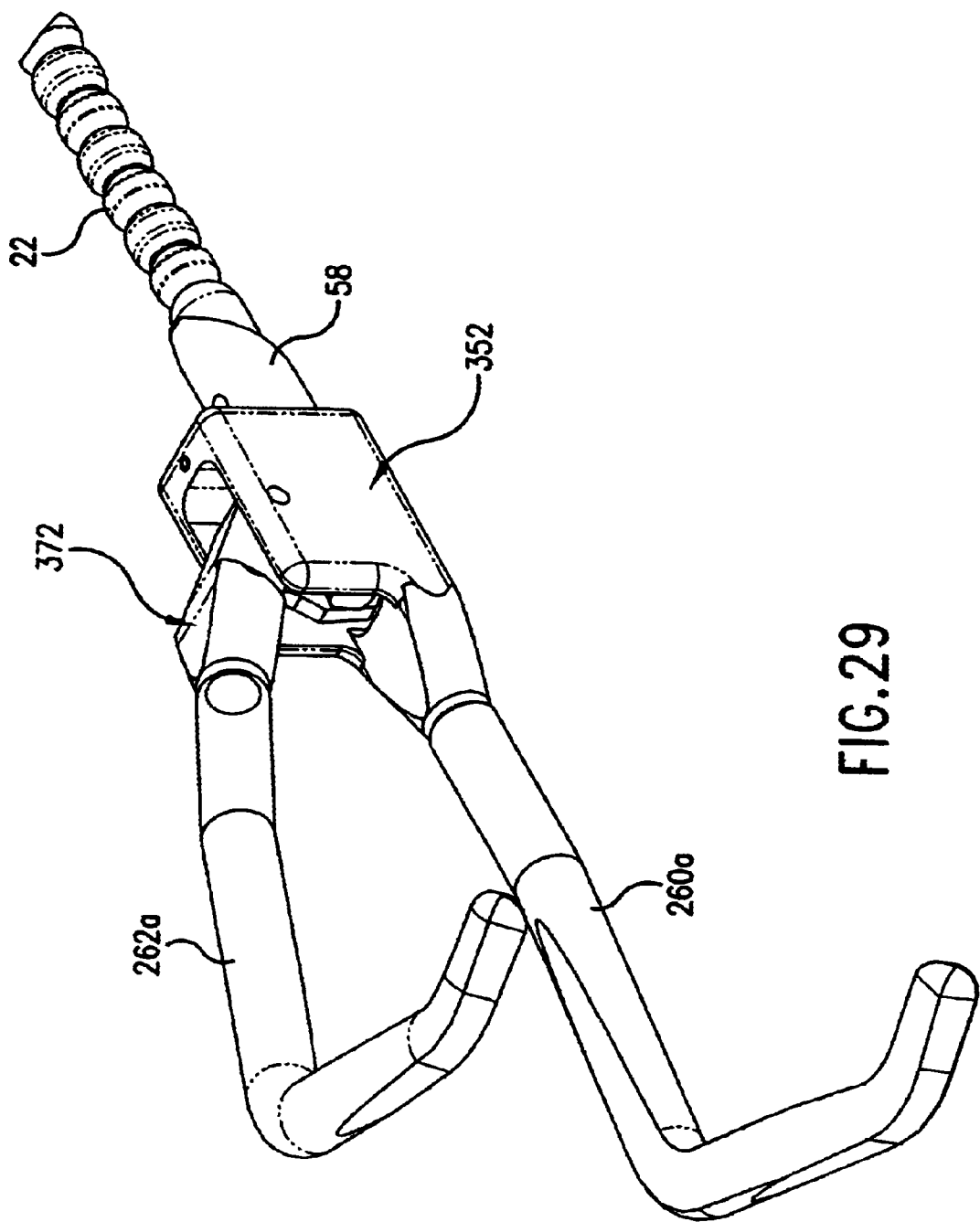
FIG. 29 is a perspective view of the gripping assembly of the clamp of FIG. 1 shown in use with different jaws.

The jaws 260, 262 can be removed from the bores 350 and 370, respectively, and replaced with a different set of jaws, such as 260a, 262a that are shown in FIG. 29. Reference should be made to U.S. Pat. No. 6,293,954 that is also assigned to the present assignee, which describes how removable jaws such as 260a, 262a can be implemented. The entire disclosure of U.S. Pat. No. 6,293,954 is hereby incorporated by this reference as though set forth fully herein.

Thus, the present invention provides a clamping device (the clamp assembly 20) that can effectively clamp a blood vessel, tissue or other anatomical structure at a surgical site, while not interfering with the surgeon's access to the surgical site. The shaft assembly that includes a flexible shaft and nested telescoping tubes 32 allows the shaft assembly to be both completely rigid and completely flexible. The rigid shaft that is formed when the telescoping tubes 32 are fully deployed is capable of withstanding axial loads, side loads, moments and torques applied to the jaws 260, 262. As a result, the surgeon can use the jaws 260, 262 to poke and prod around the surgical site. In addition, the lock housing 70 ensures that the jaws 260, 262 are not rotatable with respect to the shaft 22.

Alternative Embodiment of The Ratchet Assembly

Figure 30:
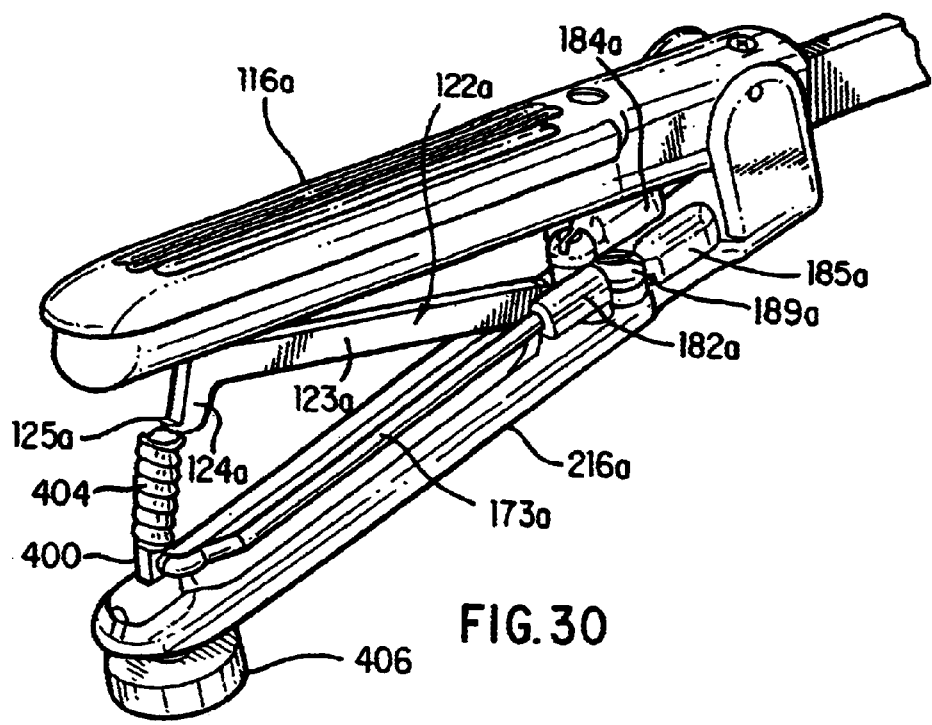
FIG. 30 is a perspective sectional view of a handle assembly having a ratchet assembly according to another embodiment of the present invention.
Figure 31:
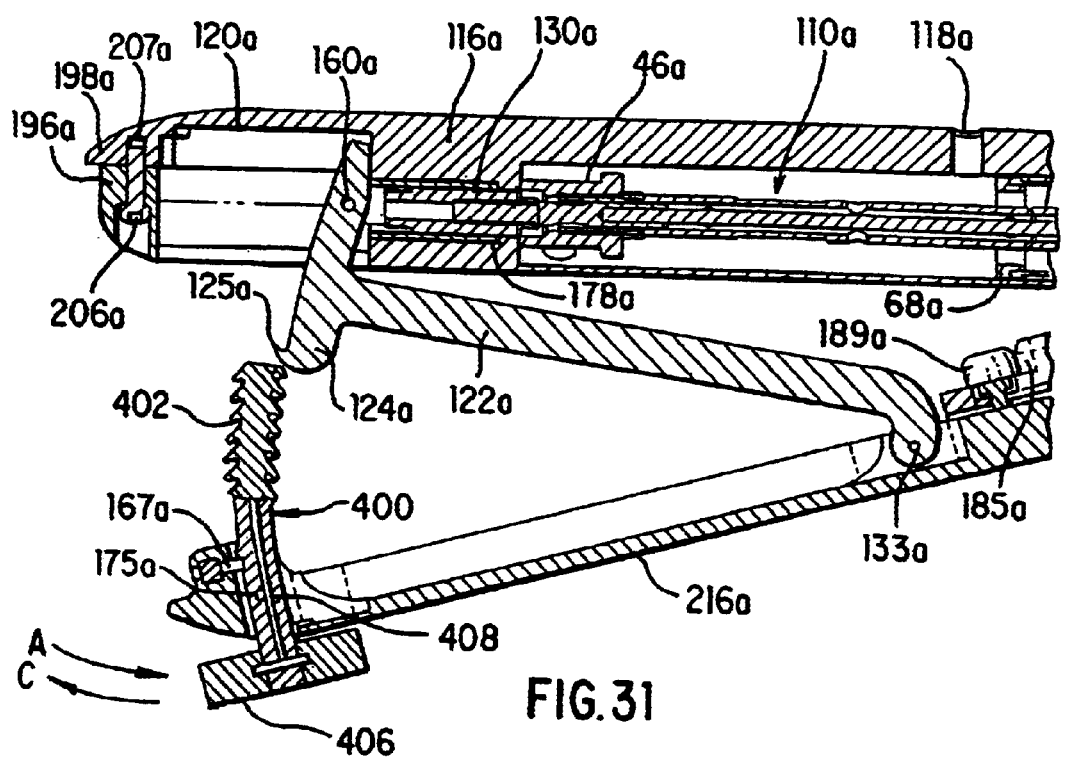
FIG. 31 is a cross-sectional view of the handle assembly of FIG. 30.

FIGS. 30 and 31 illustrate a ratchet assembly according to another embodiment of the present invention. In FIGS. 30 and 31, the ratchet 400 differs from the ratchet 164 provided in FIGS. 6A, 6B and 15, and the transverse piece 124 of the ratchet rack 122 is modified so that it has only one (or more) teeth 125a positioned at about the bottom of its proximal-facing surface. Otherwise, all the other elements of the handle assembly illustrated in FIGS. 6A, 6B and 15 are the same as the handle assembly in FIGS. 30 and 31. As a result, the elements of the handle assembly in FIGS. 30 and 31 bear the same numeral designation as the corresponding elements of the handle assembly in FIGS. 6A, 6B and 15, except that an "a" has been added to the numeral designations in FIGS. 30 and 31.

The ratchet 400 has a worm gear 402 at its upper end that has a continuous helical groove 404 on its external surface, as best shown in FIG. 30. The worm gear 402 is positioned at a slight angle towards the transverse piece 124a, so that the tooth 125a is adapted to engage a portion of the groove 404. A dial 406 is provided at the bottom end of the ratchet 400. The ratchet 400 has a bore through which a drive shaft 408 extends. The drive shaft 408 connects the dial 406 at one end with the worm gear 402 at the other end. The spring 167a naturally biases the worm gear 402 of the ratchet 400 towards the ratchet rack 122a about the pivot point defined by the pin 175a (in the same manner as pin 175 in FIG. 15), so that the tooth 125a can be made to engage the groove 404.

When the handle pieces 116a and 216a are closed, the tooth 125a engages the helical groove 404 on the worm gear 402. However, as best shown in the side cross-sectional view in FIG. 31, the groove 404 actually defines a plurality of ratchet teeth, each having an angled lower engagement surface that is adapted to engage the one or more teeth 125a on the transverse piece 124a. The fact that the groove 404 provides a plurality of ratchet teeth allows for the worm gear 402 to provide for two types of adjustments for the clamping force of the handle pieces 116a and 216a. A first type of adjustment is a discrete adjustment similar to conventional ratchet devices, in which the tooth 125a skips over one or more teeth defined by the groove 404 (operating essentially as a ratchet rack) to adjust the clamping force. Each tooth defined by the groove 404 would therefore account for a discrete or preset degree of adjustment. A second type of adjustment is a continuous adjustment provided by the helical path of the groove 404, in which the dial 406 is rotated to cause the drive shaft 408 and the worm gear 402 to rotate. As the helical groove 404 rotates, the tooth 125a will travel up or down along the helical groove 404 (depending on the direction of rotation of the dial 406), thereby causing the ratchet 400 to travel up or down, which allows for very fine or small adjustments to the clamping force of the handle pieces 116a and 216a.

Thus, the surgeon can use the ratchet 400 in one of two ways, either as a typical ratchet system (where the tooth 125a is locked by one tooth from a ratchet rack) to obtain discrete engagements, or as a continuous path where the degree of the clamping force can be fine-tuned.

The operation of the handle assembly of FIGS. 30 and 31 is essentially the same as for the handle assembly in FIGS. 6A, 6B and 15. For example, the engagement between the tooth 125a and the groove 404 can be released by pressing one or both of the first and second ratchet release buttons 184a and 185a towards each other in the direction of arrow B in FIG. 26. The inward pivoting motion of one or both of the ratchet release buttons 184a, 185a will push the gimble 182a and the transmission rod 173a in a proximal direction (see arrow C in FIG. 31) to pivot the ratchet 400 about the pivot point pin 175a so that the groove 404 is pivoted in the proximal direction (see arrow C in FIG. 31, thereby releasing the engagement between the groove 404 and the tooth 125a.

Alternatively, the surgeon can push the dial 406 in the distal direction indicated by the arrow A in FIG. 31, thereby pivoting the ratchet 400 about the pivot point 175a so that the worm gear 402 is pivoted in the direction of the arrow C in FIG. 31, which releases the engagement between the worm gear 402 and the tooth 125a. Thus, the dial 406 also operates as a lever to pivot the ratchet 400.

Alternative Embodiments of the Rigid Element

FIGS. 32A–36 illustrate alternative embodiments of rigid elements that can be deployed to support the flexible shaft 22 so that the entire clamp 20 can be made generally rigid. The elements in the assemblies in FIGS. 32A–36 bear the same numeral designation as the corresponding elements of the assembly in FIGS. 1–28, except that a different letter (e.g., "d", "e", etc.) has been added to the numeral designations in FIGS. 32A–36.

Figure 32B:
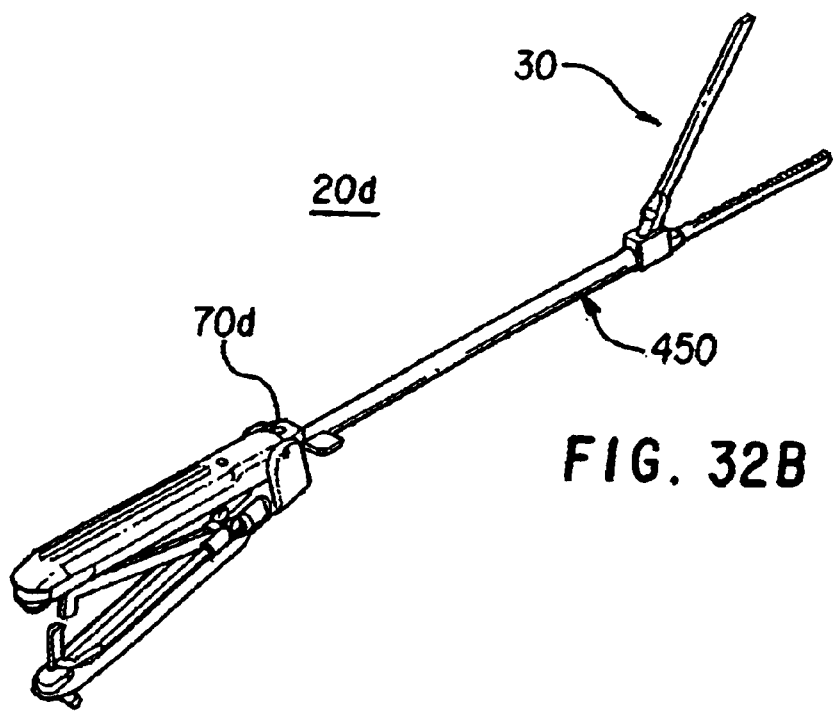
FIG. 32B is a perspective view of the clamp and rigid element of FIG. 32A.
Figure 32A:
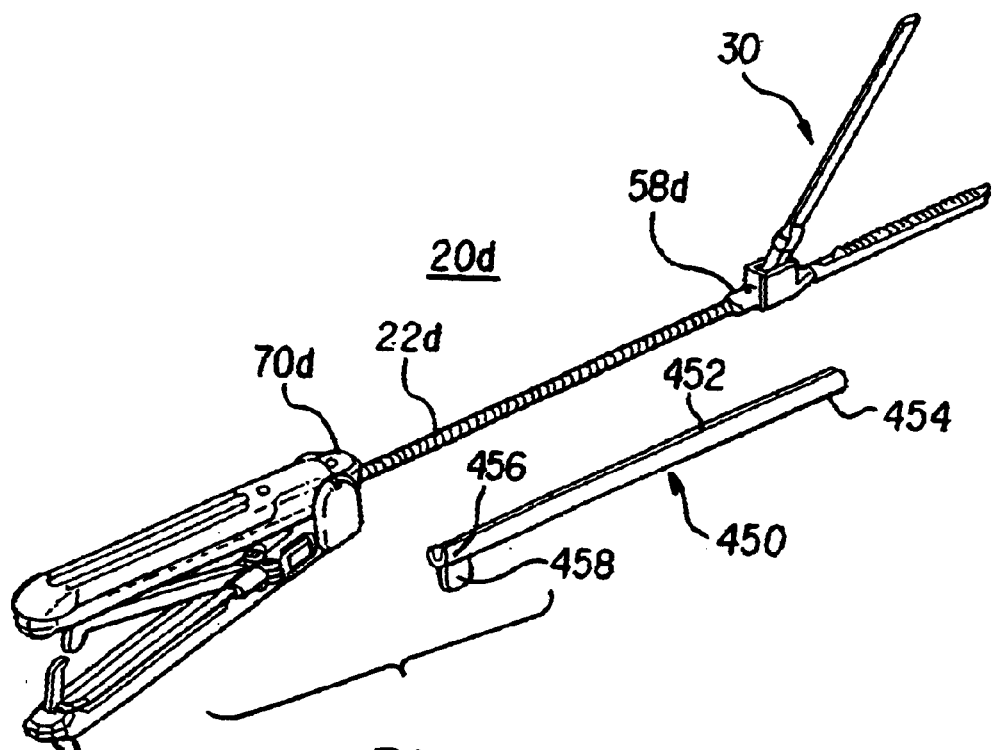
FIG. 32A is an exploded perspective view of a rigid element according to another embodiment shown in use with the clamp of FIG. 2.

FIGS. 32A and 32B illustrate the use of a rigid support that can be snapped on or off the clamp 20d. The clamp 20d in FIG. 32A can be the same as the clamp 20 as shown in FIG. 2, except that there are no telescoping tubes, and the housing 70d (which is similar to the housing 70) is permanently secured to the handle assembly. In particular, the rigid support 450 has a generally cylindrical rigid tubular configuration with a longitudinal slit 452 extending from the distal end 454 of the support 450 to the opposing proximal end 456 of the support 450. The slit 452 is preferably wide enough so that the shaft 22d (which can be the same as the shaft 22) can be passed through the slit 452. The distal end 454 of the support 450 can be snap-fitted to the helix cylinder 58d (which can be the same as the helix cylinder 58) since the helix cylinder 58d has a larger diameter than the shaft 22d. As an alternative, the helix cylinder 58d can have a square configuration (or flat surfaces) so that the support 450 cannot rotate with respect to the shaft 22d when the support 450 has been snap-fitted on to the shaft 22d. The proximal end 456 of the support 450 can also be snap-fitted to a cylinder (not shown) that is rigidly mounted to the housing 70d. This cylinder that is mounted to the housing 70d can also have a square configuration (or flat surfaces) so that the support 450 is locked with respect to the shaft 22d. The support 450 also has a handle 458 that can be gripped by the physician to remove or deploy the support 450. Thus, when it is desired to render the entire clamp 20d rigid, the physician snap-fits the support 450 over the entire length of the shaft 22d, as shown in FIG. 32B. When it is desired to render the shaft 22d flexible, the physician simply removes the support 450 from the shaft 22d, as shown in FIG. 32A.

FIGS. 33A and 33B illustrate the use of a rigid support assembly 470 that is carried by the shaft 22e. The clamp 20e in FIG. 33A can be the same as the clamp 20 as shown in FIG. 2, except that there are no telescoping tubes and a proximal block 472 is permanently secured to the distal end of the handle assembly. In particular, the proximal block 472 can be secured to a distal end of the housing 70e, can be part of the housing 70e, or can even replace the housing 70e. The rigid support assembly 470 includes the proximal block 472, a retractable distal block 474, and a rigid rod 476 having a distal end 478 that is permanently secured to the distal block 474 at a location offset from the center of the distal block 474. The distal block 474 can be secured to the helix cylinder 58e, or can be merely positioned adjacent the helix cylinder 58e when the rod 476 extends over the entire length of the shaft 22e. The distal block 474 has a bore through which the shaft 22e can extend. The body of the rod 476 extends through a bore that is provided at a location offset from the center of the proximal block 472. The rod 476 also has a handle 480 provided at its proximal end 482. Thus, when it is desired to render the entire clamp 20e rigid, the physician pulls the distal block 474 over the length of the shaft 22e so that the rod 476 is parallel (and not coaxial) to the shaft 22e, as shown in FIG. 33B. When it is desired to render the shaft 22e flexible, the physician simply withdraws the distal block 474 along the length of the shaft 22e until the distal block 474 is adjacent the proximal block 472, as shown in FIG. 33A.

Figure 34A:
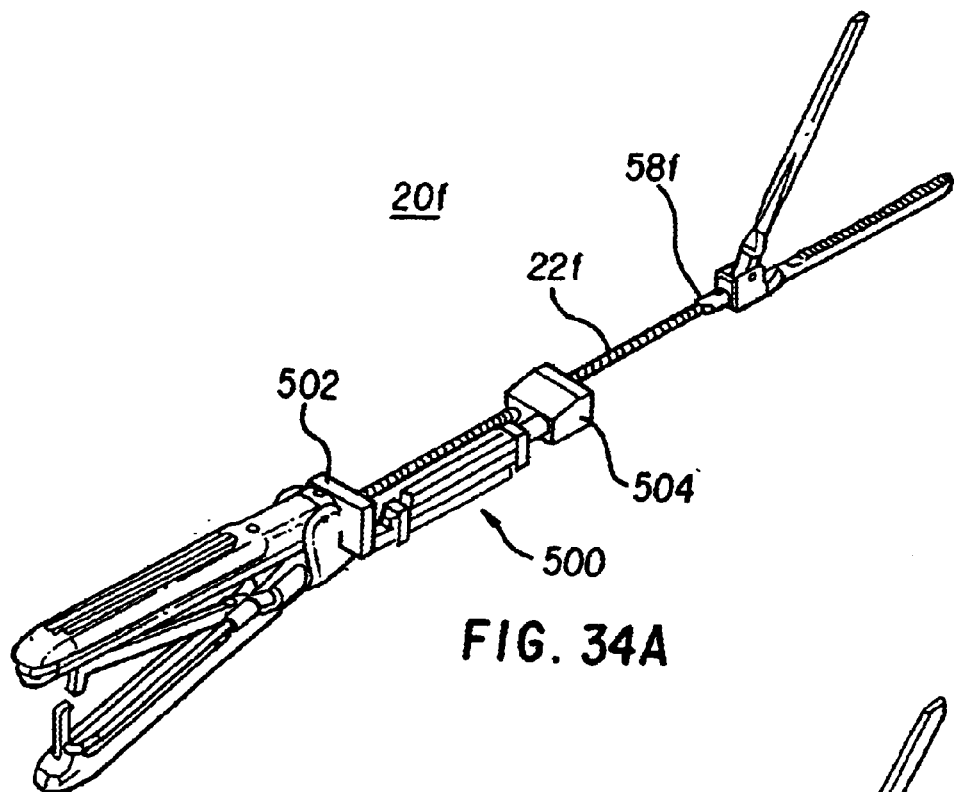
FIG. 34A is a perspective view of a rigid support assembly according to another embodiment shown in use with the clamp of FIG. 2.
Figure 34B:
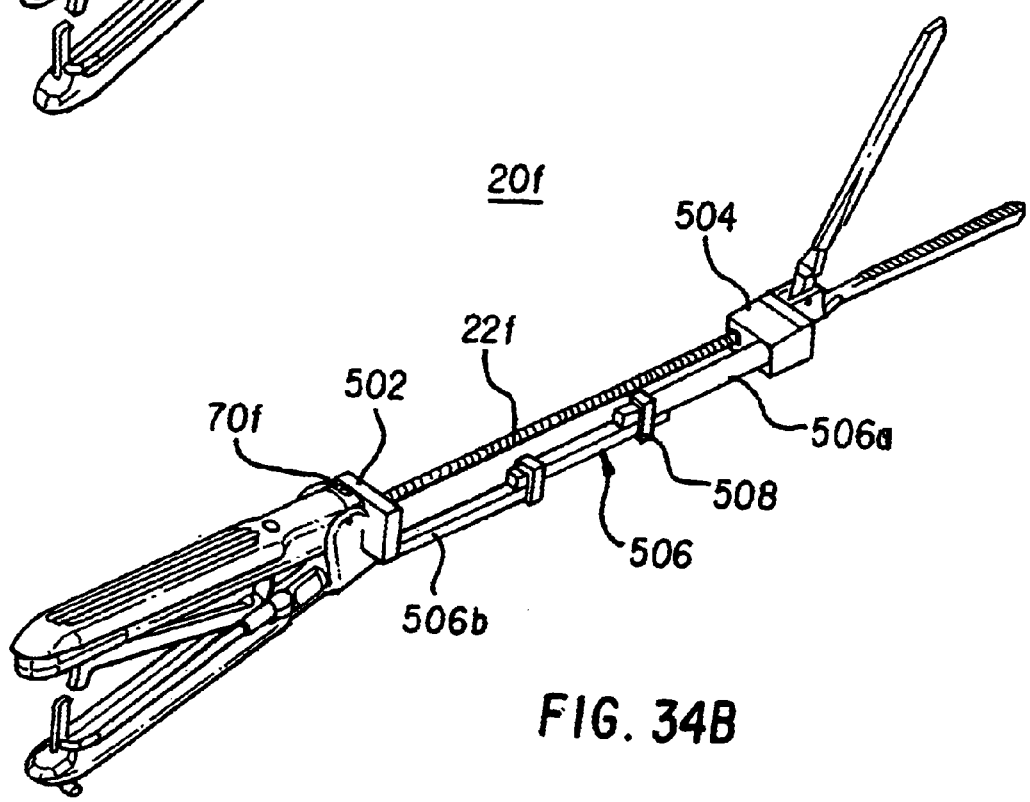
FIG. 34B is a perspective view of the clamp and rigid support assembly of FIG. 34A.

FIGS. 34A and 34B illustrate the use of another rigid support assembly 500 that is carried by the shaft 22f. The clamp 20f in FIG. 34A can be the same as the clamp 20 as shown in FIG. 2, except that there are no telescoping tubes, and a proximal block 502 is permanently secured to the distal end of the handle assembly. In particular, the proximal block 502 can be secured to a distal end of the housing 70f, can be part of the housing 70f, or can even replace the housing 70f. The rigid support assembly 500 includes the proximal block 502, a retractable distal block 504, and a plurality of nestable rods 506, with a distal-most rod 506a that is permanently secured to the distal block 504 at a location offset from the center of the distal block 504, and a proximal-most rod 506d that is permanently secured to the proximal block 502 at a location offset from the center of the proximal block 502. The distal block 504 has a bore through which the shaft 22f can extend. The plurality of rods 506 are positioned generally parallel to each other, and each pair of adjacent rods 506 are retained in side-by-side fashion by a separate retaining ring 508. Each pair of adjacent rods 506 can slide with respect to the adjacent rod 506 within the retaining ring 508 that retains them. Thus, when it is desired to render the entire clamp 20f rigid, the physician pulls the distal block 504 over the length of the shaft 22f so that the rods 506 become unnested and extended in a parallel (and not coaxial) orientation with respect to the entire length of the shaft 22f, as shown in FIG. 34B. In this position, the distal block 504 can be secured to the helix cylinder 58f, or can be merely positioned adjacent the helix cylinder 58f, when the rods 506 extend over the entire length of the shaft 22f. When it is desired to render the shaft 22f flexible, the physician simply withdraws the distal block 504 along the length of the shaft 22f (with the rods 506 becoming nested or side-by-side) until the distal block 504 is at its closest position to the proximal block 502, as shown in FIG. 34A.

Even though the rods 506 are illustrated in FIGS. 34A and 34B as being side-by-side and parallel, the rods 506 can be coaxial in the same manner as the telescoping tubes described above, with the proximal-most rod 506d having the largest diameter and the distal-most rod 506a having the smallest diameter and nested inside the rods 506 that are proximal to it.

Figure 35:
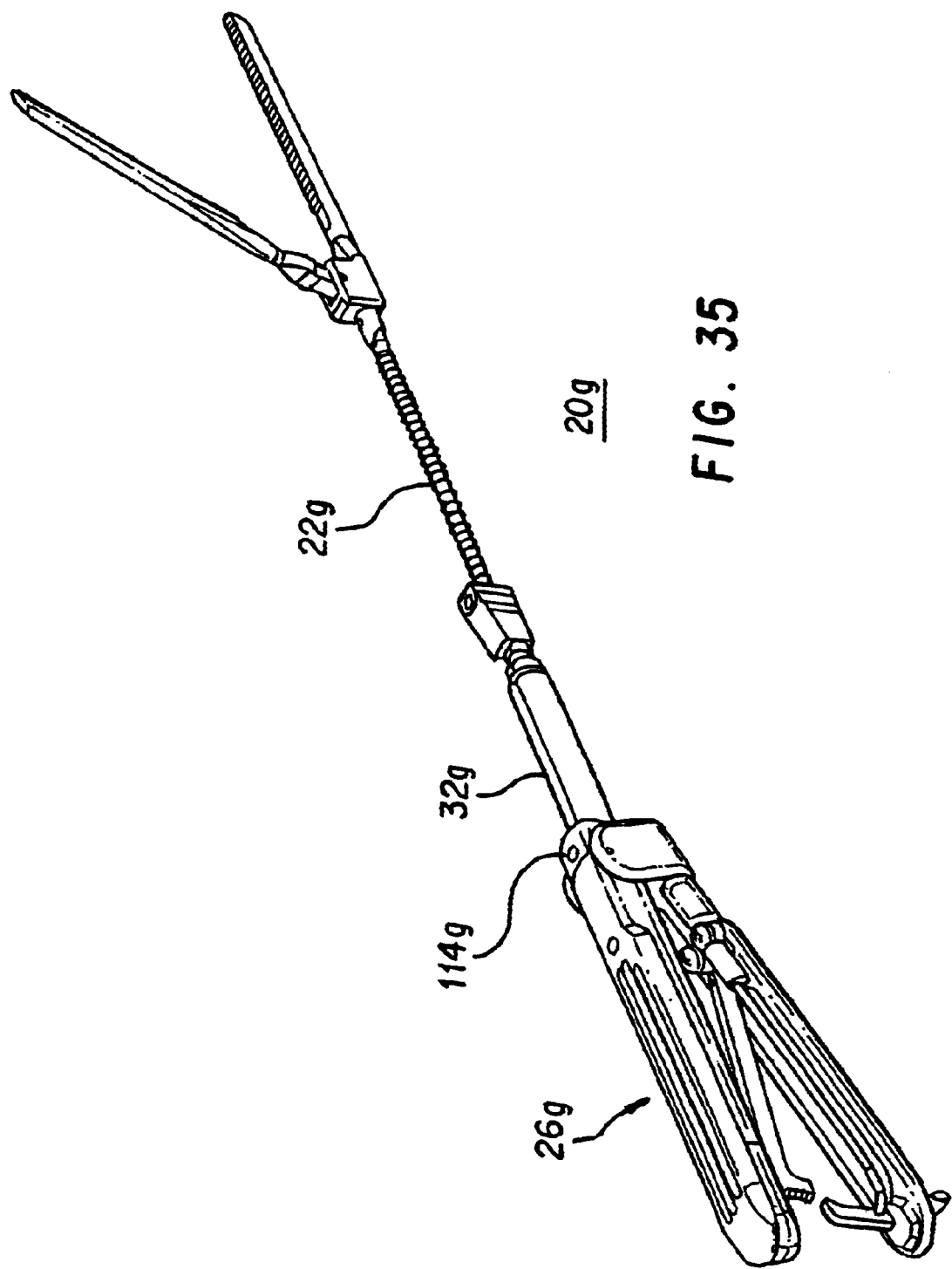
FIG. 35 is a perspective view of a plurality of telescoping tubes according to another embodiment shown in use with the clamp of FIGS. 1 and 2.

As a further alternative, FIG. 35 illustrates a clamp 20g that can be the same as the clamp 20 as shown in FIGS. 1 and 2, except that the telescoping tubes 32g are nested outside and adjacent the handle assembly 26g when the telescoping tubes 32g are fully retracted. The proximal-most telescoping tube 32g can be secured to the handle end piece 114g (such as by pressing the tube 32b into the handle end piece 114g, or by screwing, bonding or welding the tube 32b and the handle end piece 114g, or by machining the tube 32b and the handle end piece 114g as one piece), which can be the same as the handle end piece 114 in FIGS. 1, 2, 6A and 6B. Thus, the shaft 22g (which can be the same as the shaft 22) in clamp 20g of FIG. 35 cannot be flexible at its proximal end where the telescoping tubes 32g are nested when retracted. The telescoping tubes 32g can be deployed and retracted in the same manner as the telescoping tubes 32 described above. Although the telescoping tubes 32g are illustrated with the tubes having a progressively smaller diameter from the proximal-most tube to the distal-most tube, it is also possible to provide the tubes with a progressively larger diameter from the proximal-most tube to the distal-most tube.

Figure 36:
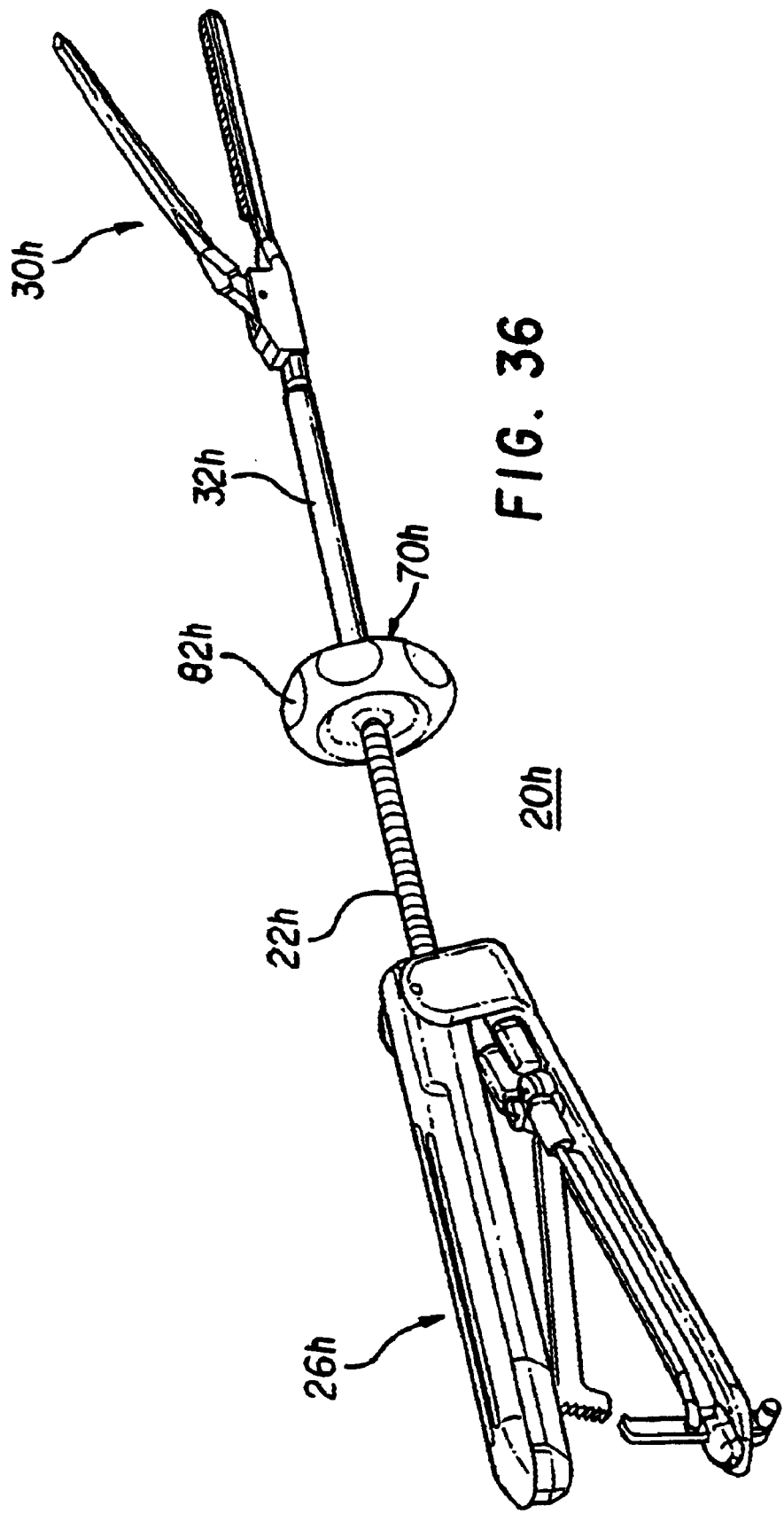
FIG. 36 is a perspective view of a plurality of telescoping tubes according to another embodiment shown in use with the clamp of FIGS. 1 and 2.

As yet another alternative, FIG. 36 illustrates a clamp 20h that has the same construction as the clamp 20 as shown in FIGS. 1 and 2, except for the differences noted in FIGS. 36–38 below, and that the telescoping tubes 32h are nested along a section of the shaft 22h adjacent the gripping assembly 30h when the telescoping tubes 32h are fully retracted. As a result, the elements of the handle assembly 26h and the gripping assembly 30h in FIGS. 36–38 bear the same numeral designation as the corresponding elements in FIGS. 6A, 6B, 9A–9C and 15, except that an "h" has been added to the numeral designations in FIGS. 36–38.

Figure 37:
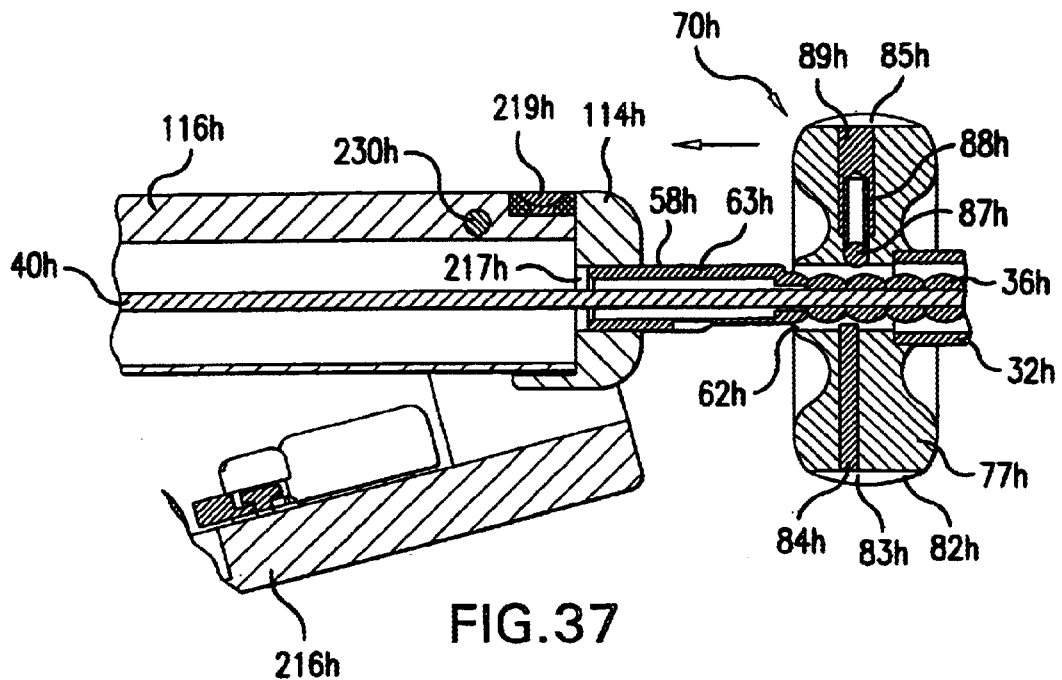
FIG. 37 is a cross-sectional view of the handle assembly of the clamp of FIG. 36.

Referring to FIG. 37, the handle assembly 26h is slightly different from the handle assembly 26 in FIGS. 6A and 6B in that the telescoping tubes 32h are no longer retained inside or connected to the bore 110h of the handle piece 116h. Instead, the helix cylinder 58h is now secured to the bore 217h of the handle end piece 114h, and functions to releasably lock a knob 70h that is similar to the lock housing 70.

The knob 70h is attached to the proximal-most telescoping tube 32h. The knob 70h has a generally circular body 77h having a generally cylindrical and longitudinal throughbore 62h. A portion of the proximal-most telescoping tube 32h is secured to a distal portion of the throughbore 62h, and the helix cylinder 58h is retained inside a proximal portion of the throughbore 62h. Wells 82h can be provided on the outer surface of the knob 70h to provide a convenient grip surface for the user's finger. A bottom hole 83h extends from the outer surface of the body 77h into a proximal portion of the throughbore 62h, and a dowel pin 84h is received inside the hole 83h. A transverse bore 85h extends from an opposite end of the outer surface of the body 77h into a proximal portion of the throughbore 62h. The transverse bore 85h has a shoulder adjacent its opening into the throughbore 62h. A ball 87h is seated in the shoulder of the transverse bore 85h in a manner similar to that shown in FIGS. 9A–9C and 13A–13C, and protrudes slightly into the throughbore 62h. A spring 88h is placed in the transverse bore 85h and is pressed against the ball 87h to maintain the ball 87h against the shoulder. Another dowel pin 89h (which can have the same construction as shown in FIGS. 14A and 14B) is positioned in the transverse bore 85h over the spring 88h and the ball 87h. The parts of the ball 87h that protrude into the throughbore 62h facilitate removable engagement with the dimple 63h of the helix cylinder 58h in the same manner as described above for the lock housing 70 and the helix cylinder 58 in FIGS. 9A–9C.

Figure 38:
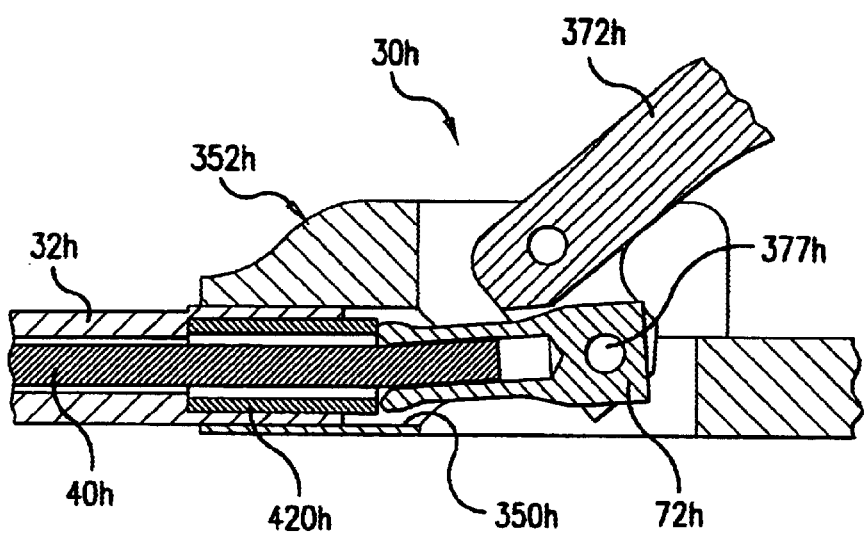
FIG. 38 is a cross-sectional view of the gripping assembly of the clamp of FIG. 36.

Referring to FIG. 38, the gripping assembly 30h is slightly different from the gripping assembly 30 in FIGS. 9A–9C in that the helix cylinder 58 has now been moved to the handle assembly 26h, and the distal-most telescoping tube 32h is secured inside the bore 350h of the stationary jaw base 352h. The spring 420h is provided inside the bore of the distal-most telescoping tube 32h, and abuts a shoulder inside the bore of the distal-most telescoping tube 32h. The cable holder 72h is positioned in the same manner as the cable holder 72 in FIGS. 9A–9C. The gripping assembly 30h operates in the same manner described above for the gripping assembly 30 in FIGS. 9A–9C.

Thus, when it is desired to render the entire clamp 20h rigid, the physician grips the knob 70h and pulls it in the proximal direction towards the handle assembly 26h to un-nest all the telescoping tubes 32h. The knob 70h can be removably locked with the helix cylinder 58h in the manner described above to maintain the telescoping tubes 32h over the entire length of the shaft 22h. When it is desired to render proximal portions of the shaft 22h flexible, the physician simply grips the knob 70h and pushes it in the distal direction towards the gripping assembly 30h to nest all the telescoping tubes 32h, as best shown in FIG. 36. Although the telescoping tubes 32h are illustrated with the tubes having a progressively smaller diameter from the proximal-most tube to the distal-most tube, it is also possible to provide the tubes with a progressively larger diameter from the proximal-most tube to the distal-most tube.

EXAMPLE

The clamps 20 and 20h of the present invention are especially well-suited for use in minimally-invasive procedures where the jaws 260, 262 can be introduced through a port, trocar or small incision (hereinafter collectively referred to as "Port"). In this Example, the same numerals are used to designate the same corresponding elements in both the clamps 20 and 20h. Such minimally-invasive procedures can include applications such as endoscopic or laproscopic applications. For example, during a minimally-invasive procedure, a surgeon may need to use an endoscope to view the surgical activity at the site of the procedure. In such minimally-invasive procedures, the Port is of a small size such that the surgeon's hands cannot readily access the surgical site through the Port. As a result, the surgeon can only manipulate the jaws 260, 262 via the handle assembly 26 or the knob 70h.

When used in a minimally-invasive procedure, the surgeon grips the handle pieces 116, 216 to close the jaws 260, 262, and then introduces the closed jaws 260, 262 and a portion of the shaft 22 through the Port into the interior of a patient. The surgeon then manipulates the jaws 260, 262 (via gripping of the handle pieces 116, 216) to manipulate the blood vessels, tissues and other anatomical structures. During this manipulation, the jaws 260, 262 can be either opened or closed. If closed, the jaws 260, 262 can be used in a similar manner as a retractor or other blunt instrument. If opened, the jaws 260, 262 can be used as a gripping element (i.e., like a clamp) or as a needle holder. The rigidity of the telescoping tubes 32 and 32h allows the surgeon to be able to manipulate the jaws 260, 262 solely by controlling the handle pieces 116, 216 that are positioned outside the patient's body. The rigid shaft that is formed by the fully deployed telescoping tubes 32 and 32h protrudes through the Port which acts as a fulcrum. For example, if the surgeon wishes to move the jaws 260, 262 to the right, the surgeon merely moves the handle pieces 116, 216 to the left to pivot the shaft 22 about the fulcrum. Next, the surgeon can (if desired) close the jaws 260, 262 by gripping the handle pieces 116, 216 to cause the jaws 260, 262 to grip a vessel, tissue or anatomical structure. At this point, the operation becomes slightly different for both clamps 20 and 20h.

For the clamp 20, with the shaft 22 extending through the Port, the surgeon can then withdraw the telescoping tubes 32 so that a portion of the shaft 22 is now completely flexible and bendable. The tubes 32 can be withdrawn by first gripping and withdrawing the proximal-most tube 32a which would likely be outside the patient's body. Since the tubes 32 are locked to each other in the manner shown in FIG. 28, withdrawal of the proximal-most tube 32a will cause the tube 32 that is distal to (i.e., adjacent to) the proximal-most tube 32a to be withdrawn slightly as well. At this time, each tube 32 will be pulled proximally, and this pulling force will cause the ball 87 in the lock housing 70 to be disengaged from the dimple 63 of the helix cylinder 58. The surgeon can then grip and withdraw the tube 32 that is distal to (i.e., adjacent to) the proximal-most tube 32a. In this manner, the surgeon can grip and withdraw each tube 32, one at a time, until the distal-most tube 32b has been withdrawn as well. The handle assembly 26 can then be moved away from the surgical site.

For the clamp 20h, with the shaft 22h extending through the Port, the surgeon can grip the knob 70h and push it in the distal direction towards the gripping assembly 30h to nest all the telescoping tubes 32h as shown in FIG. 36. This would render the proximal portion of the shaft 22h completely flexible and bendable. The handle assembly 26h can then be moved away from the surgical site. At this point, the surgeon can still use the knob 70h to manipulate the jaws 260, 262. Since the rigid telescoping tubes 32h always extend through the Port and into the patient's body (regardless of whether the telescoping tubes 32h are nested or retracted), the telescoping tubes 32h will always act as a fulcrum. As a result, the surgeon does not need to use the handles 116h and 216h to manipulate the jaws 260, 262. Thus, the knob 70h now acts as a handle. However, the surgeon will still need to use the handles 116h and 216h to open and close the jaws 260, 262.

Depending on the surgical procedure, some of the telescoping tubes 32 and 32h can be extended again (or only some, but not all, of the tubes 32 and 32h can be withdrawn or retracted) to cover a portion of the shaft 22 to render that portion of the shaft 22 completely rigid again.

In addition, if it is necessary to perform manipulation of other vessels, tissues or anatomical structures at the surgical site, the surgeon can completely extend all the telescoping tubes 32 or 32h to render the shaft completely rigid again, and then manipulate the jaws 260, 262 (via the handle pieces 116, 216) according to the steps described above. To extend one or more tubes 32 in the clamp 20, the surgeon locks each tube 32 to an adjacent tube 32 using the dimples 139 and the tabs 141 according to the technique described above in connection with FIG. 28, and then pushes each tube 32 (starting with the distal-most tube 32b) back through the Port into the patient's body. Similarly, to extend one or more tubes 32h in the clamp 20h, the surgeon locks each tube 32h to an adjacent tube 32h using the dimples 139 and the tabs 141 according to the technique described above in connection with FIG. 28, and then pulls each tube 32h (starting with the proximal-most tube 32h) back through the Port out of the patient's body.

Other Embodiments For The Gripping Assembly

Figure 39:
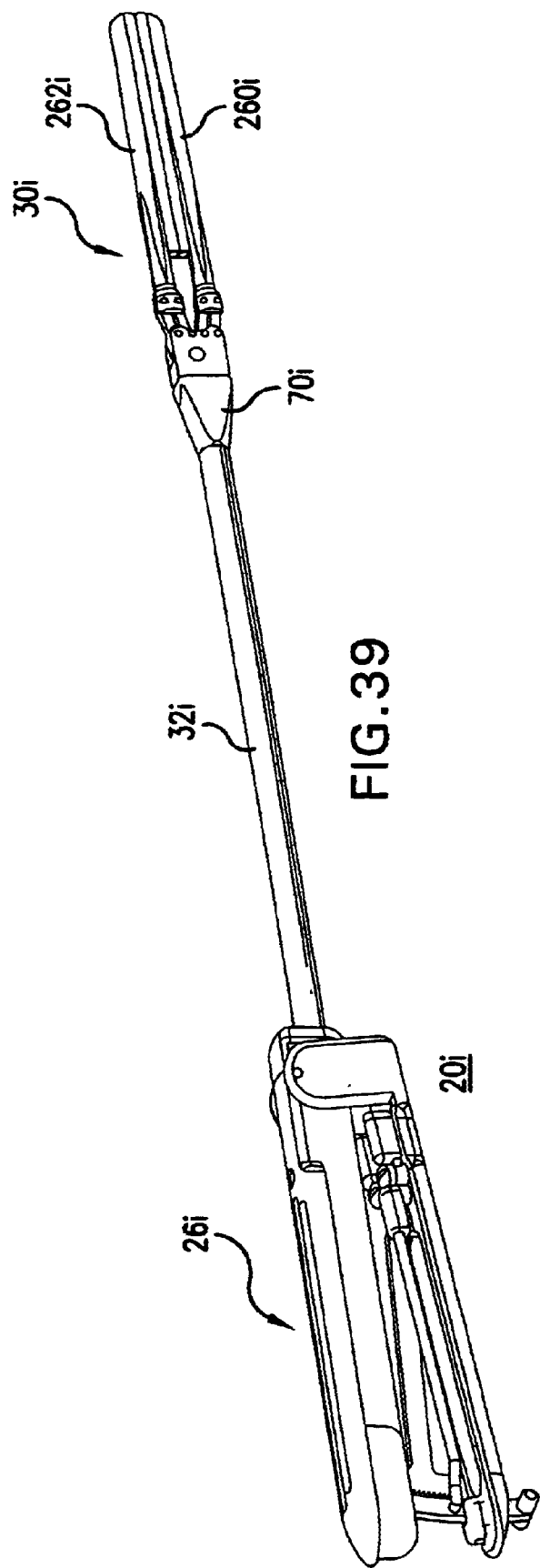
FIG. 39 is a perspective view of a gripping assembly according to another embodiment shown in use with the clamp of FIGS. 1 and 2, and with the rigid support assembly fully extended.
Figure 40:
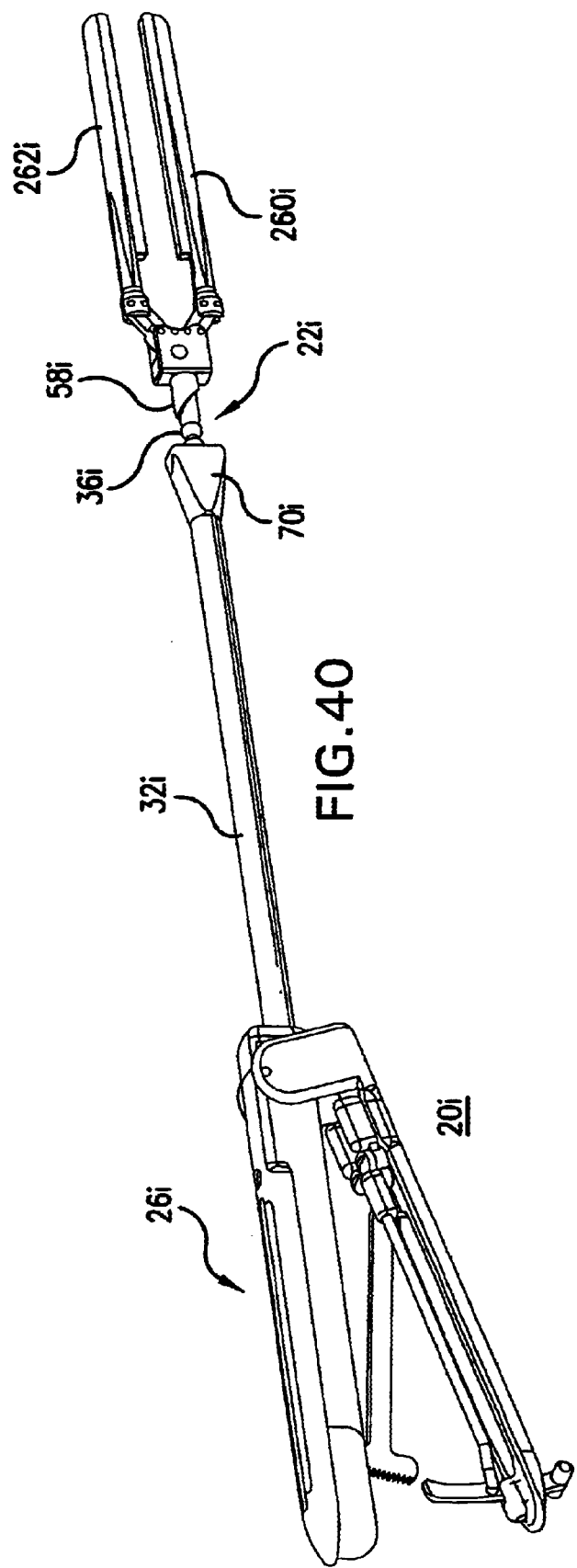
FIG. 40 is a perspective view of the gripping assembly of FIG. 39 with the rigid support assembly partially retracted.
Figure 44:
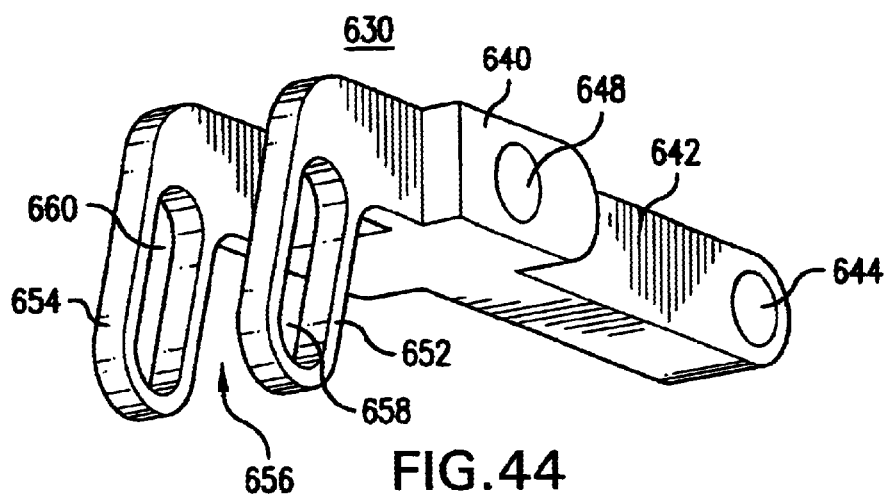
FIG. 44 is a perspective view of the first link of the gripping assembly of FIG. 39.
Figure 45:
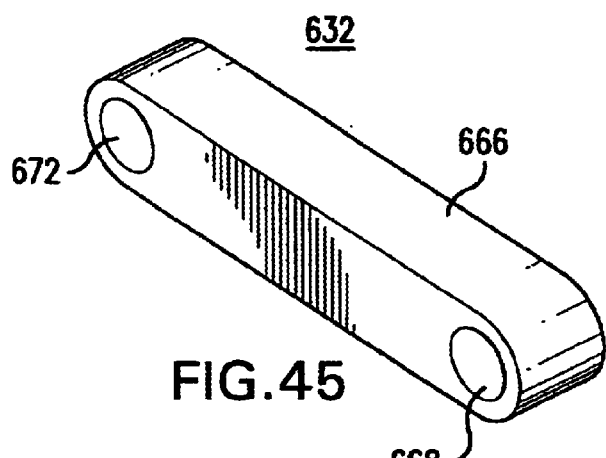
FIG. 45 is a perspective view of the second link of the gripping assembly of FIG. 39.

FIGS. 39 and 40 illustrate a clamp 20i that has the same construction as the clamp 20 as shown in FIGS. 1 and 2, except for the differences noted in FIGS. 39–48 below. As a result, the elements of the clamp 20i in FIGS. 39–48 that are the same as those in the embodiment of FIGS. 1–6B and 15–27 bear the same numeral designation as the corresponding elements in FIGS. 1–6B and 15–27, except that an "i" has been added to the numeral designations in FIGS. 39–48.

The clamp 20i in FIG. 39 has a single rigid tube 32i instead of the plurality of telescoping tubes 32 in FIGS. 1–2. Whether a single tube 32i is provided or a plurality of telescoping tubes 32 is provided depends on the intended application. By having a single tube 32i that is coaxial to the shaft 22i, the surgeon can insert the jaws 260i, 262i of the gripping assembly 30i through a small incision or port and still be able to extend or retract the tube 32i from outside the body of the patient. On the other hand, a plurality of telescoping tubes 32 can be used when the jaws 260i, 262i of the gripping assembly 30i are inserted through a large incision because the surgeon can reach all the way into the incision to grip the distal-most-telescoping tube 32b to engage this tube 32b with the gripping assembly 30i.

The proximal end of the tube 32i is secured to the handle assembly 26i in the same manner as the proximal-most telescoping tube 32a is secured to the handle assembly 26 in FIGS. 1 and 2. A lock housing 70*i* is provided at the distal end of the tube 32*i*. The lock housing 70*i* can be the same as the lock housing 70 in FIGS. 1 and 2. The lock housing 70*i* is movable with respect to the helix cylinder 58*i*, and can be removably secured to the helix cylinder 58*i*. The helix cylinder 58*i* can be the same as the helix cylinder 58 in FIGS. 1 and 2.

FIG. 39 shows the clamp 20*i* with the tube 32*i* fully extended so that the lock housing 70*i* engages the helix cylinder 58*i* in the manner shown in FIGS. 9B and 9C for lock housing 70 and helix cylinder 58. In addition, FIG. 39 shows the jaws 260*i*, 262*i* of the gripping assembly 30*i* closed. FIG. 40 shows the clamp 20*i* with the tube 32*i* partially retracted to expose a few beads 36*i* of the shaft 22*i*. When the tube 32*i* is partially retracted, the jaws 260*i*, 262*i* can be articulated. Depending on the desired bend radius, different numbers of beads 36*i* can be exposed. For example, the bend radius will be small if only one or two beads 36*i* are exposed. On the other hand, the bend radius will be larger if several beads 36*i* are exposed. In addition, FIG. 40 shows the jaws 260*i*, 262*i* opened in a manner such that the jaws 260*i*, 262*i* are parallel to each other. The jaws 260*i*, 262*i* can be opened or closed at any time, regardless of whether the tube 32*i* is fully extended or partially retracted.

The features of the gripping assembly 30*i* are best illustrated in connection with FIGS. 41–46. Referring to FIGS. 41, 43A and 43B, the gripping assembly 30*i* has a jaw housing 600 that has a stepped bore. The stepped bore has a first bore portion 602 extending from the proximal surface 604 of the jaw housing 600 to a second bore portion 606 at the distal surface 608 of the jaw housing 600. The first bore portion 602 has a greater diameter than the second bore portion 606. A pair of parallel walls 610, 612 has four openings 614 which are aligned to receive the dowel pins described below. A plurality of indentations 615 are provided on the outer surfaces of the jaw housing 600 to allow a secondary instrument to articulate the jaws 260*i*, 262*i* of the clamp 20*i*, as described in greater detail below.

A cable terminator 624 extends through the second bore portion 606 in to the space 616 between the walls 610, 612. The proximal end of the cable terminator 624 is received inside the distal part of the bore (e.g. 62 in FIGS. 11A–11C) of the helix cylinder 58*i*. The helix cylinder 58*i* can be identical to the helix cylinder of FIGS. 11A–11C. A spring 420*i* is also retained inside the bore (e.g. 62) and overlies the cable 40*i* which extends through the bore (e.g. 62) of the helix cylinder 58*i*. The distal end of the cable 40*i* is secured (e.g. by brazing, gluing, crimping, etc.) inside the proximal bore of the cable terminator 624.

Each jaw 260*i*, 262*i* is operatively connected to the jaw housing 600 by a set of links. Each set of links can have two links that include a first link 630 and a second link 632. The first link 630 is shown in greater detail in FIG. 44 and the second link 632 is shown in greater detail in FIG. 45. The two sets of links 630, 632 enable the jaws 260*i*, 262*i* to be opened and closed while maintaining them parallel to each other at all times (even during the opening and closing motions).

This parallel disposition of the jaws 260*i*, 262*i* allows for a number of benefits. First, parallel closing jaws provide an even force distribution across the jaws compared to pivoting jaws where the force increases closer to the pivot. This allows the clamp 20*i* to occlude a vessel with less average clamping force. In a pivoting clamp 20*i* that is used to occlude a large vessel, the clamping force at the distal end of the jaws needs to be sufficient to occlude the vessel. As a result, the clamping force near the proximal end of the jaws must be greater than required to occlude the vessel. Second, if the jaws 260*i*, 262*i* hold an accessory device (e.g., probe, transmitter, coil, lens, wire, etc., as described below) that is connected to an energy source for cautery, coagulation or ablation, the parallel disposition of the jaws 260*i*, 262*i* will optimize performance since the probes in each jaw 260*i*, 262*i* will be spaced-apart by the same distance throughout the length of the probes. This allows for uniform transfer of energy to the tissue along the length of the jaws 260*i*, 262*i*.

The first link 630 has a generally L-shaped body 640 having a tongue 642 extending from one end of the body 640. The tongue 642 has an opening 644 which receives a dowel pin 646. The central portion of the body 640 also has an opening 648 which receives another dowel pin 650. Two parallel extensions 652 and 654 extend from the other end of the body 640 and define a space 656 therebetween. Each extension 652 and 654 has an elongated opening 658 and 660, respectively.

The second link 632 has a generally elongated body 666 having an opening 668 at a first end which receives a dowel pin 670, and another opening 672 at a second end which receives another dowel pin 674.

Figure 46:
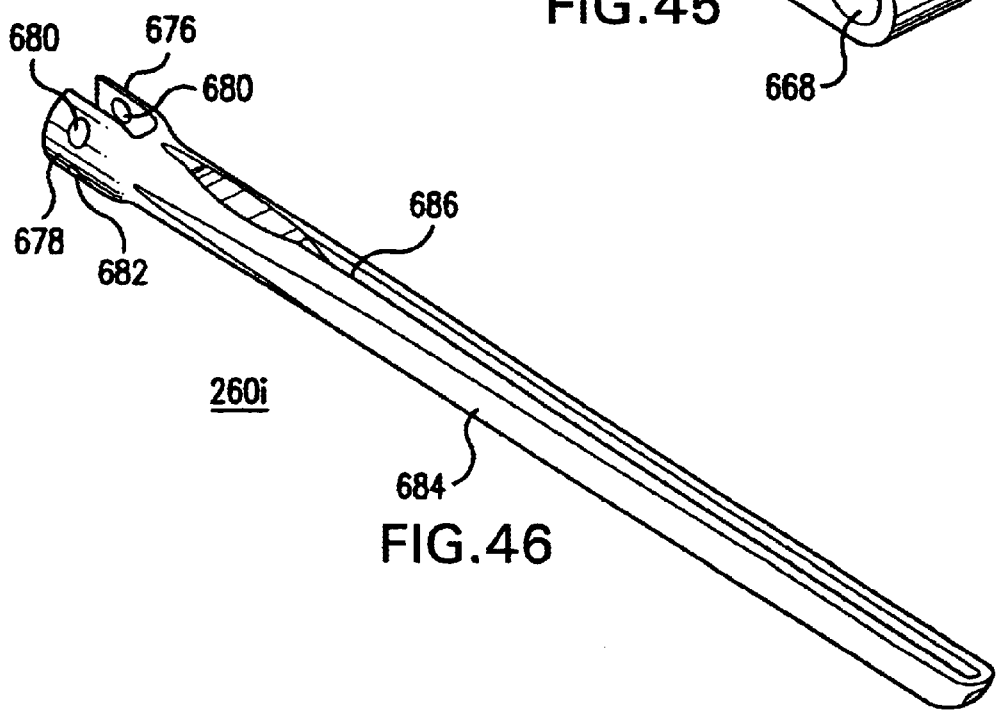
FIG. 46 is a perspective view of the lower jaw of the gripping assembly of FIG. 39.

FIG. 46 illustrates the lower jaw 260*i*. The upper jaw 262*i* has a symmetrical structure and will not be described in greater detail. The jaw 260*i* has two proximal extensions 676 and 678 that are parallel to each other and which define a space therebetween. Each extension 676, 678 has two openings 680 and 682, with the openings 680 along the extensions 676, 678 being aligned with each other, and the openings 682 along the extensions 676, 678 being aligned with each other. The jaw 260*i* has a body portion 684 which has a trough 686. An insert 688 can be secured to the trough 686 in a manner well-known in the art. The insert 688 can be atraumatic inserts for occluding vessel or grasping tissue. The insert 688 can also be adapted to hold an energy source for cautery, coagulation or ablation, in which case the insert 688 would be adapted to hold a probe, coil, transmitter, lens, wire and other elements that can be connected to an energy source.

Referring now to FIGS. 41 and 42, the dowel pin 646 extends through the openings 682 in the jaws 260*i*, 262*i* and the opening 644 in the first links 630. Similarly, the dowel pin 670 extends through the openings 680 in the jaws 260*i*, 262*i* and the opening 668 in the second links 632. Portions of the first and second links 630, 632 extend into the space between the extensions 676, 678 of each jaw 260*i*, 262*i*. In addition, the dowel pin 650 extends through the openings 648 in the first links 630 and corresponding openings 614 in the jaw housing 600. Similarly, the dowel pin 674 extends through the openings 672 in the second links 632 and corresponding openings 614 in the jaw housing 600. Portions of the first and second links 630, 632 extend into the space 616 between the walls 610, 612 of the jaw housing 600. In addition, another dowel pin 690 extends through a distal opening at the cable terminator 624 and the elongated openings 658, 660 of both first links 630. The extensions 652, 654 of the first links 630 extend into the space 616, and the distal portion of the cable terminator 624 extends into the space 656 between the extensions 652, 654. Each of the dowel pins 646, 650, 670, 674 and 690 described herein act as pivot points about which the coupled elements can pivot.

The pivoting connections effectuated by the dowel pins 646, 650, 670, 674 and 690 allow for the jaws 260*i*, 262*i* to be maintained parallel to each other at all times even when they are opened and closed.

As described above, the spring 420*i* is provided inside the helix cylinder 58*i*, and functions to continuously bias the jaws 260*i*, 262*i* apart from each other by pushing or exerting a bias against the cable terminator 624. In particular, the bias that is exerted against the cable terminator 624 pushes the cable terminator 624 in the distal direction, as shown in FIG. 41, so that the first links 630 are pivoted about the dowel pins 690 and 650 to cause both the tongues 642 of the first links 630 to move apart from each other. At the same time, the first links 630 also pivot about the dowel pins 646 to push the two jaws 260*i*, 262*i* apart from each other to assume the opened position. The second links 632 pivot about the dowel pins 670, 674 away from each other, and function to provide additional support between the jaws 260*i*, 262*i* and the jaw housing 600 to keep the jaws 260*i*, 262*i* spaced-apart in a parallel manner.

To close the jaws 260*i*, 262*i*, the surgeon grips the handle pieces 116, 216 towards each other to overcome the bias of the spring 420*i*. In particular, when the surgeon grips the handle pieces 116, 216, the cable 40*i* is pulled in the proximal direction, so that the cable terminator 624 is pulled proximally along with the cable 40*i*. As the cable terminator 624 moves in the proximal direction, the cable terminator 624 will overcome the bias of the spring 420*i* (see FIG. 42), so that the first links 630 are pivoted about the dowel pins 690 and 650 to cause both the tongues 642 of the first links 630 to move towards each other. At the same time, the first links 630 also pivot about the dowel pins 646 to pull the two jaws 260*i*, 262*i* towards each other to assume the closed position. The second links 632 pivot about the dowel pins 670, 674 towards each other.

FIG. 47 illustrates a modification that can be made to the gripping assembly 30*i* in FIGS. 39–46. In FIG. 47, the first and second links 630, 632 of each jaw 260*i*, 262*i* can be positioned so that the inserts 688 of the jaws 260*i*, 262*i* are a certain distance d apart from each other when the jaws 260*i*, 262*i* are closed. This distance d can be important because there are applications where it is desirable to prevent the two inserts 688 from contacting each other so as to decrease the clamping force on the vessel or tissue being clamped. For example, this can be important when the inserts 688 are energized for cautery, coagulation or ablation.

FIG. 48 illustrates the use of a secondary instrument to articulate the jaws 260*i*, 262*i* of the clamp 20*i*. For example, if the jaws 260*i*, 262*i* have been inserted through a small incision or port, a secondary instrument (such as a needle holder or forceps 694 as shown in FIG. 48) can be inserted through a different small incision (or the original incision if the incision is large enough) or port to grasp the jaw housing 600 (at the indentations 615) or the helix cylinder 58*i* or either jaw 260*i*, 260*j* in order to articulate the jaws 260*i*, 262*i* into a position where the jaws 260*i*, 262*i* can grasp the desired vessel or tissue. On the other hand, if the jaws 260*i*, 626*i* have been inserted through a large incision or port, the surgeon can use his or her hands to articulate the jaws 260*i*, 262*i*. After the jaws 260*i*, 262*i* have been articulated to the desired position, the handle assembly 26*i* can be closed to cause the jaws 260*i*, 262*i* to grip the selected tissue or vessel, or to occlude a vessel, or to ablate, cauterize and/or coagulate.

FIGS. 49–53 illustrate some modifications that can be made to the gripping assembly 30*i* in FIGS. 39–46. As a result, the elements of the clamp 20*j* in FIGS. 49–54 that are the same as those in the embodiment of FIGS. 39–46 bear the same numeral designation as the corresponding elements in FIGS. 39–46, except that a "j" has been added to the numeral designations in FIGS. 49–54. The gripping assembly in FIGS. 49–54 operates in the same manner as the gripping assembly in FIGS. 39–46.

Figure 51:
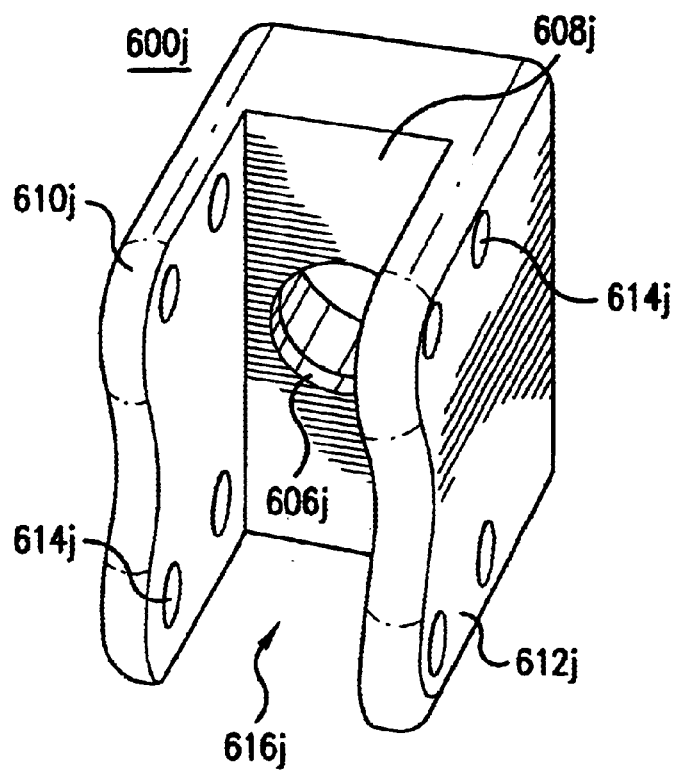
FIG. 51 is a proximal perspective view of the jaw housing of the gripping assembly of FIG. 49.
Figure 52:
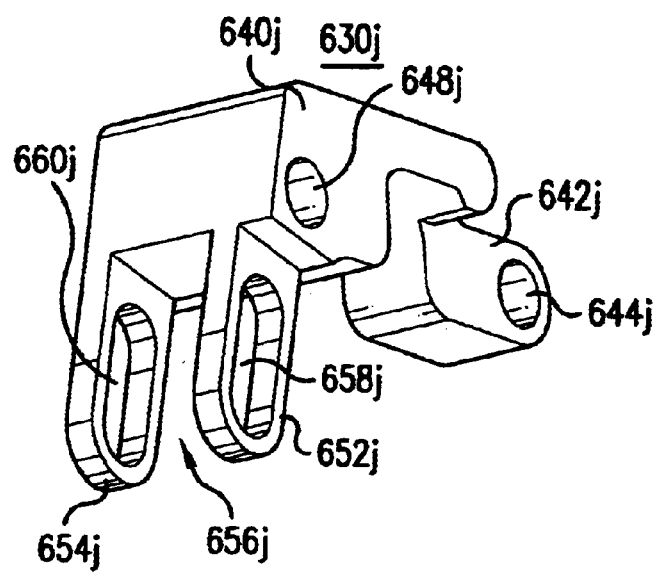
FIG. 52 is a perspective view of the first link of the gripping assembly of FIG. 49.
Figure 53:
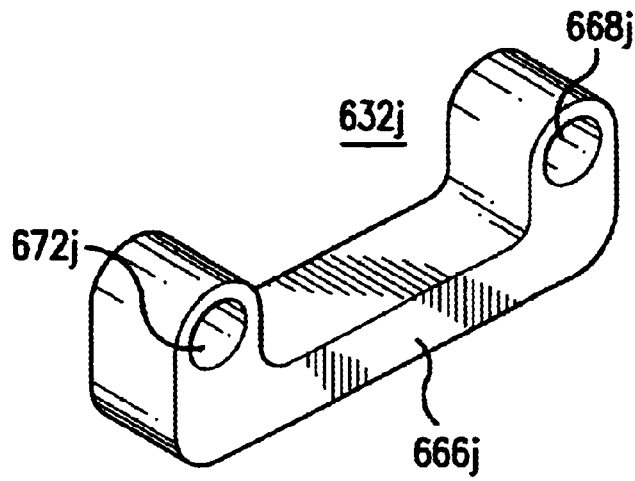
FIG. 53 is a perspective view of the second link of the gripping assembly of FIG. 49.

In the embodiment in FIGS. 49–54, the first link 630*j* and the second link 632*j* have a different configuration from the first link 630 and the second link 632 in FIGS. 39–46. Referring to FIG. 52, the first link 630*j* has a generally L-shaped body 640*j* having a tongue 642*j* extending from one end of the body 640*j*. The tongue 642*j* has an opening 644*j* which receives a dowel pin 646*j*. The central portion of the body 640*j* also has an opening 648*j* which receives another dowel pin 650*j*. Two parallel extensions 652*j* and 654*j* extend from the other end of the body 640*j* and define a space 656*j* therebetween. Each extension 652*j* and 654*j* has an elongated opening 658*j* and 660*j*, respectively.

The second link 632*j* has a generally U-shaped body 666*j* having an opening 668*j* at a curved first end which receives a dowel pin 670*j*, and another opening 672*j* at a second curved end which receives another dowel pin 674*j*.

Referring to FIG. 51, the jaw housing 600*j* is essentially the same as the jaw housing 600 in FIGS. 43A and 43B, except that the openings 614*j* are arranged in different locations. In particular, the openings 614 in FIGS. 43A and 43B are arranged in one vertical line, while the openings 614*j* in FIG. 51 are arranged in two separate horizontal rows. Notwithstanding the fact that the openings 614 and 614*j* are illustrated in FIGS. 43B and 51 as being arranged in a vertical line or in two separate horizontal rows, it is also possible to arrange each the openings 614 and 614*j* in any manner to optimize the opening and closing operation of the parallel jaws 260*i*, 262*i*, 260*j*, 262*j*.

Figure 54:
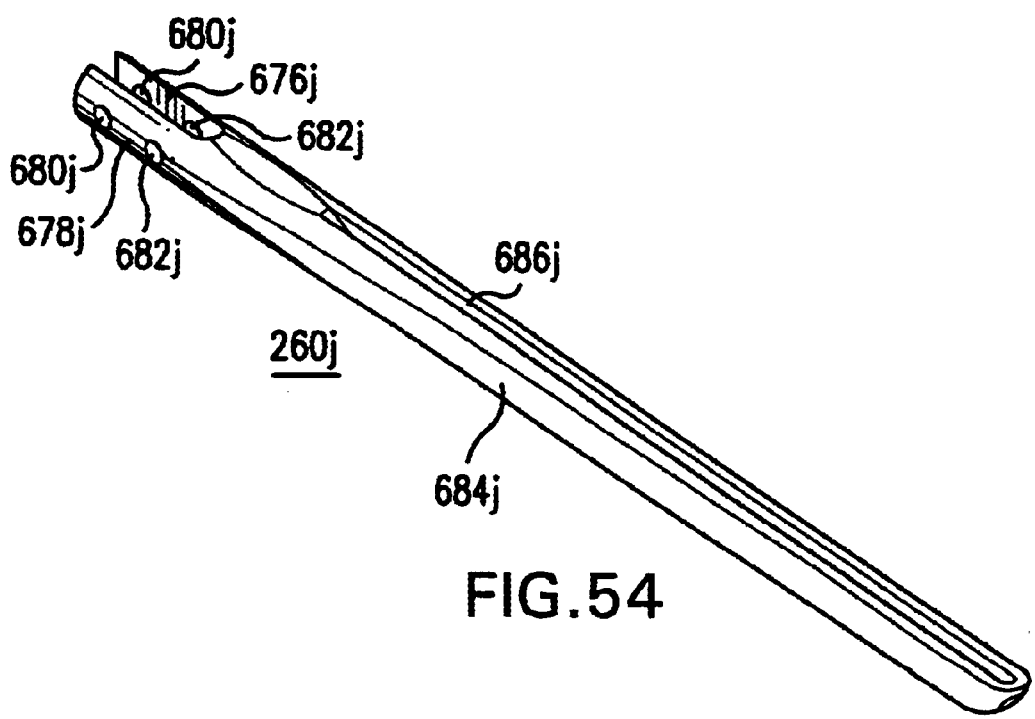
FIG. 54 is a perspective view of the lower jaw of the gripping assembly of FIG. 49.

Similarly, referring to FIG. 54, the jaws 260*j* and 262*j* are essentially the same as the jaws 260*i* and 262*i* in FIG. 46, except that the openings 680*j* and 682*j* are arranged in different locations. In particular, the openings 680 and 682 in FIG. 46 are arranged in one vertical line, while the openings 680*j* and 682*j* in FIG. 54 are arranged in one horizontal line. Notwithstanding the fact that each pair of openings 680+682 and 680*j*+682*j* is illustrated in FIGS. 46 and 54 as being arranged in a horizontal or vertical line, it is also possible to arrange each pair of openings 680+682 and 680*j*+682*j* at an angle with respect to each other.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A clamp comprising:
   a handle assembly;
   a gripping assembly having a pair of jaws that can be opened and closed to grip an element, the pair of jaws being parallel to each other when they are opened and when they are closed; and
   a flexible shaft having a proximal end that is operatively coupled to the handle assembly and a distal end that is operatively coupled to the gripping assembly;
   wherein the shaft is completely flexible without any external support yet is capable of withstanding axial loads; and
   further including a rigid element that can be placed in a first position where the rigid element supports the shaft in a manner where the shaft cannot be bent and in a second position where a portion of the shaft can be bent.

2. The clamp of claim 1, wherein the pair of jaws are parallel to each other at all times, including when the jaws are being opened and being closed.

3. The clamp of claim 1, further including:
- a cable carried within the shaft, the cable having a proximal end that is operatively coupled to the handle assembly and a distal end that is operatively coupled to the gripping assembly; and
- wherein the gripping assembly includes:
  - a jaw housing;
  - a cable terminator movably retained inside the jaw housing and securing the distal end of the cable; and
  - a link that pivotably couples each jaw to the jaw housing.

4. The clamp of claim 3, wherein each link is also pivotably coupled to the cable terminator.

5. The clamp of claim 3, wherein each link is a first link, and further including a second link that pivotably couples each jaw to the jaw housing.

6. The clamp of claim 1, wherein each jaw receives an insert, and wherein a space is defined between the insert on each jaw when the jaws are in the closed position.

7. A method of performing a medical procedure, comprising:
- (a) providing a clamp comprising:
  - a handle assembly;
  - a gripping assembly having a pair of jaws that can be opened and closed; and
  - a flexible shaft having a proximal end that is operatively coupled to the handle assembly and distal end that is operatively coupled to the gripping assembly;
- (b) inserting the jaws through a first incision or port;
- (c) inserting a secondary instrument through a second incision or port so that the secondary instrument can grip the jaws and articulate the jaws to a desired position; and
- (d) causing the jaws to be closed to grip a blood vessel or tissue.

8. The method of claim 7, wherein the clamp further includes a rigid element that covers the shaft and that can be retracted along the shaft, the method further including:
- retracting the rigid element along the shaft so as to expose a portion of the flexible shaft; and
- bending the exposed portion of the flexible shaft.

9. A method of performing a medical procedure, comprising:
- (a) providing a clamp comprising:
  - a handle assembly;
  - a gripping assembly having a pair of jaws that can be opened and closed; and
  - a flexible shaft having a proximal end that is operatively coupled to the handle assembly and a distal end that is operatively coupled to the gripping assembly;
- (b) inserting the jaws through an incision or port;
- (c) inserting a secondary instrument through the same incision or port so that the secondary instrument can grip the jaws and articulate the jaws to a desired position; and
- (d) causing the jaws to be closed to grip a blood vessel or tissue.

10. The method of claim 9, wherein the clamp further includes a rigid element that covers the shaft and that can be retracted along the shaft, the method further including:
- retracting the rigid element along the shaft so as to expose a portion of the flexible shaft; and
- bending the exposed portion of the flexible shaft.

* * * * *